US007250263B2

(12) United States Patent
Klein et al.

(10) Patent No.: US 7,250,263 B2
(45) Date of Patent: Jul. 31, 2007

(54) METHODS AND COMPOSITIONS FOR IDENTIFYING RECEPTOR EFFECTORS

(75) Inventors: Christine A. Klein, Ossining, NY (US); Andrew J. M. Murphy, Croton-on-Hudson, NY (US); Dana M. Fowlkes, Chapel Hill, NC (US); James Broach, Princeton, NJ (US); John Manfredi, Ossining, NY (US); Jeremy Paul, Nyack, NY (US); Joshua Trueheart, Nyack, NY (US)

(73) Assignee: Cadus Technologies, Inc., New York, NY (US)

( * ) Notice: Subject to any disclaimer, the term of this patent is extended or adjusted under 35 U.S.C. 154(b) by 31 days.

(21) Appl. No.: 10/752,478

(22) Filed: Jan. 5, 2004

(65) Prior Publication Data
US 2005/0059135 A1 Mar. 17, 2005

Related U.S. Application Data

(63) Continuation of application No. 09/953,354, filed on Sep. 13, 2001, now abandoned, which is a continuation of application No. 08/689,172, filed on Aug. 6, 1996, now abandoned, which is a continuation-in-part of application No. 08/582,333, filed on Jan. 17, 1996, now Pat. No. 6,255,059, which is a continuation-in-part of application No. 08/322,137, filed on Oct. 13, 1994, now Pat. No. 6,100,042, which is a continuation-in-part of application No. 08/309,313, filed on Sep. 20, 1994, now abandoned, which is a continuation-in-part of application No. 08/190,328, filed on Jan. 31, 1994, now abandoned, which is a continuation-in-part of application No. 08/041,431, filed on Mar. 31, 1993, now abandoned.

(51) Int. Cl.
*C12N 15/81* (2006.01)
*C40B 40/02* (2006.01)

(52) U.S. Cl. .................. 435/7.1; 435/252.3; 435/483

(58) Field of Classification Search .................. None
See application file for complete search history.

(56) References Cited

U.S. PATENT DOCUMENTS

| 4,418,149 | A | 11/1983 | Ptashne et al. | |
|---|---|---|---|---|
| 4,833,080 | A | 5/1989 | Brent et al. | |
| 4,948,874 | A | 8/1990 | Kronvall et al. | 530/350 |
| 5,096,815 | A | 3/1992 | Ladner et al. | 435/69.1 |
| 5,283,173 | A | 2/1994 | Fields et al. | 435/6 |
| 5,284,746 | A | 2/1994 | Sledziewski et al. | |
| 5,401,629 | A | 3/1995 | Harpold et al. | 435/6 |
| 5,436,128 | A | 7/1995 | Harpold et al. | 435/6 |
| 5,468,614 | A | 11/1995 | Fields et al. | 435/6 |
| 5,573,944 | A | 11/1996 | Kirschner et al. | |
| 5,580,736 | A | 12/1996 | Brent et al. | 435/6 |
| 5,691,188 | A | 11/1997 | Pausch et al. | 435/225.1 |
| 5,739,029 | A * | 4/1998 | King et al. | 435/254.21 |
| 5,789,184 | A | 8/1998 | Fowlkes et al. | |
| 5,876,951 | A | 3/1999 | Fowlkes et al. | |
| 6,100,042 | A | 8/2000 | Fowlkes et al. | |
| 6,255,059 | B1 | 7/2001 | Klein et al. | |

FOREIGN PATENT DOCUMENTS

| EP | 0 568 925 | 11/1993 |
|---|---|---|
| WO | WO 8810308 | 12/1988 |
| WO | WO 90/05780 | 5/1990 |
| WO | WO 9112273 | 8/1991 |
| WO | WO 92/05244 | 4/1992 |
| WO | WO 92/08740 | 5/1992 |
| WO | WO 93/10230 | 5/1993 |
| WO | WO 94/23025 | 10/1994 |
| WO | WO 9530012 | 11/1995 |
| WO | WO 9711159 | 3/1997 |
| WO | WO 9813513 | 4/1998 |

OTHER PUBLICATIONS

Alison, M.R. et al. "Growth factors and growth factor receptors" *British Journal of Hospital Medicine* 49(11):774-788 (1993).
Altieri, D.C. "Proteases and protease receptors in modulation of leukocyte effector functions" *Journal of Leukocyte Biology* 58:120-127 (1995).
Belka, C. et al. "The role of tyrosine kinases and their substrates in signal transmission of hematopoietic growth factors: a short review" *Leukemia* 9:754-761 (1995).
Birnbaumer, L. "Transduction of receptor signal into modulation of effector activity by G proteins: the first 20 years or so . . . " *FASEB Journal* 4:3178-3188 (1990).
Boulay, F. et al. "Synthesis and Use of a Novel N-Formyl Peptide Derivative to Isolate a Human N-Formyl Peptide Receptor cDNA" *Biochem. Biophys. Res. Commun.* 168(3):1103-1109 (1990).
Boulay; F. et al. "Expression Cloning of a Receptor for C5a Anaphylatoxin on Differentiated HL-60 Cells" *Biochemistry* 30:2993-2999 (1991).
Brugarolas, J. et al. "Radiation-induced cell cycle arrest compromised by p21 deficiency" *Nature* 377:552-557 (1995).
Chambers, D.A. et al. "Neuroimmune Modulation: Signal Transduction and Catecholamines" *Neurochem. Int.* 22(2):95-110 (1993).
Chien, Cheng-Ting, et al. "The Two-Hybrid System: A Method To Identify and Clone Genes For Proteins That Interact With A Protein of Interest", Proc. Natl. Acad. Sci, USA, vol. 88, pp. 9578-9582, (1991).
Cwirla, S. et al. "Peptides on Phage: A Vast Library of Peptides for Identifying Ligands" *Proc. Natl. Acad. Sci. USA* 87:6378-6382 (1990).

(Continued)

Primary Examiner—John Ulm
(74) *Attorney, Agent, or Firm*—Edwards Angell Palmer & Dodge LLP; Peter C. Lauro, Esq.

(57) ABSTRACT

The present invention makes available a rapid, effective assay for screening and identifying pharmaceutically effective compounds that specifically interact with and modulate the activity of a cellular receptor or ion channel. The subject assay enables rapid screening of large numbers of polypeptides in a library to identifying those polypeptides which induce or antagonize receptor bioactivity. The subject assay is particularly amenable for identifying surrogate ligands for orphan receptors.

25 Claims, 12 Drawing Sheets

OTHER PUBLICATIONS

Devlin, J. et al. "Random Peptide Libraries: A Source of Specific Protein Binding Molecules" *Science* 249:404-406 (1990).
Dubois, P.M. "Role of the transmembrane and cytoplasmic domains of surface IgM in endocytosis and signal transduction" *Eur. J. Immunol.* 22:851-857 (1992).
Erickson, D. "Intercepted Messages: New biotechnology drugs target intracellular communication" *Scientific American* (Nov. 1992):122-123.
Fields, Stanley, et al. "A Novel Genetic System To Detect Protein—Protein Interactions", Nature, vol. 340, pp. 245-246, (1989).
Funaro, A. et al. "Human CD38 is associated to distinct molecules which mediate transmembrane signaling in different lineages" *Eur. J. Immunol.* 23:2407-2411 (1993).
Gordon, J. "B-cell signalling *via* the C-type lectins CD23 and CD72" *Immunology* 15(9):411-417 (1994).
Gyuris, Jeno et al. "Cdi1, A Human G1 and S Phase Protein Phosphatase That Assocites With CdK2", Cell, vol. 75, pp. 791-803, (1993).
Hall, M. et al. "Evidence for different modes of action of cyclin-dependent kinase inhibitors: p15 and p16 bind to kinases, p21 and p27 bind to cyclins" *Oncogene* 11:1581-1588 (1995).
Hughes, David, et al. "complementation of byr1 in Fission Yeast By Mammalian MAP Kinase Kinase Requires CoExpression of Raf Kinase", Nature, vol. 364, pp. 349-352, (1993).
Imamoto, A. et al. "Genetics of signal transduction: tales from the mouse"0 *Curr. Opion. Gen. & Dev.* 4:40-46 (1994).
Jakobs, K.H. et al. "Dual regulation of adenylate cyclase. A signal transduction mechanism of membrane receptors" *Basic Res. Cardiol.* 81:1-9 (1986).
Kang, Y-S et al., "Effects of expression of mammalian G □ and hybrid mammalian-yeast G□ proteins on the yeast pheromone response signal transduction pathway." Molecular and Cellular Biology, 10(6):2582-250 (1990).
King, K. et al. "Control of Yeast Mating Signal Transduction by a Mammalian $\beta_2$-Adrenergic Receptor and $G_s$ $\alpha$ Subunit" *Science* 250:121-123 (1990).
Koff, Andrew, et al. "Human Cyclin E, A New Cyclin That Interacts With Two Members of the CDC2 Gene Family", Cell, vol. 66, pp. 1217-1228; (1991).
Kosugi, S. et al. "Characterization of heterogeneous mutations causing constitutive activation of the luteinizing hormone receptor in familial male precocious puberty" *Human Molecular Genetics* 4(2):183-188 (1995).
Lew, D.J. et al. "Isolation of Three Novel Human Cyclins by Rescue of G1 Cyclin (Cln) Function in Yeast" *Cell.* 66:1197-1206 (1991).
Linder, M.E. and A.G. Gilman "G Proteins" *Scientific American* Jul. 1992:56-65.
Manfredi, J. et al., "Autocrine stimulation of yeast through human G-coupled receptors," *J. Cell. Biochem.*, 18B:224 (1994).
Marengere, L.E.M. and T. Pawson "Structure and function of SH2 domains" *J. Cell Science Suppl.* 18:97-104 (1994).
Milburn, M.V. et al. "Molecular Switch for Signal Transduction: Structural Differences Between Active and Inactive Forms of Protooncogenic *ras* Proteins" *Science* 247:939-945 (1990).
Murphy, A.J.M, et al. "Autocrine Stimulation of Yeast Through Human G-Coupled Receptors," *J. Cell Biochem.* 18B:224 (1994).
Murphy, P.M. et al. "Functional Expression of the Human Formyl Peptide Receptor in *Xenopus* Oocytes Requires a Complementary Human Factor" *J. Biol. Chem.* 266(19):12560-12567 (1991).
Ngo, J.T. et al. "Computational Complexity, Protein Structure Prediction, and the Levinthal Paradox" In: *The Protein Folding Problem and Tertiary Structure Prediction* Mertz et al. (eds.) Birkhauser, Boston, Massachusetts, p. 433, 492-495 (1954).
Noelle, R.J. et al. "CD40 and it ligand, an essential ligand-receptor pair for thymus-dependent B-cell activation" *Immunology Today* 13(11):431-433 (1992).
Nye, J.S. and R. Kopan "Vertebrate ligands for Notch" *Current Biololgy* 5(9):966-969 (1995).
Ranade, K. et al. "Mutations associated with familial melanoma impair p16[INK4] funtion" *Nature Genetics* 10:114-116 (1995).

Raymond, M. et al. "Functional Complementation of Yeast ste6 by a Mammalian Multidrug Resistance mdr Gene" *Science* 256:232-234 (1992).
Reed, R.R. "G Protein Diversity and the Regulation of Signaling Pathways" *The New Biologist* 2(11):957-960 (1990).
Scott, J.K. and G.P. Smith "Searching for Peptide Ligands with an Epitope Library" *Science* 249:386-390 (1990).
Suzuki, T. et al. "HTLV-1 Tax protein interacts with cyclin-dependent kinase inhibitor p16[INK4A] and counteracts its inhibitory activity towards CDK4" *EMBO J.* 15(7):1607-1614 (1996).
Thien-Khai, H.V. et al. "Molecular Cloning of a Funcional Thrombin Receptor Reveals a Novel Proteolytic Mechanism of Receptor Activation" *Cell* 64:1057-1068 (1991).
Vu et al. "Molecular cloning of a funcional thrombin receptor reveals a novel proteolytic mechanism of receptor actvation" *Cell* 64:1057-1068 (1991).
Whiteway, M. et al. "Dominant negative selection of heterologous genes: Isolation of *Candida albicans* genes that interfere with *Saccharomyces cerevisiae* mating factor-induced cell cycle arrest" *Proc Natl. Acad. Sci. USA* 89:9410-9414 (1992).
Wolowiec, D. et al. "Expression of cell cycle regulatory proteins in chronic lymphocytic leukemias. Comparison with non-Hodgkin's lymphomas and non-neoplastic lymphoid tissue" Leukemia 9:1382-1388 (1995).
Xiong, Y. et al. "Alteration of Cell Cycle Kinase Complexes in Human Papillomavirus E6- and E7- Expressing Fibroblasts Precedes Neoplastic Transformation" *J. Virol.* 70(2):999-1008.
Xiong, Y. et al. "Human D-Type Cyclin" *Cell* 65:691-699 (1991).
Zervos, Antonis et al. "Mxi1, A Protein That Specifically Interacts With Max to Bind Myc-Max Recognition Sites", Cell, vol. 72, pp. 223-232, (1993).
U.S. Appl. No. 09/258,600, filed Feb. 1999, Fowlkes et al.
U.S. Appl. No. 09/286,166, filed Apr. 1999, Fowlkes et al.
U.S. Appl. No. 09/581,861, filed Mar. 2001, Broach et al.
U.S. Appl. No. 09/747,774, filed Dec. 2000, Klein et al.
U.S. Appl. No. 10/263,341, filed Oct. 2002, Fowlkes et al.
U.S. Appl. No. 10/277,607, filed Oct. 2002, Klein et al.
U.S. Appl. No. 10/752,478, filed Jan. 2004, Klein et al.
U.S. Appl. No. 10/600,003, filed Jun. 18, 2003, Fowlkes et al.
U.S. Appl. No. 08/946,298, filed Oct. 7, 1997, Fowlkes et al.
Akada, R. et al. "Genetic Relationships Between the G Protein $\beta\gamma$ Complex, Ste5p, Ste20p and Cdc42p: Investigation of Effector Roles in the Yeast Pheromone Response Pathway," *Genetics* 143:103-117 (1996).
Zhan, Xiao-Li et al. "Differential regulation of *FUS3* MAP kinase by tyrosine-specific phosphatases *PTP2/PTP3* and dual-specificity phosphatase *MSG5* in *Saccharomyces cerevisiae,*" *Genes & Development* 11:1690-1702 (1997).
Artemyev, Nikolai O. et al. "Sites of Interaction between Rod G-Protein $\alpha$-Subunit and cGMP-phosphodiesterase $\gamma$-Subunit," *J. Biol. Chem.* 267(35):25067-72 (1992).
Awramik, S. M. "New fossil finds in old rocks," *Nature* 319:446-47 (1986).
Barella et al. "Sequence variation of a novel heptahelical leucocyte receptor through alternative transcript formation" *Biochem. J.* 309: 773-779 (1995).
Bender, Alan and Sprague, George F. Jr. "Pheromones and Pheromone Receptors Are the Primary Determinants of Mating Specificity in the Yeast *Saccharomyces cerevisiae,*" *Genetics* 121:463-76 (1989).
Blinder, Dmitry et al. "Constitutive Mutants in the Yeast Pheromone Response: Ordered function of the Gene Products," *Cell* 56:479-486 (1989).
Bray, P. et al., "Human cDNA clones for four species of G alpha s signal transduction protein," *PNAS USA*, Dec. 1986;83(23):8893-7.
Bray, P. et al., "Human cDNA clones for an alpha subunit of Gi signal-transduction protein," *PNAS USA*, Aug. 1987;84(15):5115-9.
Brill, Julie A. et al. "A Role for Autophosphorylation Revealed by Activated Alleles of *FUS3*, the Yeast MAP Kinase Homolog," *Molecular Biology of the Cell* 5:297-312 (1994).
Burack, W. Richard et al. "The Activating Dual Phosphorylation of MAPK by MEK is Nonprocessive," *Biochemistry* 36(20):5929-5933 (1997).

Cavallini, Bruno et al. "A yeast activity can substitute for the HeLa Cell TATA box factor," *Nature* 334:77-80 (1988).

Chan, Russell K. and Otte, Carol A. "Isolation and Genetic Analysis of *Saccharomyces cerevisiae* Mutants Supersensitive to G1 Arrest by a Factor and α Factor," *Molecular and Cellular Biol.* 2(1):11-20 (1982).

Chang, Fred and Herskowitz, Ira "Identification of a Gene Necessary for Cell Cycle Arrest by a Negative Growth Factor of Yeast: FAR1 is an Inhibitor of a G1 Cyclin, CLN2," *Cell* 63:999-1011 (1990).

Clark, Karen L. et al. "Interactions among the Subunits of the G-protein Involved in *Saccharomyces cerevisiae* Mating," *Molecular and Cellular Biol.* 13(1):1-8 (1993).

Cole, Gary M. et al. "Stoichiometry of G Protein Subunits Affects the *Saccharomyces cerevisiae* Mating Pheromone Signal Transduction Pathway," *Molecular and Cellular Biology* 10(2):510-517 (1990).

Coleman, David E. et al. "Structures of Active Conformation of $G_{i\alpha}$ and the Mechanism of GTP Hydrolysis," *Science* 265:1405-12 (1994).

Conklin, Bruce R. et al. "Substitution of three amino acids switches receptor specificity of $G_{q\alpha}$ to that of $G_{i\alpha}$," *Nature* 363:274-76 (1993).

Dietzel, Christine et al. "Pheromonal regulation and sequence of the *Saccharomyces cerevisiae* SST2 gene: a model for desensitization to pheromone." *Mol. Cell. Biol.* 7(12):4169-4177, Dec. 1987.

Dmochowska, Aleksandra et al. "Yeast *KEX1* Gene Encodes a Putative Protease with a Carboxypeptidase B-like Function Involved in Killer Toxin and α-Factor Precursor Processing," *Cell* 50:573-84 (1987).

Dolan, J. W. et al. "Overproduction of the yeast STE12 protein leads to constitutive transcriptional induction," *Genes & Development* 4(4):492-502 (1990).

Etienne, Gilles et al. "A Screening Method for Antifungal Substances Using *Saccharomyces cerevisiae* Strains Resistant to Polyene Macrolides," *J. of Antibiotics* 43(2):199-206 (1990).

Fasullo, Michael T. and Davis, Ronald W. "Direction of Chromosome Rearrangements in *Saccharomyces cerevisiae* by Use of *his3* Recombination Substrates," *Molecular and Cellular Biol.* 8(10):4370-80 (1988).

Ferrell, James E. Jr. et al. "The Biochemical Basis of an All-or-None Cell Fate Switch in *Xenopus* Oocytes," *Science* 280:895-898 (1998).

Ferrell, James E. Jr. "Tripping the switch fantastic: how a protein kinase cascade can convert graded inputs into switch-like outputs," *Trends In Biochem. Sci.* 21(12):460-6 (1996).

Franke, Arthur E. et al. "Human C5a Anaphylatoxin: Gene Synthesis, Expression, and Recovery of Biologically Active Material from *Escherichia coli*," *Methods in Enzymology* 162:653-68 (1988).

Gallego, Carme et al. "Myristoylation of the $G\alpha_{i2}$ polypeptide, a G protein α subunit, is required for its signaling and transformation functions," *Proc. Natl. Acad. Sci. USA* 89:9695-99 (1992).

Garritsen, Anja et al. "The N-Terminal coiled-coil domain of β is essential for γ association: A Model for G-Protein βγ subunit interaction," *Proc. Natl. Acad. Sci. USA* 90:7706-10 (1993).

Gerard, Norma P. and Gerard, Craig "Construction and Expression of a Novel Recombinant Anaphylatoxin, C5a-N19, a Probe for the Human C5a Receptor," *Biochemistry* 29(39):9274-81 (1990).

Graf, Rolf et al. "A Truncated Recombinant α Subunit of $G_{i3}$ with a Reduced Affinity for βγ Dimers and Altered Guanosine 5'-3-O-(Thio)triphosphate Binding," *J. of Biol. Chem.* 267(34):24307-14 (1992).

Gros, Philippe et al. "Mammalian Multidrug Resistence Gene: Complete cDNA Sequence Indicates Strong Homology to Bacterial Transport Proteins," *Cell* 47:371-80 (1986).

Hagen, David C. et al. "Evidence the yeast *STE3* gene encodes a receptor for the peptide pheromone a factor: Gene sequence and implications for the structure of the presumed receptor,"*Proc. Natl. Acad. Sci. USA* 83:1418-22 (1986).

Harbury, Pehr B. et al. "A Switch Between Two-, Three- and Four-Stranded Coiled Coils in GCN4 Leucine Zipper Mutants," *Science* 262:1401-07 (1993).

Hartwell, Leland H. "Mutants of *Saccharomyces cerevisiae* Unresponsive to Cell Division Control by Polypeptide Mating Hormone," *J. Cell. Biol.* 85:811-22 (1980).

Hasson, M.S. et al. "Mutational Activation of the *STE5* Gene Product Bypasses the Requirement for G Protein β and γ Subunits in the Yeast Pheromone Response Pathway," *Molecular and Cellular Biology* 14(2):1054-1065 (1994).

He, Bin et al. "*RAM2*, an essential gene of yeast, and *RAM1* encode the two polyeptide components of the farnesyltransferase that prenylates a-actor and Ras proteins," *Proc. Natl. Acad. Sci. USA* 88:11373-77 (1991).

Hiltunen, J. Kalervo et al. "Peroxisomal Multifunctional β-Oxidation Protein of *Saccharomyces cerevisiae*," *J. of Biol. Chem.* 267(10):6646-6653 (1992).

Hrycyna, Christine A. et al. "The *Saccharomyces cerevisiae STE14* gene encodes a methyltransferase that mediates C-terminal methylation of a-factor and RAS Proteins," *The EMBO J.* 10(1):1699-1709 (1991).

Huang, Chi-Ying F. et al. "Ultrasensitivity in the mitogen-activated protein kinase cascade," *Proc. Natl. Acad. Sci. USA* 93:10078-10083 (1996).

Inouye, Carla et al. "Ste5 RING-H2 Domain: Role in Ste4-Promoted Oligomerization for Yeast Pheromone Signaling," *Science* 278:103-106 (1997).

Jabbar, M. Abdul et al. "Influenza Viral (A/WSN/33) hemagglutinin is expressed and glycosylated in the yeast *Saccharomyces cerevisiae*," *Proc. Natl. Acad. Sci. USA* 82:2019-23 (1985).

Journot, Laurent et al. "Amino Acids 367-376 of the $G_s$ α subunit induce membrane association when fused to soluble amino-terminal deleted $G_{i1}$ a subunit," *Proc. Natl. Acad. Sci. USA* 88:10054-58 (1991).

Julius, David et al. "Glycosylation and Processing of Prepro-α-Factor through the Yeast Secretory Pathway," *Cell* 36:309-18 (1984).

Julius, David et al. "Isolation of the Putative Structural Gene for the Lysine-Arginine-Cleaving Endopeptidase Required for Processing of Yeast Prepro-α-factor," *Cell* 37:1075-89 (1984).

Julius, David et al. "Yeast α Factor is Processed from a Larger Precursor Polypeptide: The Essential Role of a Membrane-Bound Dipeptidyl Aminopeptidase," *Cell* 32:839-52 (1983).

Kaiser, Chris A. et al. "Many Random Sequences Functionally Replace the Secretion Signal Sequence of Yeast Invertase," *Science* 235:312-17 (1987).

Kingsman, S.M. et al. "*The production of mammalian protein in Saccharomyces cerevisiae*," *Tibtech* 5: 53-57 (1987).

Kramer, R. A. et al. "HTLV-III *gag* Protein Is Processed in Yeast Cells by the Virus *pol*-Protease," *Science* 231:1580-85 (1986).

Kuchler, Karl and Thorner, Jeremy "Functional expression of human *mdr1* in the yeast *Saccharomyces cerevisiae*," *Proc. Natl. Acad. Sci. USA* 89:2302-06 (1992).

Kuchler, Karl et al. "*Saccharomyces cerevisiae* STE6 gene product: a novel pathway for protein export in eukaryotic cells," *The EMBO J.* 8(13):3973-84 (1989).

Kurjan, Janet "α-Factor Structural Gene Mutations in *Saccharomyces cerevisiae*: Effects on α-Factor Production and Mating," *Molecular and Cellular Biol.* 5(4):787-96 (1985).

Kurjan, Janet and Herskowitz "Structure of a Yeast Pheromone Gene (*MFα*): A Putative α-Factor Precursor Contains Four Random Copies of Mature α-Factor," *Cell* 30:933-43 (1982).

Lambright, David G. et al. "Structural determinants for activation of the α-subunit of a heterotrimeric G protein," *Nature* 369:621-28 (1994).

Lolait, S. et al., "Extrapituitary expression of the rat V1b vasopressin receptor gene," *PNAS USA* 92:6783-6787 (1995).

Lee, Ethan et al. The G22A Mutant of $G_{s\alpha}$ Highlights the Requirement for Dissociation of G Protein Subunits, *J. Biol. Chem.* 267(2):1212-18 (1992).

Lemire, Bernard D. et al. "The Mitochondrial Targeting Function of Randomly Generated Peptide Sequences Correlates with Predicted Helical Amphiphilicity," *J. Biol. Chem.* 264(34):20206-12 (1989).

Linder, Maurine E. et al. "Lipid Modifications of G Protein Subunits: Myristoylation of $G_{602\ \alpha}$ Increases its Affinity for βγ," *J. Biol. Chem.* 266(7):4654-59 (1991).

Lupas, Andrei N. et al. "Do G protein subunits associate via a three-stranded coiled coil?" *FEBS* 314(2):105-08 (1992).

Mackay, Vivian and Manney, Thomas R. "Mutations Affecting Sexual Conjugation and Related Processes in *Saccharomyces cerevisiae*. II Genetic Analysis of Nonmating Mutants," *Genetics* 76:273-88 (1974).

Manfredi J. et al., "Yeast α Mating Factor Structure-Activity Relationship Derived from Genetically Slected Peptide Agonists and Antagonists of Ste2p", *Molecular and Cellular Biol.* 16(9): 4700-4709 (1996).

Markby, David W. et al. "Separate GTP Binding and GTPase Activating Domains of a Gα Subunit," *Science* 262:1895-1901 (1993).

Mattera, R. et al., "Identification by molecular cloning of two forms of the alpha-subunit of the human liver stimulatory ($G_s$) regulatory component of adenylyl cyclase," *FEBS Lett.*, Sep. 29, 1986;206(1):36-42.

Medici, R. et al. "Efficient signal transduction by a chimeric yeast-mammalian G protein α subunit Gpa1-Gsα covalently fused to the yeast receptor Ste2," *EMBO* 16:7241-7249 (1997).

Michaelis, Susan and Herskowitz, Ira "The a-Factor Pheromone of *Saccharomyces cerevisiae* is Essential for Mating," *Molecular and Cellular Biol.* 8(3):1309-18 (1988).

Milano, C.A. et al. "Enhanced Myocardial Function in Transgenic Mice Overexpressing the $\beta_2$-Adrenergic Receptor," *Science* 264:582-86 (1994).

Mumby, Susanne M. et al. "G-Protein α-subunit expression, myristoylation, and membrane association in COS cells," *Proc. Natl. Acad. Sci. USA* 87:728-32 (1990).

Murphy et al., "A structural homologue of the N-Formyl peptide receptor" *J. Biol. Chem.* 267(11):7637-7643 (1992).

Nakafuku, Masato et al. "Occurrence in *Saccharomyces cerevisiae* of a gene homologous to the cDNA coding for the α-subunit of mammalian G proteins," *Proc. Natl. Acad. Sci. USA* 84:2140-44 (1987).

Nakayama, N. et al. "Common signal transduction system shared by *STE2* and *STE3* in haploid cells of *Saccharomyces cerevisiae*: autocrine cell-cycle arrest results from forced expression of *STE2*," *The EMBO J.* 6(1):249-54 (1987).

Neer, Eva J. et al. "The Amino Terminus of a G Protein α Subunits Is Required for Interaction with βγ," *J. Biol. Chem.* 263(18):8996-9000 (1988).

Noel, Joseph P. et al. "The 2.2 Åcrystal structure of transducin-α complexed with GTP-γ-S," *Nature* 366:654-63 (1993).

Nomoto, Satoshi et al. "Regulation of the yeast pheromone response pathway by G protein subunits," *The EMBO J.* 9(3):691-696 (1990).

Oeda, Kenji et al. "Expression of Rat Liver Cytochrome P-450MC cDNA in *Saccharomyces cerevisiae*, " *DNA* 4(3):203-10 (1985).

Ogden, Jill E. et al. "Efficient Expression of the *Saccharomyces cerevisiae PGK* Gene Depends on an Upstream Activation Sequence but Does Not Require TATA Sequences," *Molecular and Cellular Biol.* 6(12):4335-43 (1986).

Pausch, M.H., *TIBTECH*, 15 (487-494) 1997.

Payette et al., "Expression and pharmacological characterization of the human M1 muscarinic receptor in *Saccharomyces cerevisiae*" *FEBS Letters* 266:21-25 (1990).

Pronin, Alexey N. and Gautam, Narasimhan "Interaction between G-Protein β and γ subunit types is selective," *Proc. Natl. Acad. Sci. USA* 89:6220-24 (1992).

Pi, H. et al. (1997) "Transcriptional activation upon pheromone stimulation mediated by a small domain of *Saccharomyces cerevisiae* Ste12p." *Mol. Cell. Biol.* 17(11):6410-6418 (1987).

Ramer, Sandra W. and Davis, Ronald W. "A dominant truncation allele identifies a gene, *STE20*, that encodes a putative protein kinase necessary for mating in *Saccharomyces cerevisiae*," *Proc. Natl. Acad. Sci. USA* 90:452-456 (1993).

Rarick, Helen M. et al. "A Site on Rod G Protein α Subunit That Mediates Effector Activation," *Science* 256:1031-33 (1992).

Reneke, Johanna E. et al. "The carboxy-terminal segment of the yeast alpha-factor receptor is a regulatory domain" *Cell* 55:221-34 (1988).

Schafer, William R. et al. "Enzymatic Coupling of Cholesterol Intermediates to a Mating Pheromone Precursor and to the Ras Protein," *Science* 249:1133-39 (1990).

Schafer, William R. et al. "Genetic and Pharmacological Suppression of Oncogenic Mutations in *RAS* Genes of Yeast and Humans," *Science* 245:379-85 (1989).

Schärer, E. and Iggo, R. "Mammalian p53 can function as a transcription factor in yeast," *Nucleic Acids Research* 20(7):1539-45 (1992).

Sikorski, Robert S. and Hieter, Philip "A System of Shutte Vectors and Yeast Host Strains Designed for Efficient Manipulation of DNA in *Saccharomyces cerevisiae*," *Genetics* 122:19-27 (1989).

Singh, Arjun et al. "*Saccharomyces cerevisiae* contains two discrete genes coding for the α-factor pheromone," *Nucleic Acids Research* 11(12):4049-63 (1983).

Slepak, Vladlen Z. et al. "Mutational Analysis of G Protein α Subunit $G_{o2}$ α Expressed in *Escherichia coli*," *J. Biol. Chem.* 268(2):1414-23 (1993).

Spiegel, Allen M. et al. "The G Protein connection: molecular basis of membrane association," *TIBS* 16:338-41 (1991).

Steube, Klaus et al. "α-Factor-leader-directed secretion of recombinant human-insulin-like growth factor I from *Saccharomyces cerevisiae*," *Eur. J. Biochem.* 198:651-57 (1991).

Stevenson, Brian J. et al. "Constitutive mutants of the Protein Kinase STE11 Activate the Yeast Pheromone Response Pathway in the Absence of the G Protein," *Genes & Development* 6:1293-1304 (1992).

Strubin, Michel and Struhl, Kevin "Yeast and Human TFIID with Altered DNA-Binding Specificity of TATA Elements," *Cell* 68:721-30 (1992).

Struhl, Kevin "Constitutive and Inducible *Saccharomyces cerevisiae* Promoters: Evidence for Two Distinct Molecular Mechanisms," *Molecular and Cellular Biol.* 6(11):3847-53 (1986).

Stedman's Medical Dictionary, 27th ed. 2000, entry: "heterologous".

Struhl, Kevin et al. "High-frequency transformation of yeast: Autonomous replication of hybrid DNA molecules," *Proc. Natl. Acad. Sci. USA* 76(3):1035-39 (1979).

Struhl, Kevin and Hill, David E. "Two Related Regulatory Sequences are Required for Maximal Induction of *Saccharomyces cerevisiae his3* Transcription," *Molecular and Cellular Biol.* 7(1):104-10 (1987).

Sullivan, Kathleen A. et al., "Identification of receptor contact site involved in receptor-G protein coupling," *Nature* 330:758-60 (1987).

Stryer et al., "G Proteins: A family of signal transducers" *Ann. Rev. Cell Biol.* 2: 391-419 (1986).

Tate and Grisshammer, "Heterologous expression of G-protein-coupled receptors" *TIBTECH* 14: 426-430 (1996).

Teem, John L. et al. "Identification of Revertants for the Cystic Fibrosis ΔF508 Mutation Using STE6-CFTR Chimeras in Yeast," *Cell* 73:335-346 (1993).

Thomas, Thomas C. et al. "G-protein $\alpha_{o2}$ subunit: Mutation of conserved cysteines identifies a subunit contact surface and alters GDP affinity," *Proc. Natl. Acad. Sci. USA* 90:10295-99 (1993).

Tyson, John J. et al. "Chemical kinetic theory: understanding cell-cycle regulation," *Trends In Biochem. Sci.* 21:89-96 (1996).

Walker, John E. et al. "Distantly related sequences in the α-and β-subunits of ATP synthase, myosin, kinases and other ATP-requiring enzymes and a common nucleotide binding fold," *The Embo J.* 1(8):945-51 (1982).

Waters, M. Gerard et al. "Prepro-α-factor Has a Cleavable Signal Sequence," *J. Biol. Chem.* 263(13):6209-14 (1988).

Watson and Arkinstall, "The G-protein linked receptor facts book" Academic Press, New York, pp. 5 (1994).

Whiteway, Malcolm S. et al. "Association of the Yeast Pheromone Response G Protein βγ Subunits with the MAP Kinase Scaffold Ste5p," *Science* 269:1572-1575 (1995).

Ye et al., "Isolation of a cDNA that encodes a novel granulocyte N-Formyl peptide receptor" *Biochem. Biophys. Res. Commun.* 184(2):582-589 (1992).

* cited by examiner

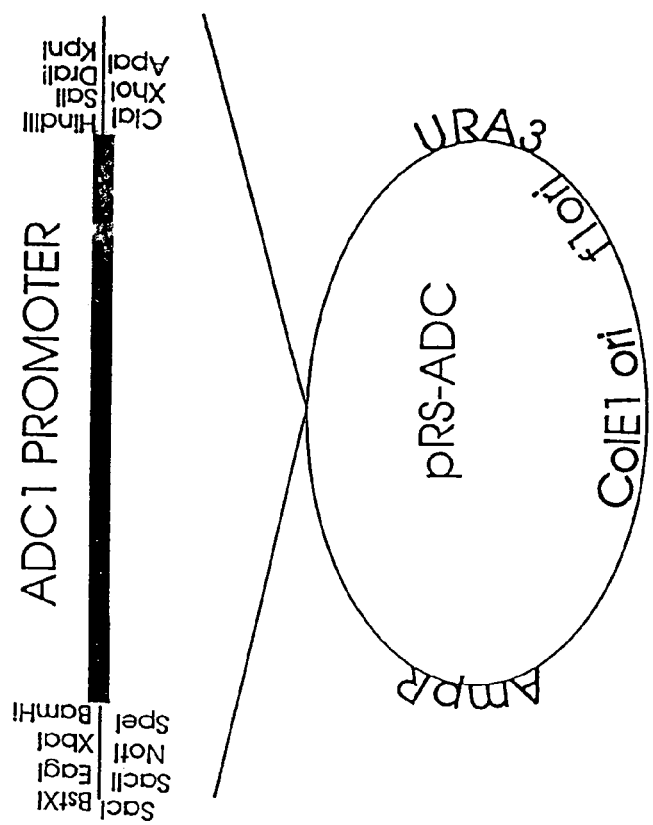
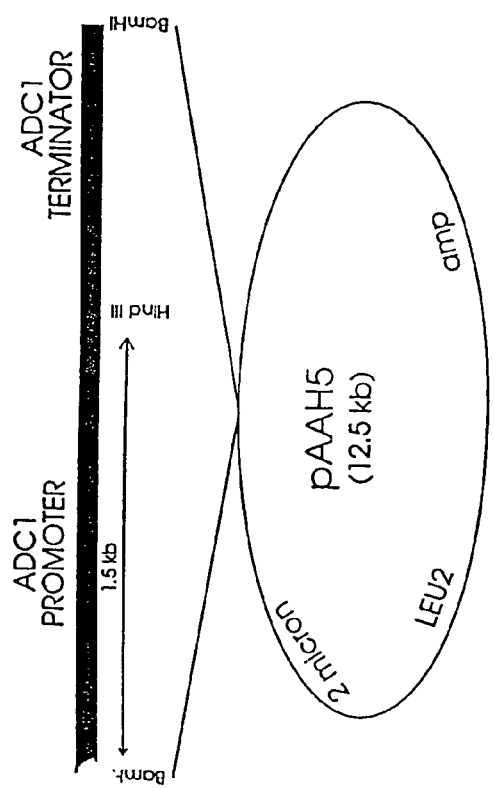
Figure 1

Stimulation of C5aR-Containing Yeast By Surrogate Peptide Agonists 1     0.33    0.1 mg/ml peptide 133 peptide 122

DMF control peptide 36 peptide 73

| | |
|---|---|
| 14 | Phe Leu Glu Cys Pro His Ser Gly Phe Gly Thr Cys Val |
| JH19 | Cys Leu Arg Val Phe Leu Pro Trp His Phe Val Leu Cys |
| 314, JH36, JH39 | Arg Val Phe Arg Trp Cys Tyr Phe Met Ser Glu Cys Val |
| 33 | Ala Tyr Arg Gly Ser Phe Lys Leu Leu Leu Ile Trp Thr |
| 36 | Val Gly Trp Pro Leu Val Ala Trp Asn Leu Leu Gly Trp |
| 133, 134 | Ser Leu Ser Thr Phe Lys Cys Arg Leu Leu Trp Val Thr |
| 137 | Leu Gly Ser Val Ala Arg Val Arg Leu Cys Leu Val Cys |
| JH73, JH80 | Gly Ile Ala Thr Asp Phe Arg Leu Cys Leu Leu Leu Cys |
| JH101 | Val Trp Lys Gly Tyr Met Leu Gly Arg Cys Val |
| JH122 | Tyr Thr Arg Gly Trp Lys Ala Arg Leu Leu Trp Leu Ile |

*Figure 7*

SEQUENCE LISTING (1) GENERAL INFORMATION:

(iii) NUMBER OF SEQUENCES: 132

(2) INFORMATION FOR SEQ ID NO: 1:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 1:

Leu Leu Leu Leu Gly Ala Gly Glu Ser Gly
1               5                   10

(2) INFORMATION FOR SEQ ID NO: 2:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 2:

Gly Ser Gly Glu Ser Gly Asp Ser Thr
1               5

(2) INFORMATION FOR SEQ ID NO: 3:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 3:

Leu Ile His Glu Asp Ile Ala Lys Ala
1               5

(2) INFORMATION FOR SEQ ID NO: 4:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 4:

Ser Leu Leu Trp Leu Thr Cys Arg Pro Trp Glu Ala Met
1               5                   10

(2) INFORMATION FOR SEQ ID NO: 5:

(i) SEQUENCE CHARACTERISTICS:

(A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 5:

GTTAAGAACC ATATACTAGT ATCAAAAATG TCTG                                34

(2) INFORMATION FOR SEQ ID NO: 6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

TGATCAAAAT TTACTAGTTT GAAAAAGTAA TTTCG                               35

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

GGCAAAATAC TAGTAAAATT TTCATGTC                                       28

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

GGCCCTTAAC ACACTAGTGT CGCATTATAT TTAC                                34

(2) INFORMATION FOR SEQ ID NO: 9:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

CTAAAGAAGA AGGGTATCT TTGCTTAAGC TCGAGATCTC GACTGATAAC AACAGTGTAG      60

(2) INFORMATION FOR SEQ ID NO: 10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

CATACACAAT ATAAAGCTTT AAAAGAATGA G                                    31

(2) INFORMATION FOR SEQ ID NO: 11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

TTAAGCGTGA GGCAGAAGCT TATCGATA                                        28

(2) INFORMATION FOR SEQ ID NO: 12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

CGCACTCCGT CTTCGAATAG CTATCTAG                                        28

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

GCTACTTAAG CGTGAGGCAG AAGCT                                           25

(2) INFORMATION FOR SEQ ID NO: 14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

CGGATGATCA NNNAGCTTCT GCCTCACGCT TAAGTAGC                             38

(2) INFORMATION FOR SEQ ID NO: 15:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

CTGGATGCGA AGACAGCTNN KNNKNNKNNK NNKNNKNNKN NKNNKNNKNN KNNKTGATCA    60

GTCTGTGACG C    71

(2) INFORMATION FOR SEQ ID NO: 16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 16:

GCGTCACAGA CTGATCA    17

(2) INFORMATION FOR SEQ ID NO: 17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 17:

TGATCAGTCT GTGACGC    17

(2) INFORMATION FOR SEQ ID NO: 18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 18:

ACTAGTCAGA CACTGCG    17

(2) INFORMATION FOR SEQ ID NO: 19:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

CCAAAATAAG TACAAAGCTT TCGAATAGAA ATGCAACCAT C    41

(2) INFORMATION FOR SEQ ID NO: 20:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 20:

GCCGCTCCAA AAGAAAAGAC CTCGAGCTCG CTTAAGTTCT GCGTACAAAA ACGTTGTTC    59

```
(2) INFORMATION FOR SEQ ID NO: 21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 21:

GGTACTCGAG TGAAAAGAAG GACAAC                                              26

(2) INFORMATION FOR SEQ ID NO: 22:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 22:

CGTACTTAAG CAATAACACA NNNGTTGTCC TTCTTTTCAC TCGAGTACC                     49

(2) INFORMATION FOR SEQ ID NO: 23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 23:

GCGTCACAGA CTGATCA                                                        17

(2) INFORMATION FOR SEQ ID NO: 24:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 24:

GCCGTCAGTA AAGCTTGGCA TTGGTTGNNS NNSNNSNNSM MSCAGCCTAT GTACTGATCA         60

GTCTGTGACG C                                                              71

(2) INFORMATION FOR SEQ ID NO: 25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 25:
```

```
TGG CAT TGG TTG CAG CTA AAA CCT GGC CAA CCA ATG TAC          39
Trp His Trp Leu Gln Leu Lys Pro Gly Gln Pro Met Tyr
 1               5                  10
```

(2) INFORMATION FOR SEQ ID NO: 26:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 26:

```
Trp His Trp Leu Gln Leu Lys Pro Gly Gln Pro Met Tyr
 1               5                  10
```

(2) INFORMATION FOR SEQ ID NO: 27:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 27:

```
TGG CAT TGG TTG CAG CTA AAA CCT GGC CAG CCT ATG TAC          39
Trp His Trp Leu Gln Leu Lys Pro Gly Gln Pro Met Tyr
 1               5                  10
```

(2) INFORMATION FOR SEQ ID NO: 28:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 28:

```
Trp His Trp Leu Gln Leu Lys Pro Gly Gln Pro Met Tyr
 1               5                  10
```

(2) INFORMATION FOR SEQ ID NO: 29:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 29:

```
TGG CAT TGG TTG TCC TTG TCG CCC GGG CAG CCT ATG TAC          39
Trp His Trp Leu Ser Leu Ser Pro Gly Gln Pro Met Tyr
 1               5                  10
```

(2) INFORMATION FOR SEQ ID NO: 30:

```
    (i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 30:

Trp His Trp Leu Ser Leu Ser Pro Gly Gln Pro Met Tyr
 1               5                  10

(2) INFORMATION FOR SEQ ID NO: 31:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 31:

TGG CAT TGG TTG TCC CTG GAC GCT GGC CAG CCT ATG TAC           39
Trp His Trp Leu Ser Leu Asp Ala Gly Gln Pro Met Tyr
 1               5                  10

(2) INFORMATION FOR SEQ ID NO: 32:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 32:

Trp His Trp Leu Ser Leu Asp Ala Gly Gln Pro Met Tyr
 1               5                  10

(2) INFORMATION FOR SEQ ID NO: 33:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 33:

TGG CAT TGG TTG ACC TTG ATG GCC GGG CAG CCT ATG TAC           39
Trp His Trp Leu Thr Leu Met Ala Gly Gln Pro Met Tyr
 1               5                  10

(2) INFORMATION FOR SEQ ID NO: 34:

(i) SEQUENCE CHARACTERISTICS:
        (A) LENGTH: 13 amino acids
        (B) TYPE: amino acid
        (D) TOPOLOGY: linear (ii) MOLECULE TYPE: protein
```

(xi) SEQUENCE DESCRIPTION: SEQ ID NO: 34:

Trp His Trp Leu Thr Leu Met Ala Gly Gln Pro Met Tyr
1               5                   10

(2) INFORMATION FOR SEQ ID NO: 35:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 35:

TGG CAT TGG TTG CAG CTG TCG GCG GGC CAG CCT ATG TAC    39
Trp His Trp Leu Gln Leu Ser Ala Gly Gln Pro Met Tyr
1               5                   10

(2) INFORMATION FOR SEQ ID NO: 36:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 36:

Trp His Trp Leu Gln Leu Ser Ala Gly Gln Pro Met Tyr
1               5                   10

(2) INFORMATION FOR SEQ ID NO: 37:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 37:

TGG CAT TGG TTG AGG TTG CAG TCC GGC CAG CCT ATG TAC    39
Trp His Trp Leu Arg Leu Gln Ser Gly Gln Pro Met Tyr
1               5                   10

(2) INFORMATION FOR SEQ ID NO: 38:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 38:

Trp His Trp Leu Arg Leu Gln Ser Gly Gln Pro Met Tyr
1               5                   10

(2) INFORMATION FOR SEQ ID NO: 39:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 39:

```
TGG CAT TGG TTG CGC TTG TCC GCC GGG CAG CCT ATG TAC          39
Trp His Trp Leu Arg Leu Ser Ala Gly Gln Pro Met Tyr
 1               5                  10
```

(2) INFORMATION FOR SEQ ID NO: 40:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 40:

```
Trp His Trp Leu Arg Leu Ser Ala Gly Gln Pro Met Tyr
 1               5                  10
```

(2) INFORMATION FOR SEQ ID NO: 41:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 41:

```
TGG CAT TGG TTG TCG CTC GTC CCG GGG CAG CCT ATG TAC          39
Trp His Trp Leu Ser Leu Val Pro Gly Gln Pro Met Tyr
 1               5                  10
```

(2) INFORMATION FOR SEQ ID NO: 42:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 42:

```
Trp His Trp Leu Ser Leu Val Pro Gly Gln Pro Met Tyr
 1               5                  10
```

(2) INFORMATION FOR SEQ ID NO: 43:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
                (A) NAME/KEY: CDS
                (B) LOCATION: 1..39

(xi) SEQUENCE DESCRIPTION: SEQ ID NO: 43:

```
TGG CAT TGG TTG TCC CTG TAC CCC GGG CAG CCT ATG TAC          39
Trp His Trp Leu Ser Leu Tyr Pro Gly Gln Pro Met Tyr
 1               5                  10
```

(2) INFORMATION FOR SEQ ID NO: 44:

(i) SEQUENCE CHARACTERISTICS:
                (A) LENGTH: 13 amino acids
                (B) TYPE: amino acid
                (D) TOPOLOGY: linear (ii) MOLECULE TYPE: protein (xi) SEQUENCE DESCRIPTION: SEQ ID NO: 44:

```
Trp His Trp Leu Ser Leu Tyr Pro Gly Gln Pro Met Tyr
 1               5                  10
```

(2) INFORMATION FOR SEQ ID NO: 45:

(i) SEQUENCE CHARACTERISTICS:
                (A) LENGTH: 39 base pairs
                (B) TYPE: nucleic acid
                (C) STRANDEDNESS: single
                (D) TOPOLOGY: linear (ii) MOLECULE TYPE: other nucleic acid (ix) FEATURE:
                (A) NAME/KEY: CDS
                (B) LOCATION: 1..39

(xi) SEQUENCE DESCRIPTION: SEQ ID NO: 45:

```
TGG CAT TGG TTG CGG CTG CAG CCC GGG CAG CCT ATG TAC          39
Trp His Trp Leu Arg Leu Gln Pro Gly Gln Pro Met Tyr
 1               5                  10
```

(2) INFORMATION FOR SEQ ID NO: 46:

(i) SEQUENCE CHARACTERISTICS:
                (A) LENGTH: 13 amino acids
                (B) TYPE: amino acid
                (D) TOPOLOGY: linear (ii) MOLECULE TYPE: protein (xi) SEQUENCE DESCRIPTION: SEQ ID NO: 46:

```
Trp His Trp Leu Arg Leu Gln Pro Gly Gln Pro Met Tyr
 1               5                  10
```

(2) INFORMATION FOR SEQ ID NO: 47:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: other nucleic acid (xi) SEQUENCE DESCRIPTION: SEQ ID NO: 47:

```
CTGGATGCGA AGACTCAGCT                                        20
```

-continued (2) INFORMATION FOR SEQ ID NO: 48:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 48:

```
CGGATGATCA GTACATTGGT TGGCCAGGTT TTAGCTGCAA CCAATGCCAA GCTGAGTCTT      60

CGCATCCAG                                                             69
```

(2) INFORMATION FOR SEQ ID NO: 49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 49:

```
CTGGATGCGA AGACTCAGCT                                                 20
```

(2) INFORMATION FOR SEQ ID NO: 50:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 50:

```
GACCTACGCT TCTGAGTCGA ACCGTAACCA ACGTCGATTT TGGACCGGTT GGTTACATGA      60

CTAGTAGGC                                                             69
```

(2) INFORMATION FOR SEQ ID NO: 51:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 51:

```
TGG CAT TGG CTA CAG CTA ACG CCT GGG CAA CCA ATG TAC                   39
Trp His Trp Leu Gln Leu Thr Pro Gly Gln Pro Met Tyr
 1               5                  10
```

(2) INFORMATION FOR SEQ ID NO: 52:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 52:

Trp His Trp Leu Gln Leu Thr Pro Gly Gln Pro Met Tyr
1               5                   10

(2) INFORMATION FOR SEQ ID NO: 53:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 53:

TGG CAT TGG CTG GAG CTT ATG CCT GGC CAA CCA TTA TAC         39
Trp His Trp Leu Glu Leu Met Pro Gly Gln Pro Leu Tyr
1               5                   10

(2) INFORMATION FOR SEQ ID NO: 54:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 54:

Trp His Trp Leu Glu Leu Met Pro Gly Gln Pro Leu Tyr
1               5                   10

(2) INFORMATION FOR SEQ ID NO: 55:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 55:

TGG CAT TGG ATG GAG CTA AGA CCT GGC CAA CCA ATG TAC         39
Trp His Trp Met Glu Leu Arg Pro Gly Gln Pro Met Tyr
1               5                   10

(2) INFORMATION FOR SEQ ID NO: 56:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 56:

Trp His Trp Met Glu Leu Arg Pro Gly Gln Pro Met Tyr
1               5                   10

(2) INFORMATION FOR SEQ ID NO: 57:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 57:

```
CGTGAAGCTT AAGCGTGAGG CAGAAGCTNN KNNKNNKNNK NNKNNKNNKN NKNNKNNKNN      60

KNNKNNKTGA TCATCCG                                                    77
```

(2) INFORMATION FOR SEQ ID NO: 58:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 58:

```
CGTGAAGCTT AAGCGTGAGG CAGAAGCT                                        28
```

(2) INFORMATION FOR SEQ ID NO: 59:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 59:

```
CGGATGATCA MNNMNNMNNM NNMNNMNNMN NMNNMNNMNN MNNMNNMNNA GCTTCTG         57
```

(2) INFORMATION FOR SEQ ID NO: 60:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 60:

```
GGTACTCGAG TGAAAGAAG GACAACNNKN NKNNKNNKNN KNNKNNKNNK NNKNNKNNKT       60

GTGTTATTGC TTAAGTACG                                                  79
```

(2) INFORMATION FOR SEQ ID NO: 61:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 61:

```
GGTACTCGAG TGAAAGAAG GACAAC                                           26
```

-continued (2) INFORMATION FOR SEQ ID NO: 62:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 62:

```
CGTACTTAAG CAATAACACA MNNMNMMNNM NMMNNMNNMN NMNNMNNMNN MNNGTTGTCC        60
```

(2) INFORMATION FOR SEQ ID NO: 63:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..33

(xi) SEQUENCE DESCRIPTION: SEQ ID NO: 63:

```
TAT GCT CTG TTT GTT CAT TTT TTT GAT ATT CCG                              33
Tyr Ala Leu Phe Val His Phe Phe Asp Ile Pro
 1               5                  10
```

(2) INFORMATION FOR SEQ ID NO: 64:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 64:

```
Tyr Ala Leu Phe Val His Phe Phe Asp Ile Pro
 1               5                  10
```

(2) INFORMATION FOR SEQ ID NO: 65:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..33

(xi) SEQUENCE DESCRIPTION: SEQ ID NO: 65:

```
TTT AAG GGT CAG GTG CGT TTT GTG GTT CTT GCT                              33
Phe Lys Gly Gln Val Arg Phe Val Val Leu Ala
 1               5                  10
```

(2) INFORMATION FOR SEQ ID NO: 66:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 66:

Phe Lys Gly Gln Val Arg Phe Val Val Leu Ala
 1               5                   10

(2) INFORMATION FOR SEQ ID NO: 67:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: CDS
            (B) LOCATION: 1..33

(xi) SEQUENCE DESCRIPTION: SEQ ID NO: 67:

CTT ATG TCT CCG TCT TTT TTT TTT TTG CCT GCG                    33
Leu Met Ser Pro Ser Phe Phe Phe Leu Pro Ala
 1               5                   10

(2) INFORMATION FOR SEQ ID NO: 68:

(i) SEQUENCE CHARACTERISTICS:
            (A) LENGTH: 11 amino acids
            (B) TYPE: amino acid
            (D) TOPOLOGY: linear (ii) MOLECULE TYPE: protein (xi) SEQUENCE DESCRIPTION: SEQ ID NO: 68:

Leu Met Ser Pro Ser Phe Phe Phe Leu Pro Ala
 1               5                   10

(2) INFORMATION FOR SEQ ID NO: 69:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (xi) SEQUENCE DESCRIPTION: SEQ ID NO: 69:

Tyr Ile Ile Lys Gly Val Phe Trp Asp Pro Ala
 1               5                   10

(2) INFORMATION FOR SEQ ID NO: 70:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 70:

GGTGGGAGGG TGCTCTCTAG AAGGAAGTGT TCACC                         35

(2) INFORMATION FOR SEQ ID NO: 71:

(i) SEQUENCE CHARACTERISTICS:
            (A) LENGTH: 41 base pairs
            (B) TYPE: nucleic acid (C) STRANDEDNESS: single
        (D) TOPOLOGY: linear (ii) MOLECULE TYPE: other nucleic acid (xi) SEQUENCE DESCRIPTION: SEQ ID NO: 71:

GCCCAGGAGA CCAGACCATG GACTCCTTCA ATTATACCAC C                                 41

(2) INFORMATION FOR SEQ ID NO: 72:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 72:

CCCCTTAAGC GTGAGGCAGA AGCTACTCTG CAAAAGAAGA TC                                42

(2) INFORMATION FOR SEQ ID NO: 73:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 73:

GAAGATCTTC AGCGGCCGAG TTGCATGTC                                               29

(2) INFORMATION FOR SEQ ID NO: 74:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 74:

Tyr Thr Arg Gly Trp Lys Ala Arg Leu Leu Trp Leu Ile
1               5                   10

(2) INFORMATION FOR SEQ ID NO: 75:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 75:

Xaa Xaa Xaa Xaa Trp Lys Ala Arg Leu Leu Trp Leu Ile
1               5                   10

(2) INFORMATION FOR SEQ ID NO: 76:

(i) SEQUENCE CHARACTERISTICS:
        (A) LENGTH: 13 amino acids
        (B) TYPE: amino acid

```
            (D) TOPOLOGY: linear (ii) MOLECULE TYPE: peptide (v) FRAGMENT TYPE: internal (xi) SEQUENCE DESCRIPTION: SEQ ID NO: 76:

Tyr Thr Arg Gly Xaa Xaa Xaa Xaa Leu Leu Trp Leu Ile
1               5                   10

(2) INFORMATION FOR SEQ ID NO: 77:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 77:

Tyr Thr Arg Gly Trp Lys Ala Arg Xaa Xaa Xaa Xaa Xaa
1               5                   10

(2) INFORMATION FOR SEQ ID NO: 78:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 78:

Xaa Thr Arg Xaa Trp Lys Xaa Arg Leu Xaa Trp Leu Xaa
1               5                   10

(2) INFORMATION FOR SEQ ID NO: 79:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 79:

Xaa Thr Arg Xaa Trp Lys Xaa Arg Leu Xaa Trp Leu Xaa
1               5                   10

(2) INFORMATION FOR SEQ ID NO: 80:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 80:

Tyr Xaa Arg Gly Xaa Lys Ala Xaa Leu Leu Xaa Leu Ile
1               5                   10
```

(2) INFORMATION FOR SEQ ID NO: 81:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 81:

```
Tyr Thr Xaa Gly Trp Xaa Ala Arg Xaa Leu Trp Xaa Ile
 1               5                  10
```

(2) INFORMATION FOR SEQ ID NO: 82:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 82:

GATATATTAA GGTAGGAAAC CATGGGGTGT ACAGTGAG     38

(2) INFORMATION FOR SEQ ID NO: 83:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 83:

CGAGGCTCGA GGGAACGTAT AATTAAAGTA GTG     33

(2) INFORMATION FOR SEQ ID NO: 84:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 84:

GCGCGGTACC AAGCTTCAAT TCGAGATAAT ACCC     34

(2) INFORMATION FOR SEQ ID NO: 85:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 85:

CCCGAATCCA CCAATTTCTT TACG     24

(2) INFORMATION FOR SEQ ID NO: 86:

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 86:

GCGGCGTCGA CGCGGCCGCG TAACAGT                                        27

(2) INFORMATION FOR SEQ ID NO: 87:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 87:

CTGCTGGAGC TCCGCCTGCT GCTGCTGGGT GCTGGAG                             37

(2) INFORMATION FOR SEQ ID NO: 88:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 88:

CTGCTGGTCG ACGCGGCCGC GGGGGTTCCT TCTTAGAAGC AGC                      43

(2) INFORMATION FOR SEQ ID NO: 89:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 89:

GGGCTCGAGC CTTCTTAGAG CAGCTCGTAC                                     30

(2) INFORMATION FOR SEQ ID NO: 90:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 90:

CTGCTGGAGC TCAAGTTGCT GCTGTTGGGT GCTGGGG                             37

(2) INFORMATION FOR SEQ ID NO: 91:

(i) SEQUENCE CHARACTERISTICS:
        (A) LENGTH: 44 base pairs
        (B) TYPE: nucleic acid
```

```
        (C) STRANDEDNESS: single
        (D) TOPOLOGY: linear (ii) MOLECULE TYPE: other nucleic acid (xi) SEQUENCE DESCRIPTION: SEQ ID NO: 91:

CTGCTGGTCG ACGCGGCCGC GCCCCTCAGA AGAGGCCGCG GTCC                    44

(2) INFORMATION FOR SEQ ID NO: 92:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 92:

GGGCTCGAGC CTCAGAAGAG GCCGCAGTC                                     29

(2) INFORMATION FOR SEQ ID NO: 93:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 93:

CTGCTGGAGC TCAAGCTGCT GCTACTCGGT GCTGGAG                            37

(2) INFORMATION FOR SEQ ID NO: 94:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 94:

CTGCTGGTCG ACGCGGCCGC CACTAACATC CATGCTTCTC AATAAAGTC               49

(2) INFORMATION FOR SEQ ID NO: 95:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 95:

GGGCTCGAGC ATGCTTCTCA ATAAAGTCCA C                                  31

(2) INFORMATION FOR SEQ ID NO: 96:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
```

(xi) SEQUENCE DESCRIPTION: SEQ ID NO: 96:

GCATCCATCA ATAATCCAG                                                    19

(2) INFORMATION FOR SEQ ID NO: 97:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 97:

GAAACAATGG ATCCACTTCT TAC                                               23

(2) INFORMATION FOR SEQ ID NO: 98:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 98:

GGCGCCCGGT CTCCCATGGA AACCAACTTC TCCACT                                 36

(2) INFORMATION FOR SEQ ID NO: 99:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 99:

GGCGCCCGGT CTCCGATCCC ATTGCCTGTA ACTCAGTCTC                             40

(2) INFORMATION FOR SEQ ID NO: 100:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 100:

TCTCTGCTTT GGCTGACTTG TCGGCCTTGG GAGGCGATG                              39

(2) INFORMATION FOR SEQ ID NO: 101:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 101:

GGGCCATGGG GCCGCGGCGG TTG                                               23

(2) INFORMATION FOR SEQ ID NO: 102:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 102:

CCCGGATCCT AAGTTAACAG CTTTTTGTAT AT                                32

(2) INFORMATION FOR SEQ ID NO: 103:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO: 103:

GTT TGT CCT GCG CGT TAT GTG CTG CCT GGG CCT GTT TTG              39
Val Cys Pro Ala Arg Tyr Val Leu Pro Gly Pro Val Leu
 1               5                  10

(2) INFORMATION FOR SEQ ID NO: 104:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 104:

Val Cys Pro Ala Arg Tyr Val Leu Pro Gly Pro Val Leu
 1               5                  10

(2) INFORMATION FOR SEQ ID NO: 105:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 105:

Gln Ala Arg Lys Leu Gly Ile Gln
 1               5

(2) INFORMATION FOR SEQ ID NO: 106:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 106:

```
Asp Val Gly Gly Gln
1               5
```

(2) INFORMATION FOR SEQ ID NO: 107:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 107:

```
Asp Thr Arg Ser Trp Lys Leu Arg Leu Leu Trp Leu Ala
1               5                   10
```

(2) INFORMATION FOR SEQ ID NO: 108:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 108:

```
Xaa Xaa Xaa Xaa Xaa Thr Cys Arg Pro Trp Glu Ala Met
1               5                   10
```

(2) INFORMATION FOR SEQ ID NO: 109:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 109:

```
Ser Leu Leu Trp Leu Xaa Xaa Xaa Xaa Trp Glu Ala Met
1               5                   10
```

(2) INFORMATION FOR SEQ ID NO: 110:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 110:

```
Ser Leu Leu Trp Leu Thr Cys Arg Pro Xaa Xaa Xaa Xaa
1               5                   10
```

(2) INFORMATION FOR SEQ ID NO: 111:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 111:

```
Xaa Leu Xaa Trp Xaa Thr Xaa Arg Xaa Trp Xaa Ala Xaa
1               5                   10
```

(2) INFORMATION FOR SEQ ID NO: 112:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 112:

```
Ser Xaa Leu Xaa Leu Xaa Cys Xaa Pro Xaa Glu Xaa Met
 1               5                  10
```

(2) INFORMATION FOR SEQ ID NO: 113:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 7-19
        (D) OTHER INFORMATION: /note= "Xaa is any amino acid"

(xi) SEQUENCE DESCRIPTION: SEQ ID NO: 113:

```
Lys Arg Glu Ala Glu Ala Xaa Xaa Xaa Xaa Xaa Xaa Xaa Xaa Xaa
 1               5                  10                  15

Xaa Xaa Xaa Xaa
```

(2) INFORMATION FOR SEQ ID NO: 114:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 114:

```
CGTGAAGCTT AAGCGTGAGG CAGAAGCTNN KNNKNNKNNK NNKNNKNNKN NKNNKNNKNN        60

KNNKNNKTGA TCATCCG                                                      77
```

(2) INFORMATION FOR SEQ ID NO: 115:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 115:

```
Lys Glu Glu Gly Val Ser Leu Leu
 1               5
```

(2) INFORMATION FOR SEQ ID NO: 116:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 116:

AAGCTTAAAA GAATG                                                             15

(2) INFORMATION FOR SEQ ID NO: 117:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 117:

AAAGAAGAAG GGGTATCTTT GCTTAAGCTC GAGATCT                                     37

(2) INFORMATION FOR SEQ ID NO: 118:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 118:

AAGCTT                                                                        6

(2) INFORMATION FOR SEQ ID NO: 119:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 8-18
        (D) OTHER INFORMATION: /note= "Xaa is any amino acid"

(xi) SEQUENCE DESCRIPTION: SEQ ID NO: 119:

Ser Ser Glu Lys Lys Asp Asn Xaa Xaa Xaa Xaa Xaa Xaa Xaa Xaa Xa
  1               5                  10                  15

Xaa Xaa Cys Val Ile Ala
          20

(2) INFORMATION FOR SEQ ID NO: 120:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 120:

GGTACTCGAG TGAAAAGAAG GACAACNNKN NKNNKNNKNN KNNKNNKNNK NNKNNKNNKT            60

GTGTTATTGC TTAAGTACG                                                         79

(2) INFORMATION FOR SEQ ID NO: 121:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 121:

AGCTTTCGAA TAGAAATG                                                  18

(2) INFORMATION FOR SEQ ID NO: 122:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 122:

GCCGCTCCAA AAGAAAAGAC CTCGAGCTCG CTTAAG                         36

(2) INFORMATION FOR SEQ ID NO: 123:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 123:

Phe Leu Glu Cys Pro His Ser Gly Phe Gly Thr Cys Val
 1          5                10

(2) INFORMATION FOR SEQ ID NO: 124:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 124:

Cys Leu Arg Val Phe Leu Pro Trp His Phe Val Leu Cys
 1          5                10

(2) INFORMATION FOR SEQ ID NO: 125:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 125:

Arg Val Phe Arg Trp Cys Tyr Phe Met Ser Glu Cys Val
 1          5                10

(2) INFORMATION FOR SEQ ID NO: 126:

(i) SEQUENCE CHARACTERISTICS:
        (A) LENGTH: 13 amino acids

-continued (B) TYPE: amino acid
        (D) TOPOLOGY: linear (ii) MOLECULE TYPE: protein (xi) SEQUENCE DESCRIPTION: SEQ ID NO: 126:

Ala Tyr Arg Gly Ser Phe Lys Leu Leu Leu Ile Trp Thr
 1               5                  10

(2) INFORMATION FOR SEQ ID NO: 127:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 127:

Val Gly Trp Pro Leu Val Ala Trp Asn Leu Leu Gly Trp
 1               5                  10

(2) INFORMATION FOR SEQ ID NO: 128:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 128:

Ser Leu Ser Thr Phe Lys Cys Arg Leu Leu Trp Val Thr
 1               5                  10

(2) INFORMATION FOR SEQ ID NO: 129:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 129:

Leu Gly Ser Val Ala Arg Val Arg Leu Cys Leu Val Cys
 1               5                  10

(2) INFORMATION FOR SEQ ID NO: 130:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 130:

Gly Ile Ala Thr Asp Phe Arg Leu Cys Leu Leu Leu Cys
 1               5                  10

(2) INFORMATION FOR SEQ ID NO: 131:

(i) SEQUENCE CHARACTERISTICS:
        (A) LENGTH: 11 amino acids
        (B) TYPE: amino acid
        (D) TOPOLOGY: linear (ii) MOLECULE TYPE: protein -continued (xi) SEQUENCE DESCRIPTION: SEQ ID NO: 131:

Val Trp Lys Gly Tyr Met Leu Gly Arg Cys Val
 1               5                  10

(2) INFORMATION FOR SEQ ID NO: 132:

(i) SEQUENCE CHARACTERISTICS:
       (A) LENGTH: 13 amino acids
       (B) TYPE: amino acid
       (D) TOPOLOGY: linear (ii) MOLECULE TYPE: protein (xi) SEQUENCE DESCRIPTION: SEQ ID NO: 132:

Tyr Thr Arg Gly Trp Lys Ala Arg Leu Leu Trp Leu Ile
 1               5                  10

METHODS AND COMPOSITIONS FOR IDENTIFYING RECEPTOR EFFECTORS

CROSS REFERENCE TO RELATED APPLICATIONS

This application is a continuation of application Ser. No. 09/953,354, filed on Sep. 13, 2001 now abandoned, which is a continuation of application Ser. No. 08/689,172, filed on Aug. 6, 1996, now abandoned, which is a continuation-in-part of application Ser. No. 08/582,333, filed Jan. 17, 1996, and issued as U.S. Pat. No. 6,255,059, which is a continuation-in-part of application Ser. No. 08/322,137, filed Oct. 13, 1994, and issued as U.S. Pat. No. 6,100,042, which is a continuation-in-part of application Ser. No. 08/309,313, filed Sep. 20, 1994, now abandoned, which is a continuation-in-part of application Ser. No. 08/190,328, filed Jan. 31, 1994, now abandoned, which is a continuation-in-part of application Ser. No. 08/041,431, filed Mar. 31, 1993, now abandoned. The contents of all of the aforementioned applications are hereby incoporated herein by reference.

BACKGROUND OF THE INVENTION

A common technique for cloning receptors is to use nucleic acid hybridization technology to identify receptors which are homologous to other, known receptors. For instance, originally the cloning of seven transmembrane domain G protein-coupled receptors (GCR) depended on the isolation and sequencing of the corresponding protein or the use of expression cloning techniques. However, when sequences for these receptors became available, it was apparent that there were significant sequence homologies between these receptors. This technology, since it does not require that the ligand of the receptor have been identified, has resulted in the cloning of a large number of "orphan receptors", which have no known ligand and often whose biological function is obscure. Receptors of all types comprise this large family. Known orphan receptors include the nuclear receptors COUP-TF1/EAR3, COUP-TF2/ARP1, EAR-1, EAR-2, TR-2, PPAR1, HNF-4, ERR-1, ERR-2, NGFIB/Nur77, ELP/SF-1 and MPL (Parker et al, supra, and Power et al. (1992) TIBS 13:318–323). A large number of orphan receptors have been identified in the EPH family (Hirai et al (1987) Science 238:1717–1720). HER3 and HER4 are orphan receptors in the epidermal growth factor receptor family (Plowman et al. (1993) Proc. Natl. Acad. Sci. USA 90:1746–1750). ILA is a newly identified member of the human nerve growth factor/tumor necrosis factor receptor family (Schwarz et al. (1993) Gene 134:295–298). IRRR is an orphan insulin receptor-related receptor which is a transmembrane tyrosine kinase (Shier et al. (1989) J. Biol Chem 264:14606–14608). Several orphan tyrosine kinase receptors have been found in Drosophila (Perrimon (1994) Curr. Opin. Cell Biol.6:260–266). The importance of identifying ligands for orphan receptors is clear; it opens up a wide area for research in the area of drug discovery.

One large subgroup of orphan receptors, as alluded to above, are found in the G protein coupled receptor family. Approximately. 100 such receptors have been identified by function and these mediate transmembrane signaling from external stimuli (vision, taste and smell), endocrine function (pituitary and adrenal), exocrine function (pancreas), heart rate, lipolysis, and carbohydrate metabolism. Structural and genetic similarities suggest that G protein-coupled receptor superfamily can be subclassified into five distinct groups: (i) amine receptors (serotonin, adrenergic, etc.); (ii) small peptide hormone (somatostatin, TRH, etc.); (iii) large peptide hormone (LH-CG, FSH, etc.); (iv) secretin family; and (v) odorant receptors (Buck L. and Axel, R. (1991) Cell 65:175–187), with orphan receptors apparently occurring in each of the sub-families.

Previous work describes the expression of recombinant mammalian G protein-coupled receptors as a means of studying receptor function as a means of identifying agonists and antagonists of those receptors. For example, the human muscarinic receptor (HM1) has been functionally expressed in mouse cells (Harpold et al. U.S. Pat. No. 5,401,629). The rat V1b vasopressin receptor has been found to stimulate phosphotidy.inositol hydrolysis and intracellular $Ca^{2+}$ mobilization in Chinese hamster ovary cells upon agonist stimulation (Lolait et al. (1995) Proc Natl. Acad Sci. USA 92:6783–6787). These types of ectopic expression studies have enabled researchers to study receptor signalling mechanisms and to perform mutagenisis studies which have been useful in identifying portions of receptors that are critical for ligand binding or signal transduction.

Experiments have also been undertaken to express functional G protein coupled receptors in yeast cells. For example, U.S. Pat. No. 5,482,835 to King et al. describes a transformed yeast cell which is incapable of producing a yeast G protein a subunit, but which has been engineered to produce both a mammalian G protein α-subunit and a mammalian receptor which is "coupled to" (i.e., interacts with) the aforementioned mammalian G protein α-subunit. Specifically, U.S. Pat. No. 5,482,835 reports expression of the human beta-2 adrenergic receptor (β2AR), a seven transmembrane receptor (STR), in yeast, under control of the GAL1 promoter, with the β2AR gene modified by replacing the first 63 base pairs of coding sequence with 11 base pairs of noncoding and 42 base pairs of coding sequence from the STE2 gene. (STE2 encodes the yeast α-factor receptor). The Duke researchers found that the modified β2AR was functionally integrated into the membrane, as shown by studies of the ability of isolated membranes to interact properly with various known agonists and antagonists of β2AR. The ligand binding affinity for yeast-expressed β2AR was said to be nearly identical to that observed for naturally produced β2AR.

U.S. Pat. No. 5,482,835 describes co-expression of a rat G protein α-subunit in the same cells, yeast strain 8C, which lacks the cognate yeast protein. Ligand binding resulted in G protein-mediated signal transduction. U.S. Pat. No. 5,482,835 teaches that these cells may be used in screening compounds for the ability to affect the rate of dissociation of Gα from Gβγ in a cell. For this purpose, the cell further contains a pheromone-responsive promoter (e.g. BAR1 or FUS1), linked to an indicator gene (e.g. HIS3 or LacZ). The cells are placed in multi-titer plates, and different compounds are placed in each well. The colonies are then scored for expression of the indicator gene.

SUMMARY OF THE INVENTION

The present invention relates to a rapid, reliable and effective assay for screening and identifying pharmaceutically effective compounds that specifically interact with and modulate the activity of a cellular receptor or ion channel. The subject assay enables rapid screening of large numbers of polypeptides in a library to identifying those polypeptides which agonize or antagonize receptor bioactivity. In general, the assay is characterized by the use of a library of recombinant cells, each cell of which include (i) a target receptor protein whose signal transduction activity can be modulated by interaction with an extracellular signal, the transduction activity being able to generate a detectable signal, and (ii) an expressible recombinant gene encoding an exogenous test polypeptide from a polypeptide library. By the use of a variegated gene library, the mixture of cells collectively express a variegated population of test polypeptides. In preferred embodiments, the polypeptide library includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library.

The ability of particular constituents of the peptide library to modulate the signal transduction activity of the target receptor can be scored for by detecting up or down-regulation of the detection signal. For example, second messenger generation via the receptor can be measured directly. Alternatively, the use of a reporter gene can provide a convenient readout. In any event, a statistically significant change in the detection signal can be used to facilitate isolation of those cells from the mixture which contain a nucleic acid encoding a test polypeptide which is an effector of the target receptor.

By this method, test polypeptides which induce receptor signaling can be identified. If the test polypeptide does not appear to directly induce the activity of the receptor protein, the assay may be repeated and modified by the introduction of a step in which the recombinant cell is first contacted with a known activator of the target receptor to induce the signal transdution pathways from the receptor. In one embodiment, the test polypeptide is assayed for its ability to antagonize, e.g., inhibit or block the activity of the activator. Alternatively, the assay can score for peptides from the peptide library which potentiate the induction response generated by treatment of the cell with a known activator. As used herein, an "agonist" refers to agents which either induce activation of receptor signalling pathways, e.g., such as by mimicking a ligand for the receptor, as well as agents which potentiate the sensitivity of the receptor to a ligand, e.g., lower the concentrations of ligand required to induce a particular level of receptor-dependent signalling.

In one embodiment of the present invention the reagent cells express the receptor of interest endogenously. In yet other embodiments, the cells are engineered to express a heterlogous target receptor protein. In either of these embodiments, it may be desirable to inactivate one or more endogenous genes of the host cells. For example, certain preferred embodiments in which a heterlogous receptor is provided utilize host cells in which the gene for the homologous receptor has been inactivated. Likewise, other proteins involved in transducing signals from the target receptor can be inactivated, or complemented with an ortholog or paralog from another organism, e.g., yeast G protein subunits can be complemented by mammalian G protein subunits in yeast cells also engineered to express a mammalian G protein coupled receptor. Other complementations include, for example, expression of heterologous MAP kinases or erk kinases, MEKs or MKKs (MAP kinase kinases), MEKKs (MEK kinases), ras, raf, STATs, JAKs and the like.

The receptor protein can be any receptor which interacts with an extracellular molecule (i.e. hormone, growth factor, peptide) to modulate a signal in the cell. To illustrate the receptor can be a cell surface receptor, or in other embodiments can be an intracellular receptor. In preferred embodiments, the receptor is a cell surface receptor, such as: a receptor tyrosine kinase, e.g., an EPH receptor; an ion channel; a cytokine receptor; an multisubunit immune recognition receptor, a chemokine receptor; a growth factor receptor, or a G-protein coupled receptor, such as a chemoattracttractant peptide receptor, a neuropeptide receptor, a light receptor, a neurotransmitter receptor, or a polypeptide hormone receptor.

Preferred G protein coupled receptors include α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor, fMLP-like receptor, angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, Interleukin 8 (IL-8) IL-8RA, IL-8RB, Delta Opioid receptor, Kappa Opioid receptor, mip-1/RANTES receptor, Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor receptor, antidiuretic hormone receptor, glucagon receptor, and adrenocorticotropic hormone II receptor.

Preferred EPH receptors include eph, elk, eck, sek, mek4, hek, hek2, eek, erk, tyro1, tyro4, tyroS, tyro6, tyro11, cek4, cekS, cek6, cek7, cek8, cek9, cek10, bsk, rtk1, rtk2, rtk3, myk1, myk2, ehk1, ehk2, pagliaccio, htk, erk and nuk receptors.

As set forth below, no matter which structural/function class to which the target receptor may belong, the subject assay is amenable to identifying ligands for an otherwise orphan receptor.

In those embodiments wherein the target receptor is a cell surface receptor, it will be desirable for the peptides in the library to express a signal sequence to ensure that they are processed in the appropriate secretory pathway and thus are available to interact with receptors on the cell surface.

With respect to a detection signal generated by signal transduction, certain of the preferred embodiments measure the production of second messengers to determine changes in ligand engagement by the receptor. In preferred embodiments, changes in GTP hydrolysis, calcium mobilization, or phospholipid hydrolysis can be measured.

In other preferred embodiment, the host cells harbors a reporter construct containing a reporter gene in operative linkage with one or more transcriptional regulatory elements responsive to the signal transductin activity of the receptor protein. Exemplary reporter genes include enzymes, such as luciferase, phosphatase, or β-galactosidase which can produce a spectrometrically active label, e.g., changes in color, fluorescence or luminescence, or a gene product which alters a cellular phenotype, e.g., cell growth, drug resistance or auxotrophy. In preferred embodiments: the reporter gene encodes a gene product selected from the group consisting of chloramphenicol acetyl transferase, beta-galactosidase and secreted alkaline phosphatase; the reporter gene encodes a gene product which confers a growth signal; the reporter gene encodes a gene product for growth in media containing aminotriazole or canavamne.

The reagent cells of the present invention can be derived from any eukaryotic organism. In preferred embodiments the cells are mammalian cells. In more preferred embodiments the cells are yeast cells, with cells from the genera *Saccharomyces* or *Schizosaccharomyces* being more preferred. However, cells from amphibia (such as *xenopus*), avian or insect sources are also contemplated. The host cells can derived from primary cells, or transformed and/or immortalized cell lines.

In another aspect, the present invention provides

BRIEF DESCRIPTION OF THE DRAWINGS

FIG. 1. Structures of pAAH5 and pRS-ADC.

FIG. 2 includes the following sequences:
CGTGAAGCTTAAGCGTGAGGCAGAA GCT(NNK)$_{13}$T-GATCATCCG (SEQ ID NO: 57);
AAGCTTAAAAGAATG SEQ ID NO:116;
AAAGAAGAAGGGGTATCTTTGCTTAAGCTCGAGAT-CT (SEQ ID NO:117);
Lys Glu Glu Gly Val Ser Leu Leu (SEQ ID NO:115); and
AAGCTT (SEQ ID NO:118)

FIG. 3 includes the following sequences:
GGTACTCGAG TGAAAAGAAG GACAACNNK NNKNNKNNKN NKNNKNNKNN KNNKNNKNNK TGTGTTATTG CTTAAGTACG (SEQ ID NO:120);
AGCTTTCGAA TAGAAATG (SEQ ID NO:121) GCCGCTCCAA AAGAAAAGAC CTCGAGCTCG CTTAAG (SEQ ID NO: 122);
Ser Ser Glu Lys Lys Asp Asn Xaa Xaa Xaa Xaa Xaa Xaa Xaa Xaa Xaa Xaa Xaa Cys Val Ile Ala (SEQ ID NO: 119); and
Ala Ala Pro Lys Glu Lys Thr Ser Ser (SEQ ID NO:133).

FIG. 7. The amino acid sequence for C5a surrogate agonist peptides: 14 (SEQ ID NO: 123); JH19 (SEQ ID NO: 124); 314, JH36, JH39 (SEQ ID NO: 125); 33 (SEO ID NO: 126); 36 (SEQ ID NO: 127); 133, 134 (SEQ ID NO: 128); 137 (SEQ ID NO: 129); JH73, JH80 (SEQ ID NO: 130); JH101 (SEQ ID NO: 131); and JH122 (SEQ ID NO: 132).

DETAILED DESCRIPTION OF THE INVENTION

Figure 2:
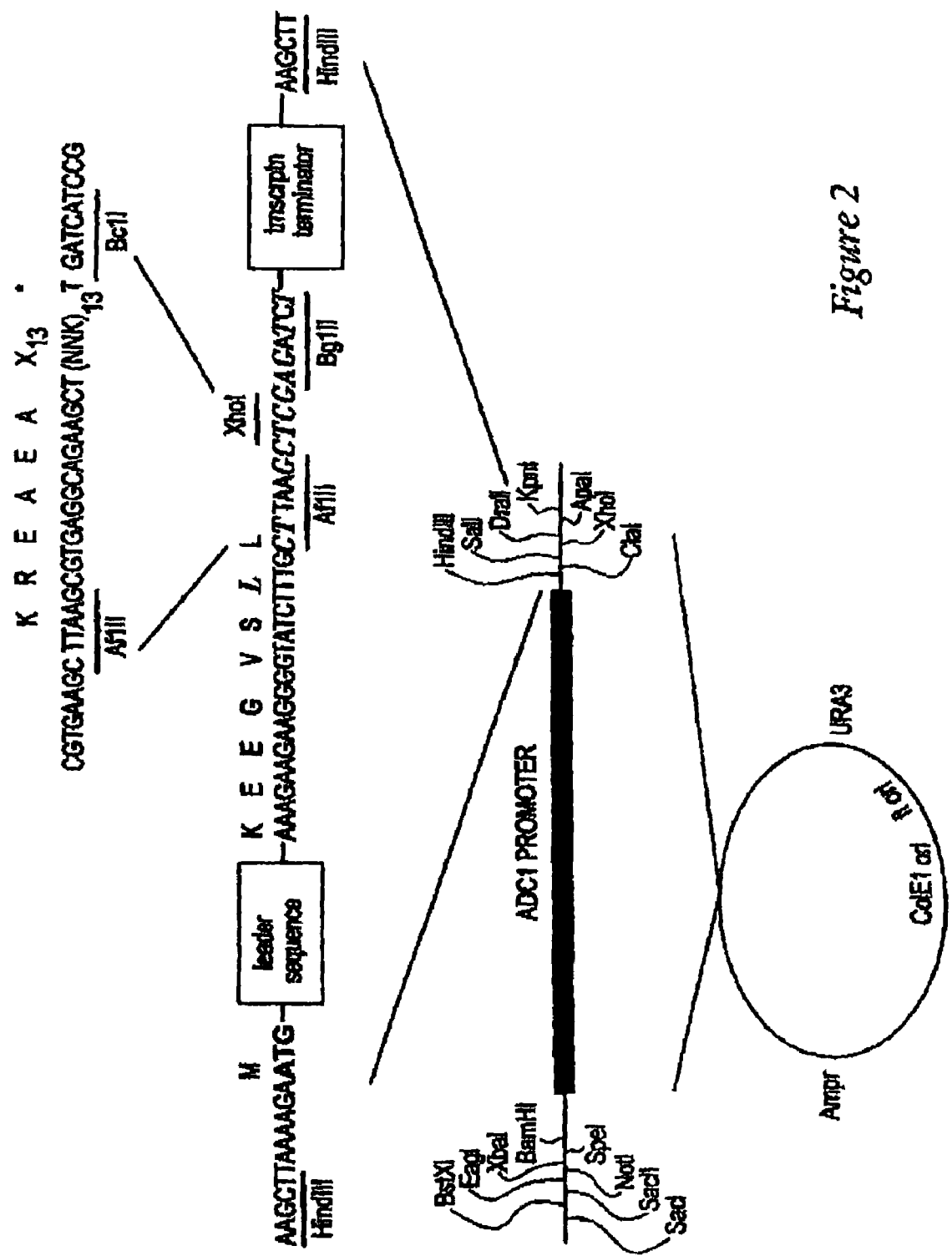
FIG. 2. Schematic diagram of the structure of the plasmid resulting from insertion of random oligonucleotides into pADC-MF alpha. This plasmid expresses random peptides in the context of the MF alpha 1 signal and leader peptide.

Proliferation, differentiation and death of eukaryotic cells are controlled by hormones, neurotransmitters, and polypeptide factors. These diffusible ligands allow cells to influence and be influenced by environmental cues. The study of receptor-ligand interaction has revealed a great deal of information about how cells respond to external stimuli, and this knowledge has led to the development of therapeutically important compounds. However, the rate at which receptors have been cloned has recently increased dramatically—existing families have been extended and new families recognized. In particular, the application of advanced cloning approaches has allowed the isolation of many receptors for which ligands are initially unknown. These are commonly referred to in the art as "orphan" receptors, and several have subsequently proved to be important pharmacological targets.

The present invention makes available a rapid, effective assay for screening and identifying pharmaceutically effective compounds that specifically interact with and modulate the activity of a cellular receptor or ion channel. The subject assay enables rapid screening of large numbers of polypeptides in a library to identifying those polypeptides which induce or antagonize receptor bioactivity.

In general, the assay is characterized by the use of a mixture of recombinant cells to sample a variegated polypeptide library for receptor agonists or antagonists. As described with greater detail below, the reagent cells express both a target receptor protein capable of transducing a detectable signal in the reagent cell, and a test polypeptide for which interaction with the receptor is to be ascertained. Collectively, a culture of such reagent cells will provide a variegated library of potential receptor effectors and those members of the library which either agonize or antagonize the receptor function can be selected and identified by sequence.

One salient feature of the subject assay is the enhanced sensitivity resulting from expression of the test polypeptide in a cell which also serves as a reporter for the desired receptor-ligand interaction. To illustrate, where the detectable signal resulting from receptor engagement by an agonist provides a growth signal or drug resistance, individual cells expressing polypeptides which agonize receptor function can be amplified and isolated from a library culture.

Accordingly, the present invention provides a convenient format for discovering drugs which can be useful to modulate cellular function, as well as to understand the pharmacology of compounds that specifically interact with cellular receptors or ion channels. Moreover, the subject assay is particularly amenable to identifying ligands, natural or artificial, for orphan receptors.

Before further description of the invention, certain terms employed in the specification, examples and appended claims are, for convenience, collected here.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express the reporter gene construct, receptor or test polypeptide.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, "heterologous DNA" or "heterologous nucleic acid" include DNA that does not occur naturally as part of the genome in which it is present or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes test polypeptides, receptors, reporter genes, transcriptional and translational regulatory sequences, selectable or traceable marker proteins, such as a protein that confers drug resistance.

As used herein, "cell surface receptor" refers to molecules that occur on the surface of cells, interact with the extracellular environment, and transmit or transduce the information regarding the environment intracellularly in a manner that ultimately modulates transcription of specific promoters, resulting in transcription of specific genes.

As used herein, "extracellular signals" include a molecule or a change in the environment that is transduced intracellularly via cell surface proteins that interact, directly or indirectly, with the signal. An extracellular signal or effector molecule includes any compound or substance that in some manner specifically alters the activity of a cell surface protein. Examples of such signals include, but are not limited to, molecules such as acetylcholine, growth factors and hormones, that bind to cell surface and/or intracellular receptors and ion channels and modulate the activity of such receptors and channels.

As used herein, "extracellular signals" also include as yet unidentified substances that modulate the activity of a cellular receptor, and thereby influence intracellular functions. Such extracellular signals are potential pharmacological agents that may be used to treat specific diseases by modulating the activity of specific cell surface receptors.

"Orphan receptors" is a designation given to a receptors for which no specific natural ligand has been described.

As used herein, a "reporter gene construct" is a nucleic acid that includes a "reporter gene" operatively linked to a transcriptional regulatory sequences. Transcription of the reporter gene is controlled by these sequences. The activity of at least one or more of these control sequences is directly or indirectly regulated by the target receptor protein. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences are recognized by effector molecules, including those that are specifically induced by interaction of an extracellular signal with the target receptor. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional regulatory elements or sequences. In addition, the construct may include sequences of nucleotides that alter translation of the resulting mRNA, thereby altering the amount of reporter gene product.

"Signal transduction" is the processing of chemical signals from the cellular environment through the cell membrane, and may occur through one or more of several mechanisms, such as phosphorylation, activation of ion channels, effector enzyme activation via guanine nucleotide binding protein intermediates, formation of inositol phosphate, activation of adenylyl cyclase, and/or direct activation (or inhibition) of a transcriptional factor.

The term "modulation of a signal transduction activity of a receptor protein" in its various grammatical forms, as used herein, designates induction and/or potentiation, as well as inhibition of one or more signal transduction pathways downstream of a receptor.

Agonists and antagonists are "receptor effector" molecules that modulate signal transduction via a receptor. Receptor effector molecules are capable of binding to the receptor, though not necessarily at the binding site of the natural ligand. Receptor effectors can modulate signal transduction when used alone, i.e. can be surrogate ligands, or can alter signal transduction in the presence of the natural ligand, either to enhance or inhibit signaling by the natural ligand. For example, "antagonists" are molecules that block or decrease the signal transduction activity of receptor, e.g., they can competitively, noncompetitively, and/or allosterically inhibit signal transduction from the receptor, whereas "agonists" potentiate, induce or otherwise enhance the signal transduction activity of a receptor. The terms "receptor activator" and "surrogate ligand" refer to an agonist which induces signal transduction from a receptor.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

Typically, "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

The term "autocrine cell", as used herein, refers to a cell which produces a substance which can stimulate a receptor located on or within the same cell as produces the substance. For example, wild-type yeast α and a cells are not autocrine. However, a yeast cell which produces both α-factor and α-factor receptor, or both a-factor and a-factor receptor, in functional form, is autocrine. By extension, cells which produce a peptide which is being screened for the ability to activate a receptor (e.g., by activating a G protein-coupled receptor) express the receptor are called "autocrine cells", though it might be more precise to call them "putative autocrine cells". Of course, in a library of such cells, in which a multitude of different peptides are produced, it is likely that one or more of the cells will be "autocrine" in the stricter sense of the term.

The terms "protein", "polypeptide" and "peptide" are used interchangeably herein.

I. Overview of Assay

As set out above, the present invention relates to methods for identifying effectors of a receptor protein or complex thereof. In general, the assay is characterized by the use of a library of recombinant cells, each cell of which include (i) a target receptor protein whose signal transduction activity can be modulated by interaction with an extracellular signal, the transduction activity being able to generate a detectable signal, and (ii) an expressible recombinant gene encoding an exogenous test polypeptide from a polypeptide library. By the use of a variegated gene library, the mixture of cells collectively express a variegated population of test polypeptides.

The ability of particular constituents of the peptide library to modulate the signal transduction activity of the target receptor can be scored for by detecting up or down-regulation of the detection signal. For example, second messenger generation (e.g. GTPase activity, phospholipid hydrolysis, or protein phosphorylation) via the receptor can be measured directly. Alternatively, the use of a reporter gene can provide a convenient readout. In any event, a statistically significant change in the detection signal can be used to facilitate isolation of those cells from the mixture which contain a nucleic acid encoding a test polypeptide which is an effector of the target receptor.

By this method, test polypeptides which induce the receptor's signaling can be screened. If the test polypeptide does not appear to induce the activity of the receptor protein, the assay may be repeated and modified by the introduction of a step in which the recombinant cell is first contacted with a known activator of the target receptor to induce signal transduction from the receptor, and the test polypeptide is assayed for its ability to inhibit the activity of the receptor, e.g., to identify receptor antagonists. In yet other embodiments, the peptide library can be screened for members which potentiate the response to a known activator of the receptor. In this respect, surrogate ligands identified by the present assay for orphan receptors can be used as the exogenous activator, and further peptide libraries screened for members which potentiate or inhibit the activating peptide. Alternatively, the surrogate ligand can be used to screen exogenous compound libraries (peptide and non-peptide) which, by modulating the activity of the identified surrogate, will presumably also similarly effect the native ligand's effect on the target receptor. In such embodiments, the surrogate ligand can be applied to the cells, though is preferably produced by the reagent cell, thereby providing an autocrine cell.

In developing the recombinant cells assays, it was recognized that a frequent result of receptor-mediated responses to extracellular signals was the transcriptional activation or inactivation of specific genes after exposure of the cognate receptor to an extracellular signal that induces such activity. Thus, transcription of genes controlled by receptor-responsive transcriptional elements often reflects the activity of the surface protein by virtue of transduction of an intracellular signal.

To illustrate, the intracellular signal that is transduced can be initiated by the specific interaction of an extracellular signal, particularly a ligand, with a cell surface receptor on the cell. This interaction sets in motion a cascade of intracellular events, the ultimate consequence of which is a rapid and detectable change in the transcription or translation of a gene. By selecting transcriptional regulatory sequences that are responsive to the transduced intracellular signals and operatively linking the selected promoters to reporter genes, whose transcription, translation or ultimate activity is readily detectable and measurable, the transcription based assay provides a rapid indication of whether a specific receptor or ion channel interacts with a test peptide in any way that influences intracellular transduction. Expression of the reporter gene, thus, provides a valuable screening tool for the development of compounds that act as agonists or antagonists of a cell receptor or ion channel.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on receptor signaling. Typically, the reporter gene construct will include a reporter gene in operative linkage with one or more transcriptional regulatory elements responsive to the signal transduction activity of the target receptor, with the level of expression of the reporter gene providing the receptor-dependent detection signal. The amount of transcription from the reporter gene may be measured using any method known to those of skill in the art to be suitable. For example, specific mRNA expression may be detected using Northern blots or specific protein product may be identified by a characteristic stain or an intrinsic activity.

In preferred embodiments, the gene product of the reporter is detected by an intrinsic activity associated with that product. For instance, the reporter gene may encode a gene product that, by enzymatic activity, gives rise to a detection signal based on color, fluorescence, or luminescence.

The amount of expression from the reporter gene is then compared to the amount of expression in either the same cell in the absence of the test compound or it may be compared with the amount of transcription in a substantially identical cell that lacks the specific receptors. A control cell may be derived from the same cells from which the recombinant cell was prepared but which had not been modified by introduction of heterologous DNA, e.g., the encoding the test polypeptide. Alternatively, it may be a cell in which the specific receptors are removed. Any statistically or otherwise significant difference in the amount of transcription indicates that the test polypeptide has in some manner altered the activity of the specific receptor.

In other preferred embodiments, the reporter or marker gene provides a selection method such that cells in which the peptide is a ligand for the receptor have a growth advantage. For example the reporter could enhance cell viability, relieve a cell nutritional requirement, and/or provide resistance to a drug.

With respect to the target receptor, it may be endogenously expressed by the host cell, or it may be expressed from a heterologous gene that has been introduced into the cell. Methods for introducing heterologous DNA into eukaryotic cells are of course well known in the art and any such method may be used. In addition, DNA encoding various receptor proteins is known to those of skill in the art or it may be cloned by any method known to those of skill in the art. In certain embodiments, such as when an exogenous receptor is expressed, it may be desirable to inactivate, such as by deletion, a homologous receptor present in the cell.

The subject assay is useful for identifying polypeptides that interact with any receptor protein whose activity ultimately induces a signal transduction cascade in the host cell which can be exploited to produce a detectable signal. In particular, the assays can be used to test functional ligand-receptor or ligand-ion channel interactions for cell surface-localized receptors and channels, and also for cytoplasmic and nuclear receptors. As described in more detail below, the subject assay can be used to identify effectors of, for example, G protein-coupled receptors, receptor tyrosine kinases, cytokine receptors, and ion channels, as well as steroid hormone receptors. In preferred embodiments the method described herein is used for identifying ligands for "orphan receptors" for which no ligand is known.

In embodiments in which cell surface receptors are the assay targets, it will be desirable for each of the peptides of the peptide library to include a signal sequence for secretion, e.g., which will ensure appropriate transport of the peptide to the endoplasmic reticulum, the golgi, and ultimately to the cell surface so that it is able to interact with cell surface receptors. In the case of yeast cells, the signal sequence will transport peptides to the periplasmic space.

Any transfectable cell that can express the desired cell surface protein in a manner such the protein functions to intracellularly transduce an extracellular signal may be used. The cells may be selected such that they endogenously express the target receptor protein or may be genetically engineered to do so.

The preparation of cells which express the orphan FPRL1 receptor, a peptide library, and a reporter gene expression construct, are described. These cells have been used to identify a novel ligand for this receptor. The cells for the identification of receptor ligands and in drug screening assays to discover agents capable of modulating receptor activity.

Any cell surface protein that is known to those of skill in the art or that may be identified by those of skill in the art may used in the assay. The cell surface protein may endogenously expressed on the selected cell or it may be expressed from cloned DNA.

II. Host Cells

Suitable host cells for generating the subject assay include prokaryotes, yeast, or higher eukaryotic cells, especially mammalian cells. Prokaryotes include gram negative or gram positive organisms. Examples of suitable mammalian host cell lines include the COS-7 line of monkey kidney cells (ATCC CRL 1651) (Gluzman (1981) Cell 23:175) CV-1 cells (ATCC CCL 70), L cells, C127, 3T3, Chinese hamster ovary (CHO), HeLa and BHK cell lines.

If yeast cells are used, the yeast may be of any species which are cultivable and in which an exogenous receptor can be made to engage the appropriate signal transduction machinery of the host cell. Suitable species include *Kluyverei lactis, Schizosaccharomyces pombe,* and *Ustilaqo maydis; Saccharomyces cerevisiae* is preferred. Other yeast which can be used in practicing the present invention are *Neurospora crassa, Aspergillus niger, Aspergillus idulans, Pichia pastoris, Candida tropicalis,* and *Hansenula polymorpha*. The term "yeast", as used herein, includes not only yeast in a strictly taxonomic sense, i.e., unicellular organisms, but also yeast-like multicellular fungi or filamentous fungi.

The choice of appropriate host cell will also be influenced by the choice of detection signal. For instance, reporter constructs, as described below, can provide a selectable or screenable trait upon transcriptional activation (or inactivation) in response to a signal transduction pathway coupled to the target receptor. The reporter gene may be an unmodified gene already in the host cell pathway, such as the genes responsible for growth arrest in yeast. It may be a host cell gene that has been operably linked to a "receptor-responsive" promoter. Alternatively, it may be a heterologous gene that has been so linked. Suitable genes and promoters are discussed below. In other embodiments, second messenger generation can be measured directly in the detection step, such as mobilization of intracellular calcium or phospholipid metabolism are quantitated. Accordingly, it will be understood that to achieve selection or screening, the host cell must have an appropriate phenotype. For example, introducing a pheromone-responsive chimeric HIS3 gene into a yeast that has a wild-type HIS3 gene would frustrate genetic selection. Thus, to achieve nutritional selection, an auxotrophic strain is wanted.

To further illustrate, in a preferred embodiment of the subject assay using a yeast host cell, the yeast cells possess one or more of the following characteristics: (a) the endogenous FUS1 gene has been inactivated; (b) the endogenous SST2 gene, and/or other genes involve in desensitization, has been inactivated; (c) if there is a homologous, endogenous receptor gene it has been inactivated; and (d) if the yeast produces an endogenous ligand to the exogenous receptor, the genes encoding for the ligand been inactivated.

Other complementations for use in the subject assay can be constructed without any undue experimentation. Indeed, many yeast genetic complementation with mammalian signal transduction proteins have been described in the art. For example, Mosteller et al. (1994) Mol Cell Biol 14:1104–12 demonstrates that human Ras proteins can complement loss of ras mutations in *S. cerevisiae*. Moreover, Toda et al. (1986) Princess Takamatsu Symp 17: 253–60 have shown that human ras proteins can complement the loss of RAS1 and RAS2 proteins in yeast, and hence are functionally homologous. Both human and yeast RAS proteins can stimulate the magnesium and guanine nucleotide-dependent adenylate cyclase activity present in yeast membranes. Ballester et al. (1989) Cell 59: 681–6 describe a vector to express the mammalian GAP protein in the yeast *S. cerevisiae*. When expressed in yeast, GAP inhibits the function of the human ras protein, and complements the loss of IRA1. IRA1 is a yeast gene that encodes a protein with homology to GAP and acts upstream of RAS. Mammalian GAP can therefore function in yeast and interact with yeast RAS. Wei et al. (1994) Gene 151: 279–84 describes that a human Ras-specific guanine nucleotide-exchange factor, Cdc25GEF, can complement the loss of CDC25 function in *S. cerevisiae*. Martegani et al. (1992) EMBO J 11: 2151–7 describe the cloning by functional complementation of a mouse cDNA encoding a homolog of CDC25, a *Saccharomyces cerevisiae* RAS activator. Vojtek et al. (1993) J Cell Sci 105: 777–85 and Matviw et al. (1992) Mol Cell Biol 12: 5033–40 describe how a mouse CAP protein, e.g., an adenylyl cyclase associated protein associated with ras-mediated signal transduction, can complements defects in *S. cerevisiae*. Papasavvas et al. (1992) Biochem Biophys Res Commun 184:1378–85 also suggest that inactivated yeast adenyl cyclase can be complemented by a mammalian adenyl cyclase gene. Hughes et al. (1993) Nature 364: 349–52 describe the complementation of byr1 in fission yeast by mammalian MAP kinase kinase (MEK). Parissenti et al. (1993) Mol Cell Endocrinol 98: 9–16 describes the reconstitution of bovine protein kinase C (PKC) in yeast. The $Ca(2+)-$ and phospholipid-dependent Ser/Thr kinase PKC plays important roles in the transduction of cellular signals in mammalian cells. Marcus et al. (1995) PNAS 92: 6180–4 suggests the complementation of shk1 null mutations in *S. pombe* by the either the structurally related *S. cerevisiae* Ste20 or mammalian p65PAK protein kinases.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

"Complementation", with respect to genes of the host cell, means that at least partial function of inactivated gene of the host cell is supplied by an exogenous nucleic acid. For instance, yeast cells can be "mammalianized", and even "humanized", by complementation of receptor and signal transduction proteins with mammalian homologs. To illustrate, inactivation of a yeast Byr2/Ste11 gene can be complemented by expression of a human MEKK gene.

III. Expression Systems

Ligating a polynucleotide coding sequence into a gene construct, such as an expression vector, and transforming or transfecting into hosts, either eukaryotic (yeast, avian, insect or mammalian) or prokaryotic (bacterial cells), are standard procedures used in producing other well-known proteins, including sequences encoding exogenous receptor and peptide libraries. Similar procedures, or modifications thereof, can be employed to prepare recombinant reagent cells of the present invention by tissue-culture technology in accord with the subject invention.

In general, it will be desirable that the vector be capable of replication in the host cell. It may be a DNA which is integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (*Cloning Vectors: A Laboratory Manual*, Elsevier, N.Y., 1985). Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTh2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

The transcriptional and translational control sequences in expression vectors to be used in transforming mammalian cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al.(1978) *Nature* 273:111) Smaller or larger SV40 fragments may also be used, provided the approximately 250 bp sequence extending from the Hind III site toward the Bgl I site located in the viral origin of replication is included. Exemplary vectors can be constructed as disclosed by Okayama and Berg (1983, *Mol. Cell Biol.*3:280). A useful system for stable high level expression of mammalian receptor cDNAs in C127 murine mammary epithelial cells can be constructed substantially as described by Cosman et al (1986, *Mol Immunol.*23:935). Other expression vectors for use in mammalian host cells are derived from retroviruses.

In other embodiments, the use of viral transfection can provide stably integrated copies of the expression construct. In particular, the use of retroviral, adenoviral or adeno-associated viral vectors is contemplated as a means for providing a stably transfected cell line which expresses an exogenous receptor, and/or a polypeptide library.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. Moreover, if yeast are used as a host cell, it will be understood that the expression of a gene in a yeast cell requires a promoter which is functional in yeast. Suitable promoters include the promoters for metallothionein, 3-phosphoglycerate kinase (Hitzeman et al., *J. Biol.Chem.* 255, 2073 (1980) or other glycolytic enzymes (Hess et al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 are of particular interest.

In some instances, it may be desirable to derive the host cell using insect cells. In such embodiments, recombinant polypeptides can be expressed by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Libraries of random peptides or cDNA fragments may be expressed in a multiplicity of ways, including as portions of chimeric proteins. As described below, where secretion of the peptide library is desired, the peptide library can be engineered for secretion or transport to the extracellular space via the yeast pheromone system In constructing suitable expression plasmids, the termination sequences associated with these genes, or with other genes which are efficiently expressed in yeast, may also be ligated into the expression vector 3' of the heterologous coding sequences to provide polyadenylation and termination of the mRNA.

IV. Periplasmic Secretion

If yeast cells are used as the host cell it will be noted that the yeast cell is bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the a-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion, or, if such secretion is provided, any particular secretion signal or transport pathway.

V. Cytokine Receptors

In one embodiment the target receptor is a cytokine receptor. Cytokines are a family of soluble mediators of cell-to-cell communication that includes interleukins, interferons, and colony-stimulating factors. The characteristic features of cytokines lie in their functional redundancy and pleiotropy. Most of the cytokine receptors that constitute distinct superfamilies do not possess intrinsic protein tyrosine kinase domains, yet receptor stimulation usually invokes rapid tyrosine phosphorylation of intracellular proteins, including the receptors themselves. Many members of the cytokine receptor superfamily acitvate the Jak protein tyrosine kinase family, with resultant phosphorylation of the STAT transcriptional activator factors. IL-2, IL-7, IL-2 and Interferon γ have all been shown to activate Jak kinases (Frank et al (1995) Proc Natl Acad Sci USA 92:7779–7783); Scharfe et al. (1995) *Blood* 86:2077–2085); (Bacon et al. (1995) *Proc Natl Acad Sci USA* 92:7307–7311); and (Sakatsume et al (1995) *J. Biol Chem* 270:17528–17534). Events downstream of Jak phosphorylation have also been elucidated. For example, exposure of T lymphocytes to IL-2 has been shown to lead to the phosphorylation of signal transducers and activators of transcription (STAT) proteins STAT1α, STAT2β, and STAT3, as well as of two STAT-related proteins, p94 and p95. The STAT proteins were found to translocate to the nucleus and to bind to a specific DNA sequence, thus suggesting a mechanism by which IL-2 may activate speicfic genes involved in immune cell function (Frank et al. supra). Jak3 is associated with the gamma chain of the IL-2, IL-4, and IL-7 cytokine receptors (Fujii et al. (1995) *Proc Natl Acad Sci* 92:5482–5486) and (Musso et al (1995) J Exp Med. 181:1425–1431). The Jak kinases have also been shown to be activated by numerous ligands that signal via cytokine receptors such as, growth hormone and erythropoietin and IL-6 (Kishimoto (1994) Stem cells Suppl 12:37–44).

Detection signals which may be scored for in the present assay, in addition to direct detection of second messangers, such as by changes in phosphorylation, includes reporter constructs which include transcriptional regulatory elements responsive to the STAT proteins. Described infra.

VI. Multisubunit Immune Recognition Receptor (MIRR).

In another embodiment the receptor is a multisubunit receptor. Receptors can be comprised of multiple proteins referred to as subunits, one category of which is referred to as a multisubunit receptor is a multisubunit immune recognition receptor (MIRR). MIRRs include receptors having multiple noncovalently associated subunits and are capable of interacting with src-family tyrosine kinases. MIRRs can include, but are not limited to, B cell antigen receptors, T cell antigen receptors, Fc receptors and CD22. One example of an MIRR is an antigen receptor on the surface of a B cell. To further illustrate, the MIRR on the surface of a B cell comprises membrane-bound immunoglobulin (mIg) associated with the subunits Ig-α and Ig-β or Ig-γ, which forms a complex capable of regulating B cell function when bound by antigen. An antigen receptor can be functionally linked to an amplifier molecule in a manner such that the amplifier molecule is capable of regulating gene transcription.

Src-family tyrosine kinases are enzymes capable of phosphorylating tyrosine residues of a target molecule. Typically, a src-family tyrosine kinase contains one or more binding domains and a kinase domain. A binding domain of a src-family tyrosine kinase is capable of binding to a target molecule and a kinase domain is capable of phosphorylating a target molecule bound to the kinase. Members of the src family of tyrosine kinases are characterized by an N-terminal unique region followed by three regions that contain different degrees of homology among all the members of the family. These three regions are referred to as src homology region 1 (SH1), src homology region 2 (SH2) and src homology region 3 (SH3). Both the SH2 and SH3 domains are believed to have protein association functions important for the formation of signal transduction complexes. The amino acid sequence of an N-terminal unique region, varies between each src-family tyrosine kinase. An N-terminal unique region can be at least about the first 40 amino acid residues of the N-terminal of a src-family tyrosine kinase.

Syk-family kinases are enzymes capable of phosphorylating tyrosine residues of a target molecule. Typically, a syk-family kinase contains one or more binding domains and a kinase domain. A binding domain of a syk-family tyrosine kinase is capable of binding to a target molecule and a kinase domain is capable of phosphorylating a target molecule bound to the kinase. Members of the syk-family of tyrosine kinases are characterized by two SH2 domains for protein association function and a tyrosine kinase domain.

A primary target molecule is capable of further extending a signal transduction pathway by modifying a second messenger molecule. Primary target molecules can include, but are not limited to, phosphatidylinositol 3-kinase (PI-3K), $P21^{ras}$GAPase-activating. protein and associated P190 and P62 protein, phospholipases such as PLCγ1 and PLCγ2, MAP kinase, Shc and VAV. A primary target molecule is capable of producing second messenger molecule which is capable of further amplifying a transduced signal. Second messenger molecules include, but are not limited to diacylglycerol and inositol 1,4,5-triphosphate (IP3). Second messenger molecules are capable of initiating physiological events which can lead to alterations in gene transcription. For example, production of IP3 can result in release of intracellular calcium, which can then lead to activation of calmodulin kinase II, which can then lead to serine phosphorylation of a DNA binding protein referred to as ets-1 proto-onco-protein. Diacylglycerol is capable of activating the signal transduction protein, protein kinase C which affects the activity of the API DNA binding protein complex. Signal transduction pathways can lead to transcriptional activation of genes such as c-fos, egr-1, and c-myc.

Shc can be thought of as an adaptor molecule. An adaptor molecule comprises a protein that enables two other proteins to form a complex (e.g., a three molecule complex). Shc protein enables a complex to form which includes Grb2 and SOS. Shc comprises an SH2 domain that is capable of associating with the SH2 domain of Grb2.

Molecules of a signal transduction pathway can associate with one another using recognition sequences. Recognition sequences enable specific binding between two molecules. Recognition sequences can vary depending upon the structure of the molecules that are associating with one another. A molecule can have one or more recognition sequences, and as such can associate with one or more different molecules.

Signal transduction pathways for MIRR complexes are capable of regulating the biological functions of a cell. Such functions can include, but are not limited to the ability of a cell to grow, to differentiate and to secrete cellular products. MIRR-induced signal transduction pathways can regulate the biological functions of specific types of cells involved in particular responses by an animal, such as immune responses, inflammatory responses and allergic responses. Cells involved in an immune response can include, for example, B cells, T cells, macrophages, dendritic cells, natural killer cells and plasma cells. Cells involved in inflammatory responses can include, for example, basophils, mast cells, eosinophils, neutrophils and macrophages. Cells involved in allergic responses can include, for example mast cells, basophils, B cells, T cells and macrophages.

In exemplary embodiments of the subject assay, the detection signal is a second messengers, such as a phosphorylated src-like protein, includes reporter constructs which include transcriptional regulatory elements such as serum response element (SRE), 12-O-tetradecanoyl-phorbol-13-acetate response element, cyclic AMP response element, c-fos promoter, or a CREB-responsive element.

VII. Nuclear Receptors.

In another embodiment, the target receptor is a nuclear receptor. The nuclear receptors may be viewed as ligand-dependent transcription factors. These receptors provide a direct link between extracellular signals, mainly hormones, and transcriptional responses. Their transcriptional activation function is regulated by endogenous small molecules, such as steroid hormones, vitamin D, ecdysone, retinoic acids and thyroid hormones, which pass readily through the plasma membrane and bind their receptors inside the cell (Laudet and Adelmant (1995) *Current Biology* 5:124). The majority of these receptors appear to contain three domains: a variable amino terminal domain; a highly conserved, DNA-binding domain and a moderately conserved, carboxyl-terminal ligand-binding domain (Power et al. (1993) *Curr. Opin. Cell Biol.* 5:499–504). Examples include the estrogen, progesterone, androgen, thyroid hormone and mineralocorticoid receptors. In addition to the known steroid receptors, at least 40 orphan members of this superfamily have been identified. (Laudet et al., (1992) *EMBO J.* 11:1003–1013). There are at least four groups of orphan nuclear receptors represented by NGF1, FTZ-F1, Rev-erbs, and RARs, which are by evolutionary standards, only distantly related to each other (Laudet et al. supra). While the steroid hormone receptors bind exclusively as homodimers to a palindrome of their hormone responsive element other nuclear receptors bind as heterodimers. Interestingly, some orphan receptors bind as monomers to similar response elements and require for their function a specific motif that is rich in basic amino-acid residues and is located corboxy-terminal to the DNA-binding domain (Laudet and Adelmant supra.)

In preferred embodiments, the subject assay is derived to utilize a hormone-dependent reporter construct for selection.

For instance, glucocorticoid response elements (GREs) and thyroid receptor enhancer-like DNA sequences (TREs) can be used to drive expression of reporter construct in response to hormone binding to hormone receptors. GRE's are enhancer-like DNA sequences that confer glucocorticoid responsiveness via interaction with the glucocorticoid receptor. See Payvar, et al. (1983) Cell 35:381 and Schiedereit et al. (1983) Nature 304:749. TRE's are similar to GRE's except that they confer thyroid hormone responsiveness via interaction with thyroid hormone receptor. Turning now to the interaction of hormones and receptors, it is known that a steroid or thyroid hormone enters cells by facilitated diffusion and binds to its specific receptor protein, initiating an allosteric alteration of the protein. As a result of this alteration, the hormone/receptor complex is capable of binding to certain specific sites on transcriptional regulatory sequence with high affinity.

It is also known that many of the primary effects of steroid and thyroid hormones involve increased transcription of a subset of genes in specific cell types. Moreover, there is evidence that activation of transcription (and, consequently, increased expression) of genes which are responsive to steroid and thyroid hormones (through interaction of chromatin with hormone receptor/hormone complex) is effected through binding of the complex to enhancers associated with the genes.

In any case, a number of steroid hormone and thyroid hormone responsive transcriptional control units, some of which have been shown to include enhancers, have been identified. These include the mouse mammary tumor virus 5'-long terminal repeat (MMTV LTR), responsive to glucocorticoid, aldosterone and androgen hormones; the transcriptional control units for mammalian growth hormone genes, responsive to glucocorticoids, estrogens, and thyroid hormones; the transcriptional control units for mammalian prolactin genes and progesterone receptor genes, responsive to estrogens; the transcriptional control units for avian ovalbumin genes, responsive to progesterones; mammalian metallothionein gene transcriptional control units, responsive to glucocorticoids; and mammalian hepatic alpha 2u-globulin gene transcriptional control units, responsive to androgens, estrogens, thyroid hormones and glucocorticoids. Such steroid hormone and thyroid hormone responsive transcriptional control units can be used to generate reporter constructs which are sensitive to agonists and antagonists of the steroid hormone and/or thyroid hormone receptors. See, for example, U.S. Pat. Nos. 5,298,429 and 5,071,773, both to Evans, et. al. Moreover, the art describes the functional expression of such receptors in yeast. See also for example, Caplan et al. (1995) J Biol Chem 270:5251–7; and Baniahmad et al. (1995) Mol Endocrinol 9: 34–43.

VIII. Receptor tyrosine kinases.

In still another embodiment, the target receptor is a receptor tyrosine kinase. The receptor tyrosine kinases can be divided into five subgroups on the basis of structural similarities in their extracellular domains and the organization of the tyrosine kinase catalytic region in their cytoplasmic domains. Sub-groups I (epidermal growth factor (EGF) receptor-like), II (insulin receptor-like) and the eph/eck family contain cysteine-rich sequences (Hirai et al., (1987) Science 238:1717–1720 and Lindberg and. Hunter, (1990) Mol. Cell. Biol. 10:6316–6324). The functional domains of the kinase region of these three classes of receptor tyrosine kinases are encoded as a contiguous sequence (Hanks et al. (1988) Science 241:42–52). Subgroups III (platelet-derived growth factor (PDGF) receptor-like) and IV (the fibro-blast growth factor (FGF) receptors) are characterized as having immunoglobulin (Ig)-like folds in their extracellular domains, as well as having their kinase domains divided in two parts by a variable stretch of unrelated amino acids (Yanden and Ullrich (1988) supra and Hanks et al. (1988) supra).

The family with by far the largest number of known members is the EPH family. Since the description of the prototype, the EPH receptor (Hirai et al. (1987) Science 238:1717–1720), sequences have been reported for at least ten members of this family, not counting apparently orthologous receptors found in more than one species. Additional partial sequences, and the rate at which new members are still being reported, suggest the family is even larger (Maisonpierre et al. (1993) Oncogene 8:3277–3288; Andres et al. (1994) Oncogene 9:1461–1467; Henkemeyer et al. (1994) Oncogene 9:1001–1014; Ruiz et al. (1994) Mech Dev 46:87–100; Xu et al. (1994) Development 120:287–299; Zhou et al. (1994) J Neurosci Res 37:129–143; and references in Tuzi and Gullick (1994) Br J Cancer 69:417–421). Remarkably, despite the large number of members in the EPH family, all of these molecules were identified as orphan receptors without known ligands.

The expression patterns determined for some of the EPH family receptors have implied important roles for these molecules in early vertebrate development. In particular, the timing and pattern of expression of sek, mek4 and some of the other receptors during the phase of gastrulation and early organogenesis has suggested functions for these receptors in the important cellular interactions involved in patterning the embryo at this stage (Gilardi-Hebenstreit et al. (1992) Oncogene 7:2499–2506; Nieto et al. (1992) Development 116: 1137–1150; Henkemeyer et al., supra; Ruiz et al., supra; and Xu et al., supra). Sek, for example, shows a notable early expression in the two areas of the mouse embryo that show obvious segmentation, namely the somites in the mesoderm and the rhombomeres of the hindbrain; hence the name sek, for segmentally expressed kinase (Gilardi-Hebenstreit et al., supra; Nieto et al., supra). As in Drosophila, these segmental structures of the mammalian embryo are implicated as important elements in establishing the body plan. The observation that Sek expression precedes the appearance of morphological segmentation suggests a role for sek in forming these segmental structures, or in determining segment-specific cell properties such as lineage compartmentation (Nieto et al., supra). Moreover, EPH receptors have been implicated, by their pattern of expression, in the development and maintenance of nearly every tissue in the embryonic and adult body. For instance, EPH receptors have been detected throughout the nervous system, the testes, the cartilaginous model of the skeleton, tooth primordia, the infundibular component of the pituitary, various epithelia tissues, lung, pancreas, liver and kidney tissues. Observations such as this have been indicative of important and unique roles for EPH family kinases in development and physiology, but further progress in understanding their action has been severely limited by the lack of information on their ligands.

As used herein, the terms "EPH receptor" or "EPH-type receptor" refer to a class of receptor tyrosine kinases, comprising at least eleven paralogous genes, though many more orthologs exist within this class, e.g. homologs from different species. EPH receptors, in general, are a discrete group of receptors related by homology and easily reconizable, e.g., they are typically characterized by an extracellular domain containing a characteristic spacing of cysteine residues near the N-terminus and two fibronectin type III repeats (Hirai et al. (1987) *Science* 238:1717–1720; Lindberg et al. (1990) *Mol Cell Biol* 10:6316–6324; Chan et al. (1991) *Oncogene* 6:1057–1061; Maisonpierre et al. (1993) *Oncogene* 8:3277–3288; Andres et al. (1994) *Oncogene* 9:1461–1467; Henkemeyer et al. (1994) *Oncogene* 9:1001–1014; Ruiz et al. (1994) *Mech Dev* 46:87–100; Xu et al. (1994) *Development* 120:287–299; Zhou et al. (1994) *J Neurosci Res* 37:129–143; and references in Tuzi and Gullick (1994) *Br J Cancer* 69:417–421). Exemplary EPH receptors include the eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors. The term "EPH receptor" refers to the membrane form of the receptor protein, as well as soluble extracellular fragments which retain the ability to bind the ligand of the present invention.

In exemplary embodiments, the detection signal is provided by detecting phosphorylation of intracellular proteins, e.g., MEKKs, MEKs, or Map kinases, or by the use of reporter constructs which include transcriptional regulatory elements responsive to c-fos and/or c-jun. Described infra.

IX. G Protein-Coupled Receptors.

One family of signal transduction cascades found in eukaryotic cells utilizes heterotrimeric "G proteins." Many different G proteins are known to interact with receptors. G protein signaling systems include three components: the receptor itself, a GTP-binding protein (G protein), and an intracellular target protein.

The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha ($\alpha$), beta ($\beta$) and gamma ($\gamma$) subunits, are complexed with the nucleotide guariosine diphosphate (GDP) and are in contact with receptors. When a hormone or other first messenger binds to receptor, the receptor changes conformation and this alters its interaction with the G protein. This spurs the a subunit to release GDP, and the more abundant nucleotide guanosine triphosphate (GTP), replaces it, activating the G protein. The G protein then dissociates to separate the $\alpha$ subunit from the still complexed beta and gamma subunits. Either the G$\alpha$ subunit, or the G$\beta\gamma$ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the G$\alpha$ converts the GTP to GDP, thereby inactivating itself. The inactivated G$\alpha$ may then reassociate with the G$\beta\gamma$ complex.

Hundreds, if not thousands, of receptors convey messages through heterotrimeric G proteins, of which at least 17 distinct forms have been isolated. Although the greatest variability has been seen in the $\alpha$ subunit, several different $\beta$ and $\gamma$ structures have been reported. There are, additionally, several different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) *Cell* 72, 415; Kouba et al. *FEBS Lett.* (1993) 321, 173; Birkenbach et al.(1993) *J. Virol.* 67, 2209.

The "exogenous receptors" of the present invention may be any G protein-coupled receptor which is exogenous to the cell which is to be genetically engineered for the purpose of the present invention. This receptor may be a plant or animal cell receptor. Screening for binding to plant cell receptors may be useful in the development of, e.g., herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, adrenaline, adrenaline., histamine, noradrenaline, noradrenaline, noradrenaline., tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, finlp and other formylated peptides, follitropin (fsh), fungal mating pheremones, galanin, gastric inhibitory polypeptide receptor (gip), glucagon-like peptides (glps), glucagon, gonadotropin releasing hormone (gnrh), growth hormone releasing hormone(ghrh), insect diuretic hormone, interleukin-8, leutropin (lh/hcg), met-enkephalin, opioid peptides, oxytocin, parathyroid hormone (pth) and pthrp, pituitary adenylyl cyclase activiating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Suitable examples of G-protein coupled receptors include, but are not limited to, dopaminergic, muscarinic cholinergic, a-adrenergic, b-adrenergic, opioid (including delta and mu), cannabinoid, serotoninergic, and GABAergic receptors. Preferred receptors include the 5HT family of receptors, dopamine receptors,C5a receptor and FPRL-1 receptor, cyclo-histidyl-proline-diketoplperazine receptors, melanocyte stimulating hormone release inhibiting factor receptor, and receptors for neurotensin, thyrotropin releasing hormone, calcitonin, cholecytokinin-A, neurokinin-2, histamine-3, cannabinoid, melanocortin, or adrenomodulin, neuropeptide-Y1 or galanin. Other suitable receptors are listed in the art. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed herein and others known in the art. Thus, the gene would be operably linked to a promoter functional in the cell to be engineered and to a signal sequence that also functions in the cell. For example in the case of yeast, suitable promoters include Ste2, Ste3 and gal10. Suitable signal sequences include those of Ste2, Ste3 and of other genes which encode proteins secreted by yeast cells. Preferably, when a yeast cell is used, the codons of the gene would be optimized for expression in yeast. See Hoekema et al.,(1987) *Mol. Cell. Biol.*, 7:2914–24; Sharp, et al., (1986)14:5125–43.

The homology of STRs is discussed in Dohlman et al., *Ann. Rev. Biochem.*, (1991) 60:653–88. When STRs are compared, a distinct spatial pattern of homology is discernible. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

It is conceivable that a foreign receptor which is expressed in yeast will functionally integrate into the yeast membrane, and there interact with the endogenous yeast G protein. More likely, either the receptor will need to be modified (e.g., by replacing its V-VI loop with that of the yeast STE2 or STE3 receptor), or a compatible G protein should be provided.

If the wild-type exogenous G protein-coupled receptor cannot be made functional in yeast, it may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible.

Preferably, the yeast genome is modified so that it is unable to produce the yeast receptors which are homologous to the exogenous receptors in functional form. Otherwise, a positive assay score might reflect the ability of a peptide to activate the endogenous G protein-coupled receptor, and not the receptor of interest.

A. Chemoattractant Receptors

The N-formyl peptide receptor is a classic example of a calcium mobilizing G protein-coupled receptor expressed by neutrophils and other phagocytic cells of the mammalian immune system (Snyderman et al. (1988) *In Inflammation: Basic Principles and Clinical Correlates*, pp. 309–323). N-formyl peptides of bacterial origin bind to the receptor and engage a complex activation program that results in directed cell movement, release of inflammatory granule contents, and activation of a latent NADPH oxidase which is important for the production of metabolites of molecular oxygen. This pathway initiated by receptor-ligand interaction is critical in host protection from pyogenic infections. Similar signal transduction occurs in response to the inflammatory peptides C5a and IL-8.

Two other formyl peptide receptor like (FPRL) genes have been cloned based on their ability to hybridize to a fragment of the NFPR cDNA coding sequence. These have been named FPRL1 (Murphy et al. (1992) *J. Biol Chem.* 267:7637–7643) and FPRL2 (Ye et al. (1992) *Biochem Biophys Res. Comm.* 184:582–589). FPRL2 was found to mediate calcium mobilization in mouse fibroblasts transfected with the gene and exposed to formyl peptide. In contrast, although FPRL1 was found to be 69% identical in amino acid sequence to NFPR, it did not bind prototype N-formyl peptides ligands when expressed in heterologous cell types. This lead to the hypothesis of the existence of an as yet unidentified ligand for the FPRL1 orphan receptor (Murphy et al. supra).

Using the technology described herein a ligand has been cloned for these orphan receptors.

B. G Proteins

In the case of an exogenous G-protein coupled receptor, the yeast cell must be able to produce a G protein which is activated by the exogenous receptor, and which can in turn activate the yeast effector(s). The art suggests that the endogenous yeast Gα subunit (e.g., GPA) will be often be sufficiently homologous to the "cognate" Ga subunit which is natively associated with the exogenous receptor for coupling to occur. More likely, it will be necessary to genetically engineer the yeast cell to produce a foreign Gα subunit which can properly interact with the exogenous receptor. For example, the Gα subunit of the yeast G protein may be replaced by the Gα subunit natively associated with the exogenous receptor.

Dietzel and Kuijan, (1987) *Cell*, 50:1001) demonstrated that rat Gαs functionally coupled to the yeast Gβγ complex. However, rat Gαi2 complemented only when substantially overexpressed, while Gα0 did not complement at all. Kang, et al., *Mol. Cell. Biol.*, (1990)10:2582). Consequently, with some foreign Gα subunits, it is not feasible to simply replace the yeast Gα.

If the exogenous G protein coupled receptor is not adequately coupled to yeast Gβγ by the Gα subunit natively associated with the receptor, the Gα subunit may be modified to improve coupling. These modifications often will take the form of mutations which increase the resemblance of the Gα subunit to the yeast Gα while decreasing its resemblance to the receptor-associated Gα. For example, a residue may be changed so as to become identical to the corresponding yeast Gα residue, or to at least belong to the same exchange group of that residue. After modification, the modified Gα subunit might or might not be "substantially homologous" to the foreign and/or the yeast Gα subunit.

The modifications are preferably concentrated in regions of the Gα which are likely to be involved in Gβγ binding. In some embodiments, the modifications will take the form of replacing one or more segments of the receptor-associated Gα with the corresponding yeast Gα segment(s), thereby forming a chimeric Gα subunit. (For the purpose of the appended claims, the term "segment" refers to three or more consecutive amino acids.) In other embodiments, point mutations may be sufficient.

This chimeric Gα subunit will interact with the exogenous receptor and the yeast Gβγ complex, thereby permitting signal transduction. While use of the endogenous yeast Gβγ is preferred, if a foreign or chimeric Gβγ is capable of transducing the signal to the yeast effector, it may be used instead.

C. Gα Structure

Some aspects of Gα structure are relevant to the design of modified Gα subunits. The amino terminal 66 residues of GPA1 are aligned with the cognate domains of human Gαs, Gαi2, Gαi3, Gα16 and transducin. In the GPA41Gα hybrids, the amino terminal 41 residues (derived from GPA1) are identical, end with the sequence-LEKQRDKNE- and are underlined for emphasis. All residues following the glutamate (E) residue at position 41 are contributed by the human Gα subunits, including the consensus nucleotide binding motif -GxGxxG-. Periods in the sequences indicate gaps that have been introduced to maximize alignments in this region. Codon bias is mammalian. For alignments of the entire coding regions of GPA1 with Gαs, Gαi, and GαO, Gαq and Gαz, see Dietzel and Kuijan (1987, Cell 50:573) and Lambright, et al. (1994, Nature 369:621–628). Additional sequence information is provided by Mattera, et al. (1986, FEBS Lett 206:36–41), Bray, et al. (1986, Proc. Natl. Acad. Sci USA 83:8893–8897) and Bray, et al. (1987, Proc Natl. Acad Sci USA 84:5115–5119).

The gene encoding a G protein homolog of S. cerevisiae was cloned independently by Dietzel and Kuijan (supra) (SCG1) and by Nakafiiku, et al. (1987 Proc Natl Acad Sci 84:2140–2144) (GPA1). Sequence analysis revealed a high degree of homology between the protein encoded by this gene and mammalian Ga. GPA1 encodes a protein of 472 amino acids, as compared with approximately 340–350 a.a. for most mammalian Gα subunits in four described families, Gαs, Gαi, Gαq and Gα12/13. Nevertheless, GPA1 shares overall sequence and structural homology with all Gα proteins identified to date. The highest overall homology in GPA1 is to the Gαi family (48% identity, or 65% with conservative substitutions) and the lowest is to GQS (33% identity, or 51% with conservativesubstitutions) (Nakafuku, et al., supra).

The regions of high sequence homology among Gα subunits are dispersed throughout their primary sequences, with the regions sharing the highest degree of homology mapping to sequence that comprises the guanine nucleotide binding/GTPase domain. This domain is structurally similar to the aβ fold of ras proteins and the protein synthesis elongation factor EF-Tu. This highly conserved guanine nucleotide-binding domain consists of a six-stranded β sheet surrounded by a set of five α-helices. It is within these β sheets and α helices that the highest degree of conservation is observed among all Gα proteins, including GPA1. The least sequence and structural homology is found in the intervening loops between the β sheets and α helices that define the core GTPase domain. There are a total of four "intervening loops" or "inserts" present in all Gα subunits. In the crystal structures reported to date for the GDP- and GTPγS-liganded forms of bovine rod transducin (Noel, et al. (1993) Nature 366:654–663); (Lambright, et al. (1994) Nature 369:621–628), the loop residues are found to be outside the core GTPase structure. Functional roles for these loop structures have been established in only a few instances. A direct role in coupling to phosphodiesterase-γ has been demonstrated for residues within inserts 3 and 4 of Gat (Rarick, et al. (1992) Science 256:1031–1033); (Artemyev, et al. (1992) J. Biol. Chem. 267:25067–25072), while a "GAP-like" activity has been ascribed to the largely α-helical insert 1 domain of GαS (Markby, et al. (1993) Science 262:1805–1901).

While the amino- and carboxy-termini of Gα subunits do not share striking homology either at the primary, secondary, or tertiary levels, there are several generalizations that can be made about them. First, the amino termini of Gα subunits have been implicated in the association of Gα with Gβγ complexes and in membrane association via N-terminal myristoylation. In addition, the carboxy-termini have been implicated in the association of Gαβγ heterotrimeric complexes with G protein-coupled receptors (Sullivan, et al. (1987) Nature 330:758–760); West, et al. (1985) J. Biol. Chem. 260:14428–14430); (Conklin, et al. (1993)Nature 363:274–276). Data in support of these generalizations about the function of the N-terminus derive from several sources, including both biochemical and genetic studies.

As indicated above, there is little if any sequence homology shared among the amino termini of Gα subunits. The amino terminal domains of Gα subunits that precede the first β-sheet (containing the sequence motif -LLLLGAGESG-; see Noel, et al. (supra) for the numbering of the structural elements of Gα subunits) vary in length from 41 amino acids (GPA1) to 31 amino acids (Gαt). Most Gα subunits share the consensus sequence for the addition of myristic acid at their amino termini (MGXaaS-), although not all Gα subunits that contain this motif have myristic acid covalently associated with the glycine at position 2 (Speigel, et al. (1991) TIBS 16:338–3441). The role of this post-translational modification has been inferred from studies in which the activity of mutant Gα subunits from which the consensus sequence for myristoylation has been added or deleted has been assayed (Mumby et al. (1990) Proc. Natl. Acad. Sci. USA 87: 728–732; (Linder, et al. (1991) J. Biol Chem. 266:4654–4659); Gallego, et al. (1992) Proc. Natl. Acad. ScL USA 89:9695–9699). These studies suggest two roles for N-terminal myristoylation. First, the presence of amino-terminal myristic acid has in some cases been shown to be required for association of Gα subunits with the membrane, and second, this modification has been demonstrated to play a role in modulating the association of Gα subunits with Gβγ complexes. The role of myristoylation of the GPA1 gene products, at present, unknown.

In other biochemical studies aimed at examining the role of the amino-terminus of Gα in driving the association between Gα and Gβγ subunits, proteolytically or genetically truncated versions of Gα subunits were assayed for their ability to associate with Gβγcomplexes, bind guanine nucleotides and/or to activate effector molecules. In all cases, Gα subunits with truncated amino termini were deficient in all three functions (Graf, et al. (1992) J. Biol. Chem. 267: 24307–24314); (Journot, et al. (1990) J. Biol. Chem. 265: 9009–9015); and (Neer, et al. (1988) J. Biol. Chem 263: 8996–9000). Slepak, et al. (1993, J. Biol. Chem. 268: 1414–1423) reported a mutational analysis of the N-terminal 56 a.a. of mammalian Gαo expressed in Escherichia coli. Molecules with an apparent reduced ability to interact with exogenously added mammalian Gβγ were identified in the mutant library. As the authors pointed out, however, the assay used to screen the mutants the extent of ADP-ribosylation of the mutant Gα by pertussis toxin was not a completely satisfactory probe of interactions between Gα and Gβγ. Mutations identified as inhibiting the interaction of the subunits, using this assay, may still permit the complexing of Gα and G13y while sterically hindering the ribosylation of Gα by toxin. Genetic studies examined the role of amino-terminal determinants of Gα in heterotrimer subunit association have been carried out in both yeast systems using GPA1-mammalian Gα hybrids (Kang, et al. (1990) *Mol. Cell. Biol.* 10:2582–2590) and in mammalian systems using Gαi/Gαs hybrids (Russell and Johnson (1993) *Mol. Pharmacol.* 44:255–263). In the former studies, gene fusions, composed of yeast GPA1 and mammalian Gα sequences were constructed by Kang, et al. (supra) and assayed for their ability to complement a gpa1 null phenotype (i.e., constitutive activation of the pheromone response pathway) in *S. cerevisiae*. Kang, et al. demonstrated that wild type mammalian Gαs, Gαi but not Gαo proteins are competent to associate with yeast Gα and suppress the gpa1 null phenotype, but only when overexpressed. Fusion proteins containing the amino-terminal 330 residues of GPA1 sequence linked to 160, 143, or 142 residues of the mammalian Gαs, Gαi and Gαo carboxyl-terminal regions, respectively, also coupled to the yeast mating response pathway when overexpressed on high copy plasmids with strong inducible (CUP) or constitutive (PGK) promoters. All three of these hybrid molecules were able to complement the gpa1 null mutation in a growth arrest assay, and were additionally able to inhibit afactor responsiveness and mating in tester strains. These last two observations argue that hybrid yeast-mammalian Gα subunits are capable of interacting directly with yeast Gβγ, thereby disrupting the normal function of the yeast heterotrimer. Fusions containing the amino terminal domain of Gαs, Gαi or Gαo, however, did not complement the gpa1 null phenotype, indicating a requirement for determinants in the amino terminal 330 amino acid residues of GPA1 for association and sequestration of yeast Gβγ complexes. Taken together, these data suggest that determinants in the amino terminal region of Gα subunits determine not only the ability to associate with Gβγ subunits in general, but also with specific Gβγ subunits in a species-restricted manner.

Hybrid Gαi/Gαs subunits have been assayed in mammalian expression systems (Russell and Johnson (supra). In these studies, a large number of chimeric Gα subunits were assayed for an ability to activate adenylyl cyclase, and therefore, indirectly, for an ability to interact with Gβγ(i.e., coupling of Gα to Gβγ=inactive cyclase; uncoupling of Gα from Gβγ=active cyclase). From these studies a complex picture emerged in which determinants in the region between residues 25 and 96 of the hybrids were found to determine the state of activation of these alleles as reflected in their rates of guanine nucleotide exchange and GTP hydrolysis and the extent to which they activated adenylyl cyclase in vivo. These data could be interpreted to support the hypothesis that structural elements in the region between the amino terminal methionine and the ~1 sheet identified in the crystal structure of Gαt (see Noel, et al. supra and Lambright, et al. supra) are involved in determining the state of activity of the heterotrimer by (1) driving association/dissociation between Gαand Gβγ subunits; (2) driving GDP/GTP exchange. While there is no direct evidence provided by these studies to support the idea that residues in this region of Gα and residues in Gβγ subunits contact one another, the data nonetheless provide a positive indication for the construction of hybrid Gα subunits that retain function. There is, however, a negative indicator that derives from this work in that some hybrid constructs resulted in constitutive activation of the chimeric proteins (i.e., a loss of receptor-dependent stimulation of Gβγ dissociation and effector activation).

D. Construction of Chimeric Gα Subunits.

In designing Gα subunits capable of transmitting, in yeast, signals originating at mammalian G protein-coupled receptors, two general desiderata were recognized. First, the subunits should retain as much of the sequence of the native mammalian proteins as possible. Second, the level of expression for the heterologous components should approach, as closely as possible, the level of their endogenous counterparts. The results described by King, et al. (1990, Science 250:121–123) for expression of the human β2-adrenergic receptor and Gαs in yeast, taken together with negative results obtained by Kang, et al. (supra) with full-length mammalian Gα subunits other than Gαs, led us to the following preferences for the development of yeast strains in which mammalian G protein-coupled receptors could be linked to the pheromone response pathway.

1. Mammalian Gα subunits will be expressed using the native sequence of each subunit or, alternatively, as minimal gene fusions with sequences from the amino-terminus of GPA1 replacing the homologous residues from the mammalian Gα subunits.

2. Mammalian Gα subunits will be expressed from the GPA1 promotor either on low copy plasmids or after integration into the yeast genome as a single copy gene.

3. Endogenous Gad subunits will be provided by the yeast STE4 and STE18 loci.

E. Site-Directed Mutagenesis versus Random Mutagenesis

There are two general approaches to solving structure-function problems of the sort presented by attempts to define the determinants involved in mediating the association of the subunits that comprise the G protein heterotrimer. The first approach, discussed above with respect to hybrid constructs, is a rational one in which specific mutations or alterations are introduced into a molecule based upon the available experimental evidence. In a second approach, random mutagenesis techniques, coupled with selection or screening systems, are used to introduce large numbers of mutations into a molecule, and that collection of randomly mutated molecules is then subjected to a selection for the desired phenotype or a screen in which the desired phenotype can be observed against a background of undesirable phenotypes. With random mutagenesis one can mutagenize an entire molecule or one can proceed by cassette mutagenesis. In the former instance, the entire coding region of a molecule is mutagenized by one of several methods (chemical, PCR, doped oligonucleotide synthesis) and that collection of randomly mutated molecules is subjected to selection or screening procedures. Random mutagenesis can be applied in this way in cases where the molecule being studied is relatively small and there are powerful and stringent selections or screens available to discriminate between the different classes of mutant phenotypes that will inevitably arise. In the second approach, discrete regions of a protein, corresponding either to defined structural (i.e. α-helices, β-sheets, turns, surface loops) or functional determinants (e.g., catalytic clefts, binding determinants, transmembrane segments) are subjected to saturating or semi-random mutagenesis and these mutagenized cassettes are re-introduced into the context of the otherwise wild type allele. Cassette mutagenesis is most useful when there is experimental evidence available to suggest a particular function for a region of a molecule and there is a powerful selection and/or screening approach available to discriminate between interesting and uninteresting mutants. Cassette mutagenesis is also useful when the parent molecule is comparatively large and the desire is to map the functional domains of a molecule by mutagenizing the molecule in a step-wise fashion, i.e. mutating one linear cassette of residues at a time and then assaying for function.

The present invention contemplates applying random mutagenesis in order to further delineate the determinants involved in Gα-Gβγ association. Random mutagenesis may be accomplished by many means, including:

1. PCR mutagenesis, in which the error prone Taq polymerase is exploited to generate mutant alleles of Gα subunits, which are assayed directly in yeast for an ability to couple to yeast Gβγ.

2. Chemical mutagenesis, in which expression cassettes encoding Gα subunits are exposed to mutagens and the protein products of the mutant sequences are assayed directly in yeast for an ability to couple to yeast G βγ.

3. Doped synthesis of oligonucleotides encoding portions of the Gα gene.

4. In vivo mutagenesis, in which random mutations are introduced into the coding region of Gα subunits by passage through a mutator strain of *E. coli*, XL 1-Red (mutD5 mutS mutt) (Stratagene, Menasa, Wis.).

The random mutagenesis may be focused on regions suspected to be involved in Gα-Gβγ association as discussed in the next section. Random mutagenesis approaches are feasible for two reasons. First, in yeast one has the ability to construct stringent screens and facile selections (growth vs. death, transcription vs. lack of transcription) that are not readily available in mammalian systems. Second, when using yeast it is possible to screen efficiently through thousands of transformants rapidly. Cassette mutagenesis is immediately suggested by the observation (see infra) that the $GPA_{41}$ hybrids couple to the pheromone response pathway. This relatively small region of Gα subunits represents a reasonable target for this type of mutagenesis. Another region that may be amenable to cassette mutagenesis is that defining the surface of the switch region of Gα subunits that is solvent-exposed in the crystal structures of Gαi and transducin. From the data described below, this surface may contain residues that are in direct contact with yeast Gβγ subunits, and may therefore be a reasonable target for mutagenesis.

F. Rational Design of Chimeric Gα Subunits

Several classes of rationally designed GPA1-mammalian Gα hybrid subunits have been tested for the ability to couple to yeast βγ. The first, and largest, class of hybrids are those that encode different lengths of the GPA1 amino terminal domain in place of the homologous regions of the mammalian Gα subunits. This class of hybrid molecules includes $GPA_{BAMH1}$, $GPA_{41}$, $GPA_{ID}$, and $GPA_{LW}$ hybrids, described below. The rationale for constructing these hybrid Gα proteins is based on results, described above, that bear on the importance of the amino terminal residues of Gα in mediating interaction with Gβγ.

Preferably, the yeast Gα subunit is replaced by a chimeric Gα subunit in which a portion, e.g., at least about 20, more preferably at least about 40, amino acids, which is substantially homologous with the corresponding residues of the amino terminus of the yeast Gα, is fused to a sequence substantially homologous with the main body of a mammalian (or other exogenous) Gα. While 40 amino acids is the suggested starting point, shorter or longer portions may be tested to determine the minimum length required for coupling to yeast Gβγ and the maximum length compatible with retention of coupling to the exogenous receptor. It is presently believed that only the fmal 10 or 20 amino acids at the carboxy terminus of the Gα subunit are required for interaction with the receptor.

$GPA_{BAMH1}$ hybrids. Kang et al. supra. described hybrid G α subunits encoding the amino terminal 310 residues of GPA1 fused to the carboxyl terminal 160, 143 and 142 residues, respectively, of GαS, Gαi2, and Gαo. In all cases examined by Kang et al., the hybrid proteins were able to complement the growth arrest phenotype of gpal strains. We have confirmed these findings and, in addition, have constructed and tested hybrids between GPA1 and Gαi3, Gαq and Gα16. All hybrids of this type that have been tested functionally complement the growth arrest phenotype of gpal strains.

GPA41 hybrids. The rationale for constructing a minimal hybrid encoding only 41 amino acids of GPA1 relies upon the biochemical evidence for the role of the amino-terminus of Gα subunits discussed above, together with the following observation. G β and Gγ subunits are known to interact via α-helical domains at their respective amino-termini (Pronin, et al. (1992) *Proc. Natl. Acad. Sci. USA* 89:6220–6224); Garritsen, et al.1993). The suggestion that the amino termini of Gα subunits may form an helical coil and that this helical coil may be involved in association of Gα with Gβγ (Masters et al (1986) *Protein Engineering* 1:47–54); Lupas et al.(1992) *FEBS Lett.* 314:105–108) leads to the hypothesis that the three subunits of the G-protein heterotrimer interact with one another reversibly through the winding and unwinding of their amino-terminal helical regions. A mechanism of this type has been suggested, as well, from an analysis of leucine zipper mutants of the GCN4 transcription factor (Harbury, et al. (1993) *Science* 262:1401–1407). The rationale for constructing hybrids like those described by Kang, et al. supra., that contain a majority of yeast sequence and only minimal mammalian sequence, derives from their ability to function in assays of coupling between Gα and Gβγ subunits. However, these chimeras had never been assayed for an ability to couple to both mammalian G protein-coupled receptors and yeast Gβγ subunits, and hence to reconstitute a hybrid signaling pathway in yeast.

$GPA_{41}$ hybrids that have been constructed and tested include Gαs, Gαi2, Gαi3, Gαq, $Gαo_a$, $Gαo_b$ and Gα16. Hybrids of Gαs, Gαi2, Gαi3, and Gα16 functionally complement the growth arrest phenotype of gpal strains, while $GPA_{41}$ hybrids of $Gαo_a$ and $Gαo_b$ do not. In addition to being tested in a growth arrest assay, these constructs have been assayed in the more sensitive transcriptional assay for activation of a fuslp-HIS3 gene. In both of these assays, the $GPA_{41}$-Gαs hybrid couples less well than the $GPα_{41}$-i2, -i3, and -16 hybrids, while the $GPα_{41}$ -$o_a$, and -$o_b$ hyrids do not function in either assay.

Several predictive algorithms indicate that the amino terminal domain up to the highly conserved sequence motif- LLLLGAGESG- (the first L in this motif is residue 43 in GPA1) forms a helical structure with amphipathic character. Assuming that a heptahelical repeat unit, the following hybrids between GPA1 and GαS can be used to define the number of helical repeats in this motif necessary for hybrid function:

GPA1-7/Gas8-394
GPA1-14/Gas15-394
GPA1-21/Gas22-394
GPA1-28/Gas29-394
GPA1-35/Gas36-394
GPA1-42/Gas43-394

In these hybrids, the prediction is that the structural repeat unit in the amino terminal domain up to the tetra-leucine motif is 7, and that swapping sequences in units of 7 will in effect amount to a swap of unit turns of turns of the helical structure that comprises this domain.

A second group of "double crossover." hybrids of this class are those that are aligned on the first putative heptad repeat beginning with residue G11 in GPA1. In these hybrids, helical repeats are swapped from GPA1 into a GαS backbone one heptad repeat unit at a time.

GαS1-10/GPA11-17/Gαs18-394
GαS1-17/GPA18-24/GαS25-394
GαS1-17/GPA25-31/GαS32-394
GαS?-17/GPA32-38/GαS39-394

The gap that is introduced between residues 9 and 10 in the GaS sequence is to preserve the alignment of the -LLLLGAGE-sequence motif. This class of hybrids can be complemented by cassette mutagenesis of each heptad repeat followed by screening of these collections of "heptad" libraries in standard coupling assays.

A third class of hybrids based on the prediction that the amino terminus forms a helical domain with a heptahelical repeat unit are those that effect the overall hydrophobic or hydrophilic character of the opposing sides of the predicted helical structure (See Lupas et al. supra). In this model, the α and d positions of the heptad repeat abcdefg are found to be conserved hydrophobic residues that define one face of the helix, while the e and g positions define the charged face of the helix. In this class of hybrids, the sequence of the GαS parent is maintained except for specific substitutions at one or more of the following critical residues to render the different helical faces of GαS more "GPA1-like"

K8Q
+I-10
E1OG
Q12E
R13S
N14D
E15P
E15F
K17L
E21R
K28Q
K32L
V36R

This collection of single mutations could be screened for coupling efficiency to yeast Gβγ and then constructed in combinations (double and greater if necessary).

A fourth class of hybrid molecules that span this region of GPA1-Gα hybrids are those that have junctions between GPA1 and Gα subunits introduced by three primer PCR. In this approach, the two outside primers are encoded by sequences at the initiator methionine of GPA1 on the 5' side and at the tetraleucine motif of GαS (for example) on the 3' side. A series of junctional primers spanning different junctional points can be mixed with the outside primers to make a series of molecules each with different amounts of GPA1 and GαS sequences, respectively.

$GPA_{ID}$ and $GPA_{LW}$ hybrids. The regions of high homology among Gβγ subunits that have been identified by sequence alignment are interspersed throughout the molecule. The G1 region containing the highly conserved -GSGESGDST- motif is followed immediately by a region of very low sequence consevation, the "i1" or insert 1 region. Both sequence and length vary considerably among the i1 regions of the Gα subunits. By aligning the sequences of Gα subunits, the conserved regions bounding the i1 region were identified and two additional classes of GPA1-Gα hybrids were constructed. The $GPA_{ID}$ hybrids encode the amino terminal 102 residues of GPA1 (up to the sequence -QARKLGIQ-) fused in frame to mammalian Gα subunits, while the GPALW hybrids encode the amino terminal 244 residues of GPA1 (up to the sequence LIHEDIAKA- in GPA1). The reason for constructing the $GPA_{ID}$ and $GPA_{LW}$ hybrids was to test the hypothesis that the i1 region of GPA1 is required for mediating the interaction of GPA1 with yeast Gβγ subunits, for the stable expression of the hybrid molecules, or for function of the hybrid molecules. The $GPA_{ID}$ hybrids contain the amino terminal domain of GPA1 fused to the i1 domain of mammalian subunits, and therefore do not contain the GPA1 i1 region, while the $GPA_{LW}$ hybrids contain the amino terminal 244 residues of GPA1 including the entire i1 region (as defined by sequence alignments). Hybrids of both $GPA_{ID}$ and $GPA_{LW}$ classes were constructed for GαS, C-αi2, Gαi3, Gαo$_a$, and Gα16; none of these hybrids complemented the gpa1 growth arrest phenotype.

Subsequent to the construction and testing of the $GPA_{ID}$ and GPALW classes of hybrids, the crystal structures of $G_{transducin}$ in both the GDP and GTPγS-liganded form, and the crystal structure of several Gαil variants in the GTPγS-liganded and GDP-AIF$_4$ forms were reported (Noel et al. supra; Lambright et al. supra; and Coleman et al.(1994) Science 265:1405–1412). The crystal structures reveal that the ilregion defined by sequence alignment has a conserved structure that is comprised of six alpha helices in a rigid array, and that the junctions chosen for the construction of the $GPA_{ID}$ and $GPA_{LW}$ hybrids were not compatible with conservation of the structural features of the i1 region observed in the crystals. The junction chosen for the $GPA_{ID}$ hybrids falls in the center of the long αA helix; chimerization of this helix in all likelihood destabilizes it and the protein structure in general. The same is true of the junction chosen for the $GPA_{LW}$ hybrids in which the crossover point between GPA1 and the mammalian Gα subunit falls at the end of the short αC helix and therefore may distort it and destabilize the protein.

The failure of the $GPA_{ID}$ and $GPA_{LW}$ hybrids is predicted to be due to disruption of critical structural elements in the ii region as discussed above. Based upon new alignments and the data presented in Noel et al (supra), Lambright et al (supra), and Coleman et al (supra), this problem can be averted with the ras-like core domain and the ii helical domain are introduced outside of known structural elements like alpha-helices.

Hybrid A GαS1-67/GPA66-299/GαS203-394

This hybrid contains the entire i1 insert of GPA1 interposed into the GαS sequence.

Hybrid B GPA1-41/GαS4443-67/GPA66-299/GαS203-394

This hybrid contains the amino terminal 41 residues of GPA1 in place of the 42 amino terminal residues of GαS found in Hybrid A.

Gas Hybrids. There is evidence that the "switch region" encoded by residues 171–237 of Gα transducin (using the numbering of (Noel et al (supra) also plays a role in Gβγ coupling. First, the G226A mutation in GαS prevents the GTP-induced conformational change that occurs with exchange of GDP for GTP upon receptor activation by ligand. This residue maps to the highly conserved sequence -DVGGQ-, present in all Gα subunits and is involved in GTP hydrolysis. In both the Gαt and Gα i1 crystal structures, this sequence motif resides in the loop that connects the β3 sheet and the α2 helix in the guanine nucleotide binding core. In addition to blocking the conformational change that occurs upon GTP binding, this mutation also prevents dissociation of GTP-liganded Gαs from Gβγ. Second, crosslinking data reveals that a highly conserved cysteine residue in the α2 helix (C215 in Gαo, C210 in Gαt) can be crosslinked to the carboxy terminal region of Gβ subunits. Finally, genetic evidence (Whiteway et al. (1993) Mol Cell Biol. 14:3233–3239) identifies an important single residue in GPA1 (E307) in the β2 sheet of the core structure that may be in direct contact with βγ. A mutation in the GPA1 protein at this position suppresses the constitutive signalling phenotype of a variety of STE4 (Gβ) dominant negative mutations that are also known to be defective in Gα-Gβγ association (as assessed in two-hybrid assay in yeast as well as by more conventional genetic tests).

We have tested the hypothesis that there are switch region determinants involved in the association of Gα with Gβγ by constructing a series of hybrid Gα proteins encoding portions of GPA1 and GαS in different combinations.

Two conclusions may be drawn. First, in the context of the amino terminus of GαS, the GPA1 switch region suppresses coupling to yeast Gβγ (SGS), while in the context of the GPA1 amino terminus the GPA1 switch region stabilizes coupling with Gβγ (GPβγ-SGS). This suggests that these two regions of GPA1 collaborate to allow interactions between Gα subunits and Gβγ subunits. This conclusion is somewhat mitigated by the observation that the $GPA_{41}$-Gαs hybrid that does not contain the GPA1 switch region is able to complement the growth arrest phenotype of gpal strains. We have not to date noted a quantitative difference between the behavior of the $GPA_{41}$-Gαs allele and the GPA~I~-SGS allele, but if this interaction is somewhat degenerate, then it may be difficult to quantitate this accurately. The second conclusion that can be drawn from these results is that there are other determinants involved in stabilizing the interaction of Gα with Gβγ beyond these two regions as none of the GPA1/Gαs hybrid proteins couple as efficiently to yeast Gβγ as does native GPA1.

The role of the surface-exposed residues of this region may be crucial for effective coupling to yeast Gβγ, and can be incorporated into hybrid molecules as follows below.

GαS-GPA-Switch    GαS    1-202/GPA298-350/GαS 253-394

This hybrid encodes the entire switch region of GPA 1 in the context of GαS.

GαS-GPA-α2 GQS 1-226/GPA322-332/GQS 238-394

This hybrid encodes the $a^2$ helix of GPA1 in the context of GαS.

GPA41-GαS-GPA-α2GPA1-41/GQS43-226/GPA322-3321GQS238-394

This hybrid encodes the 41 residue amino terminal domain of GPA1 and the α2 helix of GPA1 in the context of GαS.

Finally, the last class of hybrids that will be discussed here are those that alter the surface exposed residues of the β2 and β3 sheets of αS so that they resemble those of the GPA1 QS helix. These altered α2 helical domains have the following structure. (The positions of the altered residues correspond to GαS.)

L203K
    K211E
    D215G
    K216S
    D229S

These single mutations can be engineered into a GαS backbone singly and in pairwise combinations. In addition, they can be introduced in the context of both the full length GαS and the $GPA_{41}$-GαS hybrid described previously. All are predicted to improve the coupling of Gα subunits to yeast Gβγ subunits by virtue of improved electrostatic and hydrophobic contacts between this region and the regions of Gβ defined by Whiteway and coworkers (Whiteway et al (supra) that define site(s) that interact with GPA1).

In summary, the identification of hybrid Gα subunits that couple to the yeast pheromone pathway has led to the following general observations. First, all $GPA_{BAMH1}$ hybrids associate with yeast Gβγ, therefore at a minimum these hybrids contain the determinants in GPA1 necessary for coupling to the pheromone response pathway. Second, the amino terminal 41 residues of GPA1 contain sufficient determinants to facilitate coupling of Gα hybrids to yeast Gβγ in some, but not all, instances, and that some Gα subunits contain regions outside of the first 41 residues that are sufficiently similar to those in GPA1 to facilitate interaction with GPA1 even in the absence of the amino terminal 41 residues of GPA1. Third, there are other determinants in the first 310 residues of GPA1 that are involved in coupling Gα subunits to yeast Gβγ subunits.

The various classes of hybrids noted above are not mutually exclusive. For example, a GPA1 containing GPA1-$_{41}$ could also feature the L203K mutation.

While, for the sake of simplicity, we have described hybrids of yeast GPA1 and a mammalian Gαs, it will be appreciated that hybrids may be made of other yeast Gα subunits and/or other mammalian Gα subunits, notably mammalian Gαi subunits. Moreover, while the described hybrids are constructed from two parental proteins, hybrids of three or more parental proteins are also possible.

As shown in the Examples, chimeric Gα subunits have been especially useful in coupling receptors to Gαi species.

G. Expression of Gα

Kang et al. supra reported that several classes of native mammalian G∞subunits were able to interact functionally with yeast a subunits when expression of Gα was driven from a constitutively active, strong promoter (PGK) or from a strong inducible promoter (CUP). These authors reported that rat GαS, Gαi2 or Gαo expressed at high level coupled to yeast βγ. High level expression of mammalian Gα (i.e. non-stoichiometric with respect to yeast βγ) is not desirable for uses like those described in this application. Reconstruction of G protein-coupled receptor signal transduction in yeast requires the signalling component of the heterotrimeric complex (Gβγ) to be present stoichiometrically with Gα subunits. An excess of Gα subunits (as was required for coupling of mammalian Gαi2 and Gαo to yeast Gβγ in Kang et al.) would dampen the signal in systems where Gβγ subunits transduce the signal. An excess of Gα subunits raises the background level of signaling in the system to unacceptably high levels. Preferably, levels of Gα and Gβγ subunits are balanced. For example, heterologous Gα subunits may be expressed from a low copy (CEN ARS) vector containing the endogenous yeast GPA promoter and the GPA1 3' untranslated region. The minimum criterion, applied to a heterologous Gαsubunit with respect to its ability to couple functionally to the yeast pheromone pathway, is that it complement a gpal genotype when expressed from the GPA1 promoter on low copy plasmids or from an integrated, single copy gene. In the work described in this application, all heterologous Gα subunits have been assayed in two biological systems. In the first assay heterologous Gα subunits are tested for an ability to functionally complement the growth arrest phenotype of gpal strains. In the second assay the transcription of a fusl-HIS3 reporter gene is used to measure the extent to which the pheromone response pathway is activated, and hence the extent to which the heterologous Gα subunit sequesters the endogenous yeast Gβγ complex. Mammalian Gαs, Gαi2, Gαi3, Gαq, Gα11, Gα16, Gαo$_a$, Gαo$_b$, and Gαz from rat, murine or human origins were expressed from a low copy, CEN ARS vector containing the GPA1 promoter. Functional complementation of gpa1 strains was not observed in either assay system with any of these full-length Gα constructs with the exception of rat and human GαS.

H. Chimeric Yeast βγ Subunits

An alternative to the modification of a mammalian Gα subunit for improved signal transduction is the modification of the pertinent sites in the yeast Gβ or Gγ subunits. The principles discussed already with respect to Gα subunits apply, mutatis mutandis, to yeast Gβ or Gγ.

For example, it would not be unreasonable to target the yeast Ste4p Gβsubunit with cassette mutagenesis. Specifically, the region of Ste4p that encodes several of the dominant negative, signaling-defective mutations would be an excellent target for cassette mutagenesis when looking for coupling of yeast Gβγ to specific mammalian Gα subunits.

X. Peptide Libraries

While others have engineered yeast cells to facilitate screening of exogenous drugs as receptor agonists and antagonists, the cells did not themselves produce both the drugs and the receptors. Yeast cells engineered to produce the receptor, but that do not produce the drugs themselves, are inefficient. To utilize them one must bring a sufficient concentration of each drug into contact with a number of cells in order to detect whether or not the drug has an action. Therefore, a microtiter plate well or test tube must be used for each drug. The drug must be synthesized in advance and be sufficiently pure to judge its action on the yeast cells. When the yeast cell produces the drug, the effective concentration is higher.

Peptide libraries are systems which simultaneously display, in a form which permits interaction with a target, a highly diverse and numerous collection of peptides. These peptides may be presented in solution (Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990)*Science* 249:404–406); (Cwirla et al. (1990) *Proc. Natl. Acad. Sci.* 87:6378–6382); (Felici (1991) *J. Mol. Biol.* 222:301–310); (Ladner supra.). Many of these systems are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. While a cell surface receptor may be used as a target, the screening will not reveal whether the binding of the peptide caused an allosteric change in the conformation of the receptor.

The Ladner et al. patent, U.S. Ser. No. 5,096,815, describes a method of identifying novel proteins or polypeptides with a desired DNA binding activity. Semi-random ("variegated") DNA encoding a large number of different potential binding proteins is introduced, in expressible form, into suitable host cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a receptor protein. Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., *J. Biol.Chem.*(1989) 264, 20206 and Kaiser et al. (1987) *Science* 235:312, respectively).

The peptide library of the present invention takes the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins (see, for example, U.S. Pat. Nos. 5,270,181 and 5,292,646; and PCT publication WO94/02502). The combinatoriai peptide can be attached one the terminus of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3–100 amino acids in length, more preferably at least 5–50, and even more preferably at least 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In another embodiment, the peptide library is derived to express a combinatorial library of polypeptides which are based at least in part on a known polypeptide sequence or a portion thereof (not a cDNA library). That is, the sequences of the library is semi-random, being derived by combinatorial mutagenesis of a known sequence. See, for example, Ladner et al. PCT publication WO 90/02909; Garrard et al., PCT publication WO 92/09690; Marks et al. (1992) *J. Biol. Chem.* 267:16007–16010; Griffths et al. (1993) *EMBO J.* 12:725–734; Clackson et al. (1991) *Nature* 352:624–628; and Barbas et al. (1992) *PNAS* 89:4457–4461. Accordingly, polypeptide(s) which are known ligands for a target receptor can be mutagenized by standard techniques to derive a variegated library of polypeptide sequences which can further be screened for agonists and/or antagonists. For example, the surrogate ligand identified for FPRL-1, e.g., the Ser-Leu-Leu-Trp-Leu-Thr-Cys-Arg-Pro-Trp-Glu-Ala-Met peptide, can be mutagenized to generate a library of peptides with some relationship to the original tridecapeptide. This library can be expressed in a reagent cell of the present invention, and other receptor activators can be isolated from the library. This may permit the identification of even more potent FPRL-1 surrogate ligands.

Alternatively, the library can be expressed under conditions wherein the cells are in contact with the original tridecapeptide, e.g., the FPRL-1 receptor is being induced by that surrogate ligand. Peptides from an expressed library can be isolated based on their ability to potentiate the induction, or to inhibit the induction, caused by the surrogate ligand. The latter of course will identify potential antagonists of chemoattractant receptors. In still other embodiments, the surrogate ligand can be used to screen exogenous compound libraries (peptide and non-peptide) which, by modulating the activity of the identified surrogate, will presumably also similarly effect the native ligand's effect on the target receptor. In such embodiments, the surrogate ligand can be applied to the cells, though is preferably produced by the reagent cell, thereby providing an autocrine cell.

In still another embodiment, the combinatorial polypeptides are produced from a cDNA library.

In a preferred embodiment of the present invention, the yeast cells collectively produce a "peptide library", preferably including at least $10^3$ to $10^7$ different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In the present invention, the peptides of the library are encoded by a mixture of DNA molecules of different sequence. Each peptide-encoding DNA molecule is ligated with a vector DNA molecule and the resulting recombinant DNA molecule is introduced into a host cell. Since it is a matter of chance which peptide encoding DNA molecule is introduced into a particular cell, it is not predictable which peptide that cell will produce. However, based on a knowledge of the manner in which the mixture was prepared, one may make certain statistical predictions about the mixture of peptides in the peptide library.

It is convenient to speak of the peptides of the library as being composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

XI. Screenine and Selection: Assays of Second Messenger Generation

When screening for bioactivity of peptides, intracellular second messenger generation can be measured directly. A variety of intracellular effectors have been identified as being G-protein-regulated, including adenylyl cyclase, cyclic GMP, phosphodiesterases, phosphoinositidase C, and phospholipase $A_2$. In addition, G proteins interact with a range of ion channels and are able to inhibit certain voltage-sensitive $Ca^{++}$ transients, as well as stimulating cardiac $K^+$ channels.

In one embodiment, the GTPase enzymatic activity by G proteins can be measured in plasma membrane preparations by determining the breakdown of $\gamma^{32}P$ GTP using techniques that are known in the art (For example, see *Signal Transduction: A Practical Approach*. G. Milligan, Ed. Oxford University Press, Oxford England). When receptors that modulate cAMP are tested, it will be possible to use standard techniques for cAMP detection, such as competitive assays which quantitate $[^3H]cAMP$ in the presence of unlabelled cAMP.

Certain receptors stimulate the activity of phospholipase C which stimulates the breakdown of phosphatidylinositol 4,5, bisphosphate to 1,4,5-IP3 (which mobilizes intracellular Ca++) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

The mobilization of intracellular calcium or the influx of calcium from outside the cell can be measured using standard techniques. The choice of the appropriate calcium indicator, fluorescent, bioluminescent, metallochromic, or Ca++-sensitive microelectrodes depends on the cell type and the magnitude and time constant of the event under study (Borle (1990) *Environ Health Perspect* 84:45–56). As an exemplary method of Ca++ detection, cells could be loaded with the Ca++sensitive fluorescent dye fura-2 or indo-1, using standard methods, and any change in Ca++measured using a fluorometer.

The other product of PIP2 breakdown, DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In the case of certain receptors, it may be desirable to screen for changes in cellular phosphorylation. Such assay formats may be useful when the receptor of interest is a receptor tyrosine kinase. For example, yeast transformed with the FGF receptor and a ligand which binds the FGF receptor could be screened using colony immunoblotting (Lyons and Nelson (1984) Proc. Natl. Acad Sci. USA 81:7426–7430) using anti-phosphotyrosine. In addition, tests for phosphorylation could be useful when a receptor which may not itself be a tyrosine kinase, activates protein kinases that function downstream in the signal transduction pathway. Likewise, it is noted that protein phosphorylation also plays a critical role in cascades that serve to amplify signals generated at the receptor. Multi-kinase cascades allow not only signal amplification but also signal divergence to multiple effectors that are often cell-type specific, allowing a growth factor to stimulate mitosis of one cell and differentiation of another.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases (ERK1 and ERK2). Activated MAP kinase then phosphorylates many key regulatory proteins, including p90RSK and Elk-1 that are phosphorylated when MAP kinase translocates to the nucleus. Homologous pathways exist in mammalian and yeast cells. For instance, an essential part of the S. cerevisiae pheromone signaling pathway is comprised of a protein kinase cascade composed of the products of the STE 11, STE7, and FUS3/KSS1 senes (the latter pair are distinct and functionally redundant). Accordingly, phosphorylation and/or activation of members of this kinase cascade can be detected and used to quantitate receptor engagement. Phosphotyrosine specific antibodies are available to measure increases in tyrosine phosphorylation and phospho-specific antibodies are commercially available (New England Biolabs, Beverly, Mass.).

Modified methods for detecting receptor-mediated signal transduction exist and one of skill in the art will recognize suitable methods that may be used to substitute for the example methods listed.

XII. Screening and Selection Using Reporter Gene Constructs

In addition to measuring second messenger production, reporter gene constructs can be used. Reporter gene constructs are prepared by operatively linking a reporter gene with at least one transcriptional regulatory element. If only one transcriptional regulatory element is included it must be a regulatable promoter, At least one the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art. Reporter genes A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368).

Transcriptional control elements include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In the most preferred constructs, the transcriptional regulatory elements are derived from the c-fos gene.

The c-fos proto oncogene is the cellular homolog of the transforming gene of FBJ osteosarcoma virus. It encodes a nuclear protein that most likely involved in normal cellular growth and differentiation. Transcription of c-fos is transiently and rapidly activated by growth factors and by other inducers of other cell surface proteins, including hormones, differentiation-specific agents, stress, mitogens and other known inducers of cell surface proteins. Activation is protein synthesis independent. The c-fos regulatory elements include (see, Verma et al. (1987) Cell 51: a TATA box that is required for transcription initiation; two upstream elements for basal transcription, and an enhancer, which includes an element with dyad symmetry and which is required for induction by TPA, serum, EGF, and PMA.

The 20 bp transcriptional enhancer element located between −317 and −298 bp upstream from the c-fos mRNA cap site, which is essential for serum induction in serum starved NIH 3T3 cells. One of the two upstream elements is located at −63−−57 and it resembles the consensus sequence for cAMP regulation.

Other promoters and transcriptional control elements, in addition to those described above, include the vasoactive intestinal peptide (VIP) gene promoter (cAMP responsive;

Fink et al. (1988), Proc. Natl. Acad. Sci. 85:6662–6666); the somatostatin gene promoter (cAMP responsive; Montminy et al. (1986), Proc. Natl. Acad. Sci. 8.3:6682–6686); the proenkephalin promoter (responsive to cAMP, nicotinic agonists, and phorbol esters; Comb et al. (1986), Nature 323:353–356); the phosphoenolpyruvate carboxy-kinase gene promoter (cAMP responsive; Short et al. (1986), J. Biol. Chem. 261:9721–9726); the NGFI-A gene promoter (responsive to NGF, cAMP, and serum; Changelian et al. (1989). Proc. Natl. Acad. Sci. 86:377–381); and others that may be known to or prepared by those of skill in the art.

In certain assays it may be desirable to use changes in growth in the screening procedure. For example, one of the consequences of activation of the pheromone signal pathway in wild-type yeast is growth arrest. If one is testing for an antagonist of a G protein-coupled receptor, this normal response of growth arrest can be used to select cells in which the pheromone response pathway is inhibited. That is, cells exposed to both a known agonist and a peptide of unknown activity will be growth arrested if the peptide is neutral or an agonist, but will grow normally if the peptide is an antagonist. Thus, the growth arrest response can be used to advantage to discover peptides that function as antagonists.

However, when searching for peptides which can function as agonists of G protein-coupled receptors, or other pheromone system proteins, the growth arrest consequent to activation of the pheromone response pathway is an undesirable effect since cells that bind peptide agonists stop growing while surrounding cells that fail to bind peptides will continue to grow. The cells of interest, then, will be overgrown or their detection obscured by the background cells, confounding identification of the cells of interest. To overcome this problem the present invention teaches engineering the cell such that: 1) growth arrest does not occur as a result of exogenous signal pathway activation (e.g., by inactivating the FAR1 gene); and/or 2) a selective growth advantage is conferred by activating the pathway (e.g., by transforming an auxotrophic mutant with a HIS3 gene under the control of a pheromone-responsive promoter, and applying selective conditions).

It is, of course, desirable that the exogenous receptor be exposed on a continuing basis to the peptides. Unfortunately, this is likely to result in desensitization of the pheromone pathway to the stimulus. For example, the mating signal transduction pathway is known to become desensitized by several mechanisms including pheromone degradation and modification of the function of the receptor, G proteins,s and/or downstream elements of the pheromone signal transduction by the products of the SST2, STE50, AFR1 (Konopka, J. B. (1993) Mol. Cell. Biol.13:6876–6888) and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations e.g. STE50, sgv1,bar1, ste2,ste3,pik1, msg5, sig1, and aft1, have the similar effect of increasing the sensitivity of the bioassay. Thus desensitization may be avoided by mutating (which may include deleting) the SST2 gene so that it no longer produces a functional protein, or by mutating one of the other genes listed above.

If the endogenous homolog of the receptor is produced by the yeast cell, the assay will not be able to distinguish between peptides which interact with the endogenous receptor and those which interact with the exogenous receptor. It is therefore desirable that the endogenous gene be deleted or otherwise rendered nonfunctional.

In the case of receptors which modulate cyclic AMP, a transcriptional based readout can be constructed using the cyclic AMP response element binding protein, CREB, which is a transcription factor whose activity is regulated by phosphorylation at a particular serine (S133). When this serine residue is phosphorylated, CREB binds to a recognition sequence known as a CRE (cAMP Responsive Element) found to the 5' of promotors known to be responsive to elevated cAMP levels. Upon binding of phosphorylated CREB to a CRE, transcription from this promoter is increased.

Phosphorylation of CREB is seen in response to both increased cAMP levels and increased intracellular Ca levels. Increased cAMP levels result in activation of PKA, which in turn phosphorylates CREB and leads to binding to CRE and transcriptional activation. Increased intracellular calcium levels results in activation of calcium/calmodulin responsive kinase IV (CaM kinase IV). Phosphorylation of CREB by CaM kinase IV is effectively the same as phosphorylation of CREB by PKA, and results in transcriptional activation of CRE containing promotors.

Therefore, a transcriptional-based readout can be constructed in cells containing a reporter gene whose expression is driven by a basal promoter containing one or more CRE. Changes in the intracellular concentration of $Ca^{++}$ (a result of alterations in the activity of the receptor upon engagement with a ligand) will result in changes in the level of expression of the reporter gene if: a) CREB is also co-expressed in the cell, and b) either the endogenous yeast CaM kinase will phosphorylate CREB in response to increases in calcium or if an exogenously expressed CaM kinase IV is present in the same cell. In other words, stimulation of PLC activity will result in phosphorylation of CREB and increased transcription from the CRE-construct, while inhibition of PLC activity will result in decreased transcription from the CRE-responsive construct.

As described in Bonni et al. (1993) *Science* 262:1575–1579, the observation that CNTF treatment of SK-N-MC cells leads to the enhanced interaction of STAT/p91 and STAT related proteins with specific DNA sequences suggested that these proteins might be key regulators of changes in gene expression that are triggered by CNTF. Consistent with this possibility is the finding that DNA sequence elements similar to the consensus DNA sequence required for STAT/p91 binding are present upstream of a number of genes previously found to be induced by CNTF (e.g., Human c-fos, Mouse c-fos, Mouse tis11, Rat junB, Rat SOD-1, and CNTF). Those authors demonstrated the ability of STAT/p91 binding sites to confer CNTF responsiveness to a non-responsive reporter gene. Accordingly, a reporter construct for use in the present invention for detecting signal transduction through STAT proteins, such as from cytokine receptors, can be generated by using −71 to +109 of the mouse c-fos gene fused to the bacterial chloramphenicol acetyltransferase gene (−71fosCAT) or other detectable marker gene. Induction by a cytokine receptor induces the tyrosine phosphorylation of STAT and STAT-related proteins, with subsequent translocation and binding of these proteins to the STAT-RE. This then leads to activation of transcription of genes containing this DNA element within their promoters.

In preferred embodiments, the reporter gene is a gene whose expression causes a phenotypic change which is screenable or selectable. If the change is selectable, the phenotypic change creates a difference in the growth or survival rate between cells which express the reporter gene and those which do not. If the change is screenable, the phenotype change creates a difference in some detectable characteristic of the cells, by which the cells which express the marker may be distinguished from those which do not. Selection is preferable to screening in that it can provide a means for amplifying from the cell culture those cells which express a test polypeptide which is a receptor effector.

The marker gene is coupled to the receptor signaling pathway so that expression of the marker gene is dependent on activation of the receptor. This coupling may be achieved by operably linking the marker gene to a receptor-responsive promoter. The term "receptor-responsive promoter" indicates a promoter which is regulated by some product of the target receptor's signal transduction pathway.

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA binding repressor protein, and incorporating a suitable operator site into the promoter or other suitable region of the marker gene.

In the case of yeast, suitable positively selectable (beneficial) genes include the following: URA3, LYS2, HIS3, LEU2, TRP1; ADE1,2,3,4,5,7,8; ARGl, 3, 4, 5, 6, 8; HIS1, 4, 5; ILV1, 2, 5; THR1, 4; TRP2, 3, 4, 5; LEU1, 4, MET2,3,4,8,9,14,16,19; URA1,2,4,5,10; HOM3,6; ASP3; CHO1; ARO 2, 7, CYS3; OLE1; IN01,2,4; PR01,3 Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In a more complex version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

In appropriate assays, so-called counterselectable or negatively selectable genes may be used. Suitable genes include: URA3 (orotidine-5'-phosphate decarboxylase; inhibits growth on 5-fluoroorotic acid), LYS2 (2-aminoadipate reductase; inhibits growth on a-aminoadipate as sole nitrogen source), CYH2 (encodes ribosomal protein L29; cycloheximide-sensitive allele is dominant to resistant allele), CAN1 (encodes arginine permease; null allele confers resistance to the arginine analog canavanin), and other recessive drug-resistant markers.

In one example, the marker gene effects yeast cell growth. The natural response to signal transduction via the yeast pheromone system response pathway is for cells to undergo growth arrest. This is the preferred way to select for antagonists to a ligand/receptor pair that induces the pathway. An autocrine peptide antagonist would inhibit the activation of the pathway; hence, the cell would be able to grow. Thus, the FAR1 gene may be considered an endogenous counterselectable marker. The FAR1 gene is preferably inactivated when screening for agonist activity.

The marker gene may also be a screenable gene. The screened characteristic may be a change in cell morphology, metabolism or other screenable features. Suitable markers include beta-galactosidase (Xgal, $C_{12}FDG$, Salmon-gal, Magenta-Gal (latter two from Biosynth Ag)), alkaline phosphatase, horseradish peroxidase, exo-glucanase (product of yeast exbl gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate Xgal into a blue pigment. Again, the promoter may be receptor-induced or receptor-inhibited.

XIII. Genetic Markers in Yeast Strains

Yeast strains that are auxotrophic for histidine (HIS3) are known, see Struhl and Hill, (1987) *Mol. Cell. Biol.*, 7:104; Fasullo and Davis, *Mol. Cell. Biol.,* (1988) 8:4370. The HIS3 (imidazoleglycerol phosphate dehydratase) gene has been used as a selective marker in yeast. See Sikorski and Heiter, (1989) Genetics, 122:19; Struhi, et al., P.N.A.S. (1979) 76:1035; and, for FUS1-HIS3 fusions, see Stevenson, et al., (1992) *Genes Dev.,* 6:1293.

XIV. Novel FPRL-1 Ligand

Yet another aspect of the invention pertains to a novel ligand for the orphan receptor, FPRL-1. As described in Example 8, a tridecapeptide having the sequence Ser-Leu-Leu-Trp-Leu-Thr-Cys-Arg-Pro-Trp-Glu-Ala-Met was identified from a polypeptide library on the basis of its ability to act as a surrogate ligand for FPRL-1.

Chemoattractants are important mediators of inflammation, they function to recruit phagocytic cells at the site of injury or infection. They also mediate granule secretion, superoxide generation and upregulation of cell surface adhestion molecules, for example MAC-1. Exemplary chemoattractants include the complement component C5a, interleukin 8, leukotriene B4 and platelet activating factor. Many of these substances participate in pathophysiological conditions such as anaphylaxis and septic shock. The identification of ligands for the orphan FPRL1 receptor provides new opportunities for discovery of receptor agonists, that could potentially serve to enhance lymphocyte recruitment in immunocompromised patients, and for the discovery of receptor antagonists (described supra) that could prevent undesirable consequences of immune activation such as anaphylactic or septic shock.

The term "peptide" is used herein to refer to a chain of two or more amino acids or amino acid analogs (including non-naturally occurring amino acids), with adjacent amino acids joined by peptide (—NHCO—) bonds. Thus, the peptides of the present invention include oligopeptides, polypeptides, and proteins. Preferably, the peptides of the present invention include all or a portion of the S-L-L-W-L-T-C-R-P-W-E-A-M peptide, or a homolog thereof. The peptide (or peptidomimetic) is preferably at least 3 amino acid residues in length, though peptides of up to 13 amino acids, such as 4, 5, 7, 10, 13 or more residues in length, are preferred. Longer peptides which include the FPRL ligand are also contemplated. For example, the sequence derived from the FPRL-1 surrogate ligand can be provided as part of a fusion protein. The minimum peptide length is chiefly dictated by the need to obtain sufficient potency as an activator or inhibitor. Given the size of the peptide isolated in subject assay, smaller fragments of the tridecapeptide which retain receptor binding activity will be easily identified, e.g., by chemical synthesis of different fragments. The maximum peptide length will only be a function of synthetic convenience once an active peptide is identified.

The invention also provides for the generation of mimetics, e.g. peptide or non-peptide agents. Moreover, the present invention also contemplates variants of the subject polypeptide which may themselves be either agonistic or antagonistic of the S-L-L-W-L-T-C-R-P-W-E-A-M peptide. Thus, using such mutagenic techniques as known in the art, the determinants of S-L-L-W-L-T-C-R-P-W-E-A-M polypeptide which participate in FPRL-1 interactions can be ellucidated. To illustrate, the critical residues of a subject polypeptide which are involved in molecular recognition of an FPRL-1 receptor can be determined and used to generate variant polypeptides which competitively inhibit binding of the authentic S-L-L-W-L-T-C-R-P-W-E-A-M peptide with that receptor. By employing, for example, scanning mutagenesis to map the amino acid residues of the polypeptide involved in binding the FPRL-1 receptor, peptide and peptidomimetic compounds can be generated which mimic those residues in binding to the receptor and which consequently can inhibit binding of an authentic ligand for the FPRL-1 receptor and interfere with the fuinction of that receptor.

Moreover, as is apparent from the present and parent disclosures, mimetopes of the subject S-L-L-W-L-T-C-R-P-W-E-A-M peptide can be provided as non-hydrolyzable peptide analogs. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p123), C-7 mimics (Huffinan et al. in Peptides: Chemistry and Biologyy, G. R. Marshall ed., ESCOM Publisher: Leiden, Netherlands, 1988, p. 105), keto-methylene pseudopeptides (Ewenson et al. (1986) J. Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J. Chem Soc Perkin Trans 1:1231), β-aminoalcohols (Gordon et al. (1985) Biochem Biophys Res Communl26:419; and Dann et al. (1986) Biochem Biophys Res Commun 134:71), diaminoketones (Natarajan et al. (1984) Biochem Biophys Res Commun 124:141), and methyleneamino-modifed (Roark et al. in Peptides: Chemistry and Biology, G. R. Marshall ed., ESCOM Publisher: Leiden, Netherlands, 1988, p134). Also, see generally, Session III: Analytic and synthetic methods, in in Peptides: Chemistry and Biology, G. R. Marshall ed., ESCOM Publisher: Leiden, Netherlands, 1988)

In an exemplary embodiment, the peptidomimetic can be derived as a retro-inverso analog of the peptide. To illustrate, the S-L-L-W-L-T-C-R-P-W-E-A-M peptide can be generated as the retro-inverso analog:

Such retro-inverso analogs can be made according to the methods known in the art, such as that described by the Sisto et al. U.S. Pat. No. 4,522,752. For example, the illustrated retro-inverso analog can be generated as follows. The geminal diamine corresponding to the serine analog is synthesized by treating a protected serine with ammonia under HOBT-DCC coupling conditions to yield the N-Boc amide, and then effecting a Hofmann-type rearrangement with I,I-bis-(trifluoroacetoxy)iodobenzene (TIB), as described in Radhakrishna et al. (1979) J. Org. Chem. 44:1746. The product amine salt is then coupled to a side-chain protected (e.g., as the benzyl ester) N-Fmoc D-Leu residue under standard conditions to yield the pseudodipeptide. The Fmoc (fluorenylmethoxycarbonyl) group is removed with piperidine in dimethylformamide, and the resulting amine is trimethylsilylated with bistrimethylsilylacetamide (BSA) before condensation with suitably alkylated, side-chain protected derivative of Meldrum's acid, as described in U.S. Pat. No. 5,061,811 to Pinori et al., to yield the retro-inverso tripeptide analog S-L-L. The pseudotripeptide is then coupled with L-Trp under standard conditions to give the protected tetrapeptide analog. The protecting groups are removed to release the product, and the steps repeated to enlogate the tetrapeptide to the full length peptide. It will be understood that a mixed peptide, e.g. including some normal peptide linkages, can be generated. As a general guide, sites which are most susceptible to proteolysis are typically altered, with less susceptible amide linkages being optional for mimetic switching The final product, or intermediates thereof, can be purified by HPLC.

In another illustrative embodiment, the peptidomimetic can be derived as a retro-enatio analog of the peptide, such as the exemplary retro-enatio peptide analog derived for the illustrative S-L-L-W-L-T-C-R-P-W-E-A-M peptide:

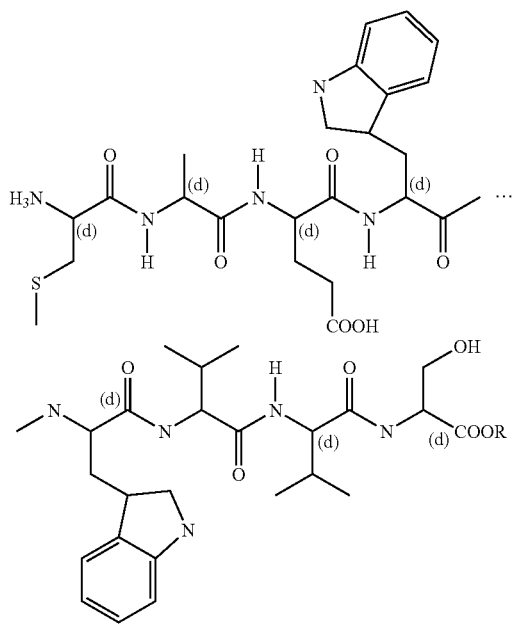

NH₃-(d) Met-(d) Ala-(d) Glu-(d)Trp . . . (d) Trp-(d) Leu-(d)-Leu-(d) Ser

Retro-enantio analogs such as this can be synthesized using commercially available D-amino acids and standard solid- or solution-phase peptide-synthesis techniques. For example, in a preferred solid-phase synthesis method, a suitably amino-protected (t-butyloxycarbonyl, Boc) D-Serine residue (or analog thereof) is covalently bound to a solid support such as chloromethyl resin. The resin is washed with dichloromethane (DCM), and the BOC protecting group removed by treatment with TFA in DCM. The resin is washed and neutralized, and the next Boc-protected D-amino acid (D-Leu) is introduced by coupling with diisopropylcarbodiimide. The resin is again washed, and the cycle repeated for each of the remaining amino acids in turn (D-Leu, D-Trp etc). When synthesis of the protected retro-enantio peptide is complete, the protecting groups are removed and the peptide cleaved from the solid support by treatment with hydrofluoric acid/anisole/dimethyl sulfide/thioanisole. The final product is purified by HPLC to yield the pure retro-enantio analog.

In still another illustrative embodiment, trans-olefin derivatives can be made for the subject polypeptide. For example, an exemplary olefin analog is derived for the illustrative S-L-L-W-L-T-C-R-P-W-E-A-M peptide:

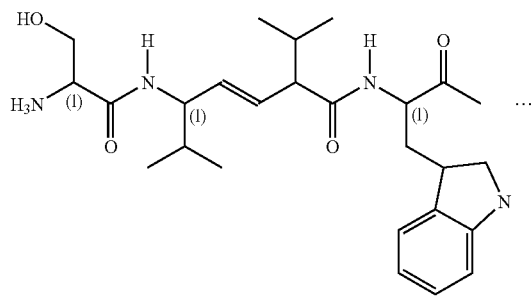

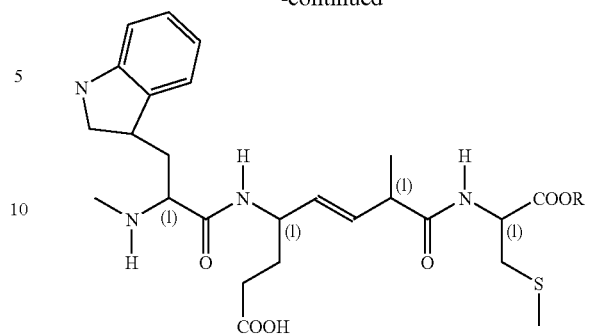

The trans olefin analog of the subject peptide can be synthesized according to the method of Y. K. Shue et al. (1987) Tetrahedron Letters 28:3225.

Still another class of peptidomimetic derivatives include the phosphonate derivatives, such as the partially phosphonate derivatived S-L-L-W-L-T-C-R-P-W-E-A-M peptide:

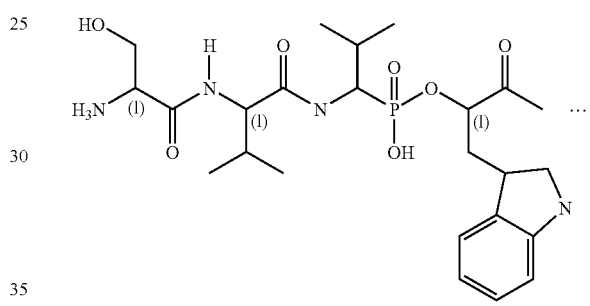

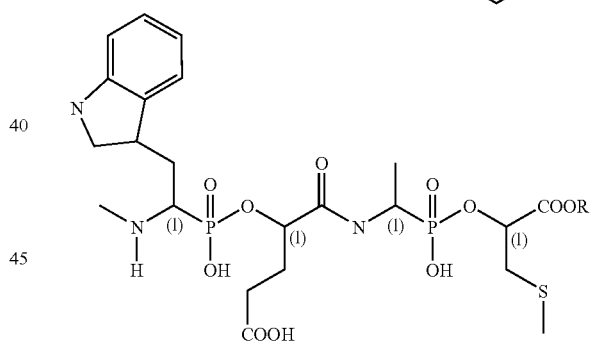

The synthesis of such phosphonate derivatives can be adapted from known synthesis schemes. See, for example, Loots et al. in Peptides: Chemistry and Biology, (Escom Science Publishers, Leiden, 1988, p. 118); Petrillo et al. in Peptides: Structure and Function (Proceedings of the 9th American Peptide Symposium, Pierce Chemical Co. Rockland, Ill., 1985).

XV. Novel C5a Ligands

Still another aspect of the invention pertains to a novel ligand for the C5a receptor. As described in Example 12, several 13-mer and 11-mer peptides have been identified from a polypeptide library on the basis of their ability to act as surrogate ligands for the C5a receptor. The sequence for exemplary C5a receptor ligands is provided in FIG. 7. Yet another preferred C5a ligand includes all or a portion of the peptide Asp-Thr-Arg-Ser-Trp-Lys-Leu-Arg-Leu-Leu-Trp-Leu-Ala, described in the appended examples.

The importance of the C5a receptor finds its origin in its relationship with complement derived C5a and its role in the overall immune response. In man, and in most animals, the complement system is composed of a group of proteins that are normally present in serum in an inactive state. When activated, these proteins participate in a coordinated series of reactions. Activation of the complement system results in enzymatic cleavage of complement proteins producing subfragments which possess a wide range of biologic activities required for host defense, including bloodclotting and inflammatory responses, as well as activation of immune response directed to the elimination of invading microorganisms. During an inflammatory process, local production of complement-derived mediators result in increased vascular permeability, leukocyte adherence to endothelial and vascular tissue, and a chemotactic gradient that induces neutrophil (PMN) migration into the inflammatory site. In addition to beneficial aspects of the inflammatory process, systemic and/or chronic inflammatory processes have been associated with a variety of immune disease states. The anaphylatoxin C5a is one of the best described and most potent proinflammatory mediators derived from the complement system. C5a has been shown to be spasmogenic (Stimler et al. (1981) *J. Immunol.* 126:2258), chemotactic (Hugli et al. (1978) *Adv. Immunol.* 26:1), to increase vascular permeability (Shin et al. (1968) *Science* 162:361), and to induce the release of pharmacologically active mediators from numerous cell types (Grant et al. (1975) *J. Immunol.* 114:1101; Goldstein et al. (1973) *J. Immunol.* 113:1583; Schorlemmer et al. (1976) Nature 261:48). Most recently, CSa has been shown to directly or indirectly induce cytokine release from macrophages and to augment humoral- and cell-mediated immune responses in vitro. Combined, these studies indicate that C5a possesses multiple biologic activities important in host defense and may also play a role in inflammatory disease processes. Many cell types possess receptors for C5a, including PMNs, macrophages, mast cells and platelets.

Among the various cell types, the neutrophil response to C5a is the best defined. Cell surface receptors specific for C5a have been demonstrated on the neutrophil (Chenoweth et al. (1978) *PNAS* 75:3943; Huey et al. (1985) *J. Immunol* 135:2063; Rollins et al. (1985) *J. Biol.Chem.* 260:7157), and the ligand-receptor interaction has been shown to promote human polymorphonuclear leukocyte (PMN) migration in a directed fashion (chemotaxis), adherence, oxidative burst, and granular enzyme release from these cells (Hugli et al. (1984) *Springer Semin. Immunopathol.* 7:193). The interaction of C5a with PMN and other target cells and tissues results in increased histamine release, vascular permeability, smooth muscle contraction, and an influx into tissues of inflammatory cells, including neutrophils, eosinophils, and basophils (Hugli et al., supra). C5a may also be important in mediating inflammatory effects of phagocytic mononuclear cells that accumulate at sites of chronic inflammation (Allison et al. (1978) Agents and Actions 8:27). C5a and C5a des-Arg can induce chemotaxis in monocytes (Ward et al. (1968) *J. Exp. Med.* 128:1201. Snyderman et al. (1979) *J. Immunol.*109:896) and cause them to release lysosomal enzymes in a manner analogous to the neutrophil responses elicited by these agents. Other studies suggest that C5a may have an immunoregulatory role by enhancing antibody particularly at sites of inflammation (Morgan et al. (1982) *J. Exp. Med.* 155:1412; Weigle et al. (1982) *Federation Proc.* 41:3099; and Morgan et al. (1984) *Federation Proc.* 43:2543).

Accordingly, the peptides identified by the instant assay as C5a ligands can be used therapeutically to enhance inflammatory responses. As above, the term "peptide" is used herein to refer to a chain of two or more amino acids or amino acid analogs (including non-naturally occurring amino acids), with adjacent amino acids joined by peptide (—NHCO—) bonds. Thus, the peptides of the present invention include oligopeptides, polypeptides, and proteins. The peptide (or peptidomimetic) is preferably at least 3 amino acid residues in length, though peptides of any length up to 13, including peptides of 4, 5, 7, 10, 13 or more residues in length are preferred. Longer peptides are also specifically contemplated. For example, the sequence derived from the C5a surrogate ligand can be provided as part of a fusion protein. The minimum peptide length is chiefly dictated by the need to obtain sufficient potency and selectivity as an activator or inhibitor. Given the size of the peptide isolated in subject assay, smaller fragments of the 11-mer and 13-mer peptides which retain C5a receptor binding activity will be easily identified, e.g., by chemical synthesis of different fragments. The maximum peptide length will only be a function of synthetic convenience once an active peptide is identified.

The invention also provides for the generation of mimetics, e.g. peptide or non-peptide agents, of the subject C5a receptor ligands. Moreover, the present invention also contemplates variants of the subject C5a ligands which may themselves be either agonistic or antagonistic of the C5a receptor activity. Thus, using such mutagenic techniques as known in the art, the determinants of peptide which participate in interaction with the C5a receptor can be ellucidated. To illustrate, the critical residues of a subject polypeptide which are involved in molecular recognition of a C5a receptor can be determined and used to generate variant polypeptides which competitively inhibit binding of the original peptide with that receptor. By employing, for example, scanning mutagenesis to map the amino acid residues of the polypeptide involved in binding the C5a receptor, peptide and peptidomimetic compounds can be generated which mimic those residues in binding to the receptor and which consequently can inhibit binding of an authentic ligand for the C5a receptor and interfere with the function of that receptor. Such C5a receptor antagonists can be useful as inhibitors of inflammation, e.g., in the treatment of anaphylaxis.

Moreover, as is apparent from the present and parent disclosures, mimetopes of the subject C5a ligands can be provided as non-hydrolyzable peptide analogs. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p123), C-7 mimics (Huffinan et al. in Peptides: Chemistry and Biologyy, G. R. Marshall ed., ESCOM Publisher: Leiden, Netherlands, 1988, p. 105), keto-methylene pseudopeptides (Ewenson et al. (1986) J. Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J. Chem Soc Perkin Trans 1:1231), βaminoalcohols (Gordon et al. (1985) Biochem Biophys Res Commun126:419; and Dann et al. (1986) Biochem Biophys Res Commun 134:71), diaminoketones (Natarajan et al. (1984) Biochem Biophys Res Commun 124:141), and methyleneamino-modifed (Roark et al. in Peptides: Chemistry and Biology, G. R. Marshall ed., ESCOM Publisher: Leiden, Netherlands, 1988, p134). Also, see generally, Session III: Analytic and synthetic methods, in in Peptides: Chemistry and Biology, G. R. Marshall ed., ESCOM Publisher: Leiden, Netherlands, 1988).

XVI. Further Manipulation of Peptide Ligands

The above examples provide guidance for a variety of techniques for manipulating peptide ligands indentified in the present screening assay in order to develop more specific and/or potent agonists or antagonists. In addition, a variety of combinatorial techniques are known in the art and will be useful for further optimization of the peptide leads coming of the instant assay. For example, alanine scanning mutagenesis and the like (Lowman et al. (1991) *Biochemistry* 30:10832–10838; and Cunningham et al. (1989) *Science* 244:1081–1085), by linker scanning mutagenesis (Brown et al. (1992) *Mol. Cell Biol.*12:2644–2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11–19); or by random mutagenesis (Miller et al. (1992) *A Short Course in Bacterial Genetics*, CSHL Press, Cold Spring Harbor, N.Y.) can be used to create libraries of variants which can be further screened, even by simple receptor binding assays, for receptor binding activity. To further illustrate the state of the art, it is noted that the review article of Gallop et al. (1994) *J Med Chem* 37:1233 describe the general state of the art of combinatorial libraries. In particular, Gallop et al state at page 1239 "[s]creening the analog libraries aids in determining the minimum size of the active sequence and in identifying those residues critical for binding and intolerant of substitution".

For the most part, the amino acids used in the subject receptor agonists and antagonists of this invention will be those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

However, the term amino acid residue further includes analogs, derivatives and congeners of any specific amino acid referred to herein. For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject peptidomimetic can include an amino acid analog as for example, b-cyanoalanine, canavanine, djenkolic acid, norleucine, 3-phosphoserine, homoserine, dihydroxyphenylalanine, 5-hydroxytryptophan, 1-methylhistidine, or 3-methylhistidine. Other naturally occurring amino acid metabolites or precursors having side chains which are suitable herein will be recognized by those skilled in the art and are included in the scope of the present invention.

Also included are the D and L stereoisomers of such amino acids when the structure of the amino acid admits of stereoisomeric forms. The configuration of the amino acids and amino acid residues herein are designated by the appropriate symbols D, L or DL, furthermore when the configuration is not designated the amino acid or residue can have the configuration D, L or DL. It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis. For the purposes of this application, unless expressly noted to the contrary, a named amino acid shall be construed to include both the D or L stereoisomers, preferably the L stereoisomer.

XVII. Pharmaceutical Preparations of Identified Agents

After identifying certain test compounds as potential surrogate ligands, or receptor antagonists, the practioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The compounds selected in the subject assay, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

EXEMPLIFICATION

The invention now being generally described will be more readily understood by reference to the following examples, which are included merely for purposes of illustration of certain aspects and embodiments of the present invention and are not intended to limit the invention.

Example 1

Development of Autocrine Yeast Strains

In this example, we describe a pilot experiment in which haploid cells were engineered to be responsive to their own pheromones. (Note that in the examples, functional genes are capitalized and inactivated genes are in lower case.) For this purpose we constructed recombinant DNA molecules designed to:

i. place the coding region of STE2 under the transcriptional control of elements which normally direct the transcription of STE3. This is done in a plasmid that allows the replacement of genomic STE3 of *S. cerevisiae* with sequences wherein the coding sequence of STE2 is driven by STE3 transcriptional control elements.

ii. place the coding region of STE3 under the transcriptional control of elements which normally direct the transcription of STE2. This is done in a plasmid which will allow the replacement of genomic STE2 of *S. cerevisiae* with sequences wherein the coding sequence of STE3 is driven by STE2 transcriptional control elements.

The sequence of the STE2 gene is known see Burkholder A. C. and Hartwell L. H. (1985), *Nuc. Acids Res.* 13, 8463; Nakayama N., Miyajima A., Arai K. (1985) *EMBO J.* 4, 2643.

A 4.3 kb BamHI fragment that contains the entire STE2 gene was excised from plasmid YEp24-STE2 (obtained from J. Thomer, Univ. of California) and cloned into pAL-TER (Protocols and Applications Guide, 1991, Promega Corporation, Madison, Wis.). An SpeI site was introduced 7 nucleotides (nts) upstream of the ATG of STE2 with the following mutagenic oligonucleotide, using the STE2 minus strand as template:

A second SpeI site was simultaneously introduced just downstream of the STE2 stop codon with the following mutagenic oligonucleotide:

The BamHI fragment of the resulting plasmid (Cadus 1096) containing STE2 with SpeI sites immediately flanking the coding region, was then subcloned into the yeast integrating vector YIp19 to yield Cadus 1143.

The STE3 sequence is also known (Nakayama N., Miyajima A., Arai K. (1985), *EMBO J.* 4, 2643; (Hagen D. C., McCaffrey G., Sprague G. F. (1986), *Proc. Natl. Acad. Sci.* 83, 1418. STE3 was made available by Dr. J. Broach as a 3.1 kb fragment cloned into pBLUESCRIPT-KS II (Stratagene, 11011 North Torrey Pines Road, La Jolla, Caif. 92037). STE3 was subcloned as a KpnI-XbaI fragment into both M13mpl8 RF (to yield Cadus 1105 and pUC19 (to yield Cadus 1107). The two SpeI sites in Cadus 1107 were removed by digestion with SpeI, fill-in with DNA polymerase I Klenow fragment, and recircularization by blunt-end ligation. Single-stranded DNA containing the minus strand of STE3 was obtained using Cadus 1105 and SpeI sites were introduced 9 nts upstream of the start codon and 3 nts downstream of the stop codon of STE3 with the following mutagenic oligonucleotides, respectively:

The mutagenesis was accomplished using the T7-GEN protocol of United States Biochemical (T7-GEN In Vitro Mutagenesis Kit, Descriptions and Protocols, 1991, United States Biochemical, P.O. Box 22400, Cleveland, Ohio 44122). The replicative form of the resulting Cadus 1141 was digested with AflII and KpnI, and the approximately 2 kb fragment containing the entire coding region of STE3 flanked by the two newly introduced Spe I sites was isolated and ligated with the approximately 3.7 kb vector fragment of AflII- and KpnI-digested Cadus 1107, to yield Cadus 1138. Cadus 1138 was then digested with XbaI and KpnI, and the STE3-containing 2.8 kb fragment was ligated into the XbaI- and KpnI-digested yeast integrating plasmid pRS406 (Sikorski, R. S. and Hieter, P. (1989), *Genetics* 122:19–27) to yield Cadus 1145.

The SpeI fragment of Cadus 1143 was replaced with the SpeI fragment of Cadus 1145 to yield Cadus 1147, in which the coding sequences of STE3 are under the control of STE2 expression elements. Similarly, the SpeI fragment of Cadus 1145 was replaced with the SpeI fragment of Cadus 1143 to yield Cadus 1148, in which the coding sequences of STE2 are under the control of STE3 expression elements. Using the method of pop-in/pop-out replacement (Rothstein, R. (1991) *Methods in Enzymology*, 194:281 301), Cadus 1147 was used to replace genomic STE2 with the ste2-STE3 hybrid in a MATa cell and Cadus 1148 was used to replace genomic STE3 with the ste3-STE2 hybrid in a MATα cell. Cadus 1147 and 1148 contain the selectable marker URA3.

Haploid yeast of mating type a which had been engineered to express HIS3 under the control of the pheromone-inducible FUS1 promoter were transformed with CADUS 1147, and transformants expressing URA3 were selected. These transformants, which express both Ste2p and Ste3p, were plated on 5-fluoroorotic acid to allow the selection of clones which had lost the endogenous STE2, leaving in its place the heterologous, integrated STE3. Such cells exhibited the ability to grow on media deficient in histidine, indicating autocrine stimulation of the pheromone response pathway.

Similarly, haploids of mating type a that can express HIS3 under the control of the pheromone-inducible FUSI promoter were transformed with CADUS 1148 and selected for replacement of their endogenous STE3 with the integrated STE2. Such cells showed, by their ability to grow on histidine-deficient media, autocrine stimulation of the pheromone response pathway.

Example 2

Strain Development

In this example, yeast strains are constructed which will facilitate selection of clones which exhibit autocrine activation of the pheromone response pathway. To construct appropriate yeast strains, we will use: the YIp-STE3 and pRS-STE2 knockout plasmids described above, plasmids available for the knockout of FAR1, SST2, and HIS3, and mutant strains that are commonly available in the research community. The following haploid strains will be constructed, using one-step or two-step knockout protocols described in *Meth. Enzymol* 194:281–301, 1991:

| | | | | | | | | | | |
|---|---|---|---|---|---|---|---|---|---|---|
| 1. | MATα | | ste3::STE2::ste3 | far1 | sst2 | FUS1::HIS3 | | | | |
| 2. | MATα | | ste2::STE3::ste2 | far1 | sst2 | FUS1::HIS3 | | | | |
| 3. | MATα | | ste3::STE2::ste3 | far1 | sst2 | mfα1 mfα2 | | FUS1::HIS3 | | |
| 4. | MATa | | ste2::STE3::ste2 | far1 | sst2 | mfa1 mfa2 | | FUS1::HIS3 | | |
| 5. | MATa | bar1 | far1-1 | fus1-HIS3 | ste14::TRP1 | ura3 | | trp1 | leu2 | his3 |
| 6. | MATa | mfa1 | mfa2 | far1-1 | his3::fus1-HIS3 | ste2-STE3 | ura3 | met1 | ade1 | leu2 |

Strains 1 and 2 will be tested for their ability to grow on histidine-deficient media as a result of autocrine stimulation of their pheromone response pathways by the pheromones which they secrete. If these tests prove successful, strain 1 will be modified to inactivate endogenous MFα1 and MFα2. The resulting strain 3, MATα far1 sst2 ste3::STE2::ste3 FUS1::HIS3 mfal mfa2, should no longer display the selectable phenotype (i.e., the strain should be auxotrophic for histidine). Similarly, strain 2 will be modified to inactivate endogenous MFa1 and MFa2. The resulting strain 4, AMTa far1 sst2 ste2::STE3::ste2 FUS1::HIS3 mfal mfa2, should be auxotrophic for histidine. The uses of strains 5 and 6 are outlined in Examples 3 and 4 below.

Example 3

Peptide Library

In this example, a synthetic oligonucleotide encoding a peptide is expressed so that the peptide is secreted or transported into the periplasm.

i. The region of MFα1 which encodes mature a-factor has been replaced via single-stranded mutagenesis with restriction sites that can accept oligonucleotides with AflII and BglII ends. Insertion of oligonucleotides with AflII and BglII ends will yield plasmids which encode proteins containing the MFα1 signal and leader sequences upstream of the sequence encoded by the oligonucleotides. The MFα1 signal and leader sequences should direct the processing of these precursor proteins through the pathway normally used for the transport of mature α-factor.

The MFα1 gene, obtained as a 1.8 kb EcoRI fragment from pDA6300 (J. Thorner, Univ. of California) was cloned into pALTER in preparation for oligonucleotide-directed mutagenesis to remove the coding region of mature a-fictor while constructing sites for acceptance of oligonucleotides with AflII and BclI ends. The mutagenesis was accomplished using the minus strand as template and the following mutagenic oligonucleotide:

5'-CTAAAGAAGAAGGGGTATCTTTGCTTAAGCTCGAGATCTCGACTGA

TAACAACAGTGTAG-3'

A HindIII site was simultaneously introduced 7 nts upstream of the MFα1 start codon with the oligonucleotide:

5' CATACACAATATAAAGCTTTAAAAGAATGAG-3'

The resulting plasmid, Cadus 1214, contains a HindIII site 7 nts upstream of the MFα1 initiation codon, an AflII site at the positions which encode the KEX2 processing site in the MFα1 leader peptide, and XhoI and BglII sites in place of all sequences from the leader-encoding sequences up to and including the normal stop codon. The 1.5 kb HindIII fragment of Cadus 1214 therefore provides a cloning site for oligonucleotides to be expressed in yeast and secreted through the pathway normally travelled by endogenous α-factor.

A sequence comprising the ADC1 promoter and 5' flanking sequence was obtained as a 1.5 kb BamHI-HindIII fragment from pAAH5 (Ammerer, G. (1983) Academic Press, Inc., Meth. Enzymol. 101, 192–201 and ligated into the high copy yeast plasmid pRS426 (Christianson, T. W et al. (1992) *Gene* 110:119–122) (see FIG. 1). The unique XhoI site in the resulting plasmid was eliminated to yield Cadus 1186. The 1.5 Kb HindIII fragment of Cadus 1214 was inserted into HindIII-digested Cadus 1186; expression of sequences cloned into this cassette initiates from the ADH1 promoter. The resulting plasmid, designated Cadus 1215, can be prepared to accept oligonucleotides with AflII and BclI ends by digestion with those restriction endonucleases. The oligonucleotides will be expressed in the context of MF al signal and leader peptides (FIG. 2).

Modified versions of Cadus 1215 were also constructed. To 30 improve the efficiency of ligation of oligonucleotides into the expression vector, Cadus 1215-was restricted with KpnI and religated to yield Cadus 1337. This resulted in removal of one of two HindIII sites. Cadus 1337 was linearized with HindIII, filled-in, and recircularized to generate Cadus 1338. To further tailor the vector for library construction, the following double-stranded oligonucleotide was cloned into AflII-and BglII-digested Cadus 1338:

5' TTAAGCGTGAGGCAGAAGCTTATCGATA     oligo 062

3' CGCACTCCGTCTTCGAATAGCTATCTAG     oligo 063

The ClaI site is unique in the resulting vector, Cadus 1373. In Cadus 1373, the HindIII site that exists at the junction between the MFα pro sequence and the mature peptide to be expressed by this vector was made unique. Therefore the HindIII site and the downstream BglII site can be used to insert oligo-nucleotides encoding peptides of interest. These modifications of Cadus 1215 provide an alternative to the use of the AflII site in the cloning of oligonucleotides into the expressions vector.

Cadus 1373 was altered further to permit elimination from restricted vector preparations of contaminating singly-cut plasmid. Such contamination could result in unacceptably high background transformation. To eliminate this possibility, approximately 1.1 kb of dispensable ADH1 sequence at the 5' side of the promoter region was deleted. This was accomplished by restriction of Cadus 1373 with SphI and BamHII, fill-in, and ligation; this maneuver regenerates the BamHI site. The resulting vector, Cadus 1624, was then restricted with HindIII and ClaI and an approximately 1.4 kb HindIII and ClaI fragment encoding 25 lacZ was inserted to generate Cadus 1625. Use of HindIII- and BglII-restricted Cadus 1625 for acceptance of oligonucleotides results in a low background upon transformation of the ligation product into bacteria.

Two single-stranded oligonucleotide sequences (see below) are synthesized, annealed, and repetitively filled in, denatured, and reannealed to form double-stranded oligonucleotides that, when digested with AflII and BclI, can be ligated into the polylinker of the expression vector, Cadus 1215. The two single-stranded oligonucleotides have the following sequences:

5'-G CTA CTT AAG CGT GAG GCA GAA GCT 3' and

5'-C GGA TGA TCA (NNN)$_n$ AGC TTC TGC CTC ACG CTT AAG TAG C 3' where N is any chosen nucleotide and n is any chosen integer. Yeast transformed with the resulting plasmids will secrete—through the α-factor secretory pathway—peptides whose amino acid sequence is determined by the particular choice of N and n).

Alternatively, the following single stranded oligonucleotides are used:
MFαNNK (76 mer):

5'CT<u>GGATG</u>CGAAGACAGCTNNKNNKNNKNNKNNKNNKNNKNNKNNKNNK NNKNNK TGATCAGTCTGTGACGC 3' and MFαMbo (17 mer):

5' GCGTCACAGACTGATCA 3'

When annealed the double stranded region is:

TGA<i>T</i>CAGTCTGTGACGC
ACTAGTCAGACACTGCG

After fill-in using Taq DNA polymerase (Promega Corporation, Madison, Wis.), the double stranded product is restricted with BbsI and MboI and ligated to HindIII- and BglII-restricted Cadus 1373.

ii. The region of MFα1 which encodes mature a-factor will be replaced via single stranded mutagenesis with restriction sites that can accept oligonucleotides with XhoI and AflII ends. Insertion of oligonucleotides with XhoI and AflII ends will yield plasmids which encode proteins containing the MFa1 leader sequences upstream of the sequence encoded by the oligonucleotides. The MFa1 leader sequences should direct the processing of these precursor proteins through the pathway normally used for the transport of mature a-factor. MFA1, obtained as a BamHI fragment from pKK1 (provided by J. 30 Thomer and K. Kuchler), was ligated into the BamHI site of pALTER (Promega). Using the minus strand of MFA1 as template, a HindIII site was inserted by oligonucleotide-directed mutagenesis just 5' to the MFA1 start codon using the following oligonucleotide:

5' CCAAAATAAGTACAAAGCTTTCGAATAGAAATGCAACCATC

A second oligonucleotide was used simultaneously to introduce a short polylinker for later cloning of synthetic oligonucleotides in place of MFA1 sequences. These MFA1 sequences encode the C-terminal 5 amino acids of the 21 amino acid leader peptide through to the stop codon:

5'GCCGCTCCAAAAGAAAAGACCTCGAGCTCGCTTAAGTTCTGCGTACAA AAACGTTGTTC 3'

Figure 3:
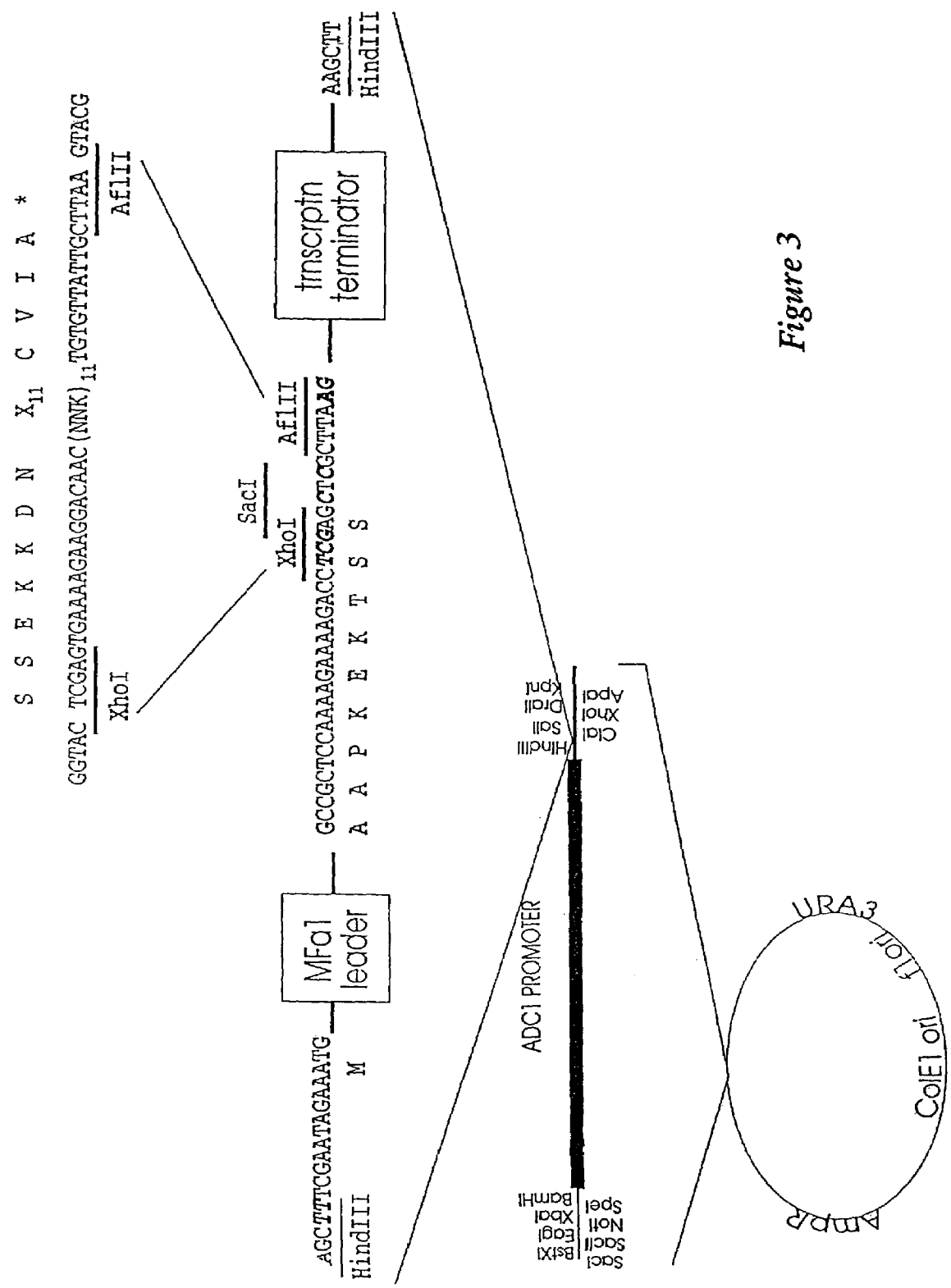
FIG. 3. Schematic diagram of the structure of the plasmid resulting from insertion of random oligonucleotides into pADC-MFa. This plasmid expresses random peptides in the context of the MFa1 leader and C-terminal CVIA tetrapeptide.

The 1.6 kb HindIII fragment of the resulting plasmid, Cadus 1172, contains sequences encoding the MFA1 start codon and the N-terminal 16 amino acids of the leader peptide, followed by a short polylinker containing XhoI, SacI, and AflII sites for insertion of oligonucleotides. The 1.6 kb HindIII fragment of Cadus 1172 was ligated into HindIII-digested Cadus 1186 (see above) to place expression of sequences cloned into this cassette under the control of the ADH1 promoter. The SacI site in the polylinker was made unique by eliminating a second SacI site present in the vector. The resulting plasmid, designated Cadus 1239, can be prepared to accept oligonucleotides with XhoI and AflII ends by digestion with those restriction endonucleases for expression in the context of MFa1 leader peptides (FIG. 3).

Two single-stranded oligonucleotide sequences (see below) are synthesized, annealed, and repetitively filled in, denatured, and reannealed to form double-stranded oligonucleotides that, when digested with AflII and BglII, can be cloned into the polylinker of the expression vector, Cadus 1239. The two single-stranded oligonucleotides used for the cloning have the following sequences:

5' GG TAC TCG AGT GAA AAG AAG GAC AAC 3'

5' CG TAC TTA AGC AAT AAC ACA (NNN)$_n$ GTT GTC CTT CTT TTC ACT CGA GTA CC 3' where N is any chosen nucleotide and n is any chosen integer.

Yeast transformed with the resulting plasmids will transport—through the pathway normally used for the export of a-factor—farnesylated, carboxymethylated peptides whose amino acid sequence is determined by the particular choice of N and n (FIG. 3).

Example 4

Peptide Secretion/Transport

This example demonstrates the ability to engineer yeast such that they secrete or transport oligonucleotide-encoded peptides (in this case their pheromones) through the pathways normally used for the secretion or transport of endogenous pheromones.

Autocrine MATa Strain CY588:

A MATa strain designed for the expression of peptides in the context of MFα1 (i.e., using the MFα1 expression vector, Cadus 1215) has been constructed. The genotype of this strain, which we designate CY588, is MATα bar1 far1-1 fus1-HIS3 ste14::TRP1 ura3 trp1 leu2 his3. The bam mutation eliminates the strain's ability to produce a protease that degrades α-factor and that may degrade some peptides encoded by the cloned oligonucleotides; the far1 mutation abrogates the arrest of growth which normally follows stimulation of the pheromone response pathway; an integrated FUS1-HIS3 hybrid gene provides a selectable signal of activation of the pheromone response pathway; and, finally, the ste14 mutation lowers background of the FUS1-HIS3 readout. The enzymes responsible for processing of the MFa1 precursor in MATα cells are also expressed in MATa cells (Sprague and Thorner, in *The Molecular and Cellular Biology of the Yeast Saccharomyces: Gene Expression*, 1992, Cold Spring Harbor Press), therefore, CY588 cells should be able to secrete peptides encoded by oligonucleotides expressed from plasmid Cadus 1215.

A high transforming version (tbt1-1) of CY588 was obtained by crossing CY1013 (CY588 containing an episomal copy of the STE14 gene) (MATa bar1::hisGfar1-1 fus1-HIS3 ste14::TRP1 ura3 trp1 leu2 his3 [STE14 URA3 CEN4] to CY793 (MATα~tbt1-1 ura3 leu2 trp1 his3 fus1-HIS2 can1 ste114::TRP1 [FUS1 LEU2 2 μ]) and selecting from the resultant spores a strain possessing the same salient genotype described for CY588 (see above), and in addition the tbl-1 allele, which confers the capacity for very high efficiency transformation by electroporation. The selected strain is CY1455 (MA Tabar1::hisGfar1-1 fus1-HIS3 ste14::TRP1 tbt-1 ura3 trp1 leu2 his3).

Secretion of Peptides in the Context of Yeast α-factor:

Experiments were performed to test: 1. the ability of Cadus 1215 to function as a vector for the expression of peptides encoded by synthetic oligonucleotides; 2. the suitability of the oligonucleotides, as designed, to direct the secretion of peptides through the a-factor secretory pathway; 3. the capacity of CY588 to secrete those peptides; and 4. the ability of CY588 to respond to those peptides that stimulate the pheromone response pathway by growing on selective media. These experiments were performed using an oligonucleotide which encodes the 13 amino acid α-factor; i.e., the degenerate sequence $(NNN)_n$ in the oligonucleotide cloned into Cadus 1215 (see above) was specified (n=13) to encode this pheromone. CY588 was transformed with the resulting plasmid (Cadus 1219), and transformants selected on uracil-deficient medium were transferred to histidine-deficient medium supplemented with a range of concentrations of aminotriazole (an inhibitor of the HIS3 gene product that serves to reduce background growth). The results demonstrate that the synthetic oligo-nucleotide, expressed in the context of MFα1 by Cadus 1215, conferred upon CY588 an ability to grow on histidine-deficient media supplemented with aminotriazole. In summation, these data indicate that: 1. CYS88 is competent for the secretion of a peptide encoded by the $(NNN)_n$ sequence of the synthetic oligonucleotide cloned into and expressed from Cadus 1215; and 2. CY588 can, in an autocrine fashion, respond to a secreted peptide which stimulates its pheromone response pathway, in this case by a-factor binding to STE2.

Additional experiments were performed to test the utility of autocrine yeast strains in identifying agonists of the Ste2 receptor from among members of two semi-random α-factor libraries, α-Mid-S and MFα-8.

α-Mid-5 Library

A library of semi-random peptides, termed the a-Mid-S library, was constructed. In this library, the N-terminal four amino acids and the C-terminal four amino acids of a 13 residue peptide are identical to those of native a-factor while the central five residues (residues 5–9) are encoded by the degenerate sequence $(NNQ)_5$. The following oligonucleotides were used in the construction of the α-Mid-5 Library:

(1) MFαMbo, a 17 mer:

5' GCGTCACAGACTGATCA (2) MID5ALF, a 71 mer:

5' GCCGTCAGTAAAGCTTGGCATTGGTTGNNQNNQNNQNNQMMQCAGCC
TATGTACTGATC AGTCTGTGACGC

Sequenase (United States Biochemical Corporation, Cleveland, Ohio) was used to complete the duplex formed after annealing MFαMbo to the MID5ALF oligonucleotide. In the MID5ALF sequence, N indicates a mixture of A, C, G, and T at ratios of 0.8:1:1.3:1; Q indicates a mixture of C and G at a ratio of 1:1.3. These ratios were employed to compensate for the different coupling efficiencies of the bases during oligonucleotide synthesis and were thus intended to normalize the appearance of all bases in the library. The double-stranded oligonucleotide was restricted with HindIII and MboI and ligated to Cadus 1625 (see above); Cadus 1625 had been prepared to accept the semi-random oligonucleotides by restriction with HindIII and BglII.

The apparent complexity of the αMid-5 library is $1 \times 10^7$. This complexity is based on the number of bacterial transformants obtained with the library DNA versus transformants obtained with control vector DNA that lacks insert. Sequence analysis of six clones from the library demonstrated that each contained a unique insert.

To identify peptide members of the α-mid-5 library that could act as agonists on the STE2 receptor, CY1455, a high transforming version of CY588, was electroporated to enhance uptake of α-Mid-5 DNA. Transformants were selected on uracil-deficient (-Ura) synthetic complete medium and were transferred to histidine-deficient (-His) synthetic complete medium supplemented with 0.5 mM or 1 mM aminotriazole.

Yeast able to grow on -His+ aminotriazole medium include (1) yeast which are dependent on the expression of an α-factor variant agonist and (2) yeast which contain mutations that result in constitutive signalling along the pheromone pathway. Yeast expressing and secreting a variant STE2 receptor agonist have the ability to stimulate the growth on -His medium of surrounding CY 1455 cells that do not express such an agonist. Thus a recognizable formation (termed a "starburst") results, consisting of a central colony, growing by virtue of autocrine stimuation of the pheromone pathway, surrounded by satellite colonies, growing by virtue of paracrine stimulation of the pheromone pathway by the agonist peptide as that peptide diffuses radially from the central, secreting colony.

In order to identify the peptide sequence responsible for this "starburst" phenomenon, yeast were transferred from the center of the "starburst" and streaks were made on -Ura medium to obtain single colonies. Individual clones from -Ura were tested for the His+ phenotype on -His+ aminotriazole plates containing a sparse lawn of CY1455 cells. Autocrine yeast expressing a peptide agonist exhibited the "starburst" phenotype as the secreted agonist stimulated the growth of surrounding cells that lacked the peptide but were capable of responding to it. Constitutive pheromone pathway mutants were capable of growth on -His+ aminotriazole but were incapable of enabling the growth of surrounding lawn cells.

Alternatively, streaks of candidate autocrine yeast clones were made on plates containing 5-fluoroorotic acid (FOA) to obtain Ura segregants were retested on -His+ aminotriazole for the loss of the His+ phenotype. Clones that lost the ability to grow on -His+ aminotriazole after selection on FOA (and loss of the peptide-encoding plasmid) derived from candidate expressers of a peptide agonist. The plasmid was rescued from candidate clones and the peptide sequences determined. In addition, a plasmid encoding a putative Ste2 agonist was reintroduced into CY1455 to confirm that the presence of the plasmid encoding the peptide agonist conferred the His+ phenotype to CY1455.

By following the above protocol novel Ste2 agonists have been identified from the α-Mid-5 library. Sequences of nine agonists follow, preceded by the sequence fo the native α-factor pheromone and by the oligonucleotide used to encode the native pheromone in these experiments. (Note the variant codons used in the α-factor-encoding oligonucleotide for glutamine and proline in the C-terminal amino acids of α-factor).

```
5' CTGGATGCGAAGACTCAGCT (20 mer) (oligo060)

5' CGGATGATCA gta cat tgg ttg gcc agg ttt tag ctg caa cca atg cca AGC TGA GTC TTC GCA TCC AG (69 mer) (oligo074)
```

The lower case letters indicate a mixture of 67% of that nucleotide and 11% of each of the other three nucleotides (e.g. t indicates 67% T and 11% A, 11% C, and 11% G). Note that digestion of the double-stranded oligo-nucleotide by FokI or BbsI will yield an identical 5' end that is compatible with HindIII ends.

Oligos 060 and 074 will form the following double-stranded molecule when annealed:

```
α-factor  TGG CAT TGG TTG CAG CTA AAA CCT GGC CAA CCA ATG TAC
encodes   Trp His Trp Leu Gln Leu Lys Pro Gly Gln Pro Met Tyr α-factor
oligo:    TGG CAT TGG TTG CAG CTA AAA CCT GGC CAG CCT ATG TAC
encodes   Trp His Trp Leu Gln Leu Lys Pro Gly Gln Pro Met Tyr M1        TGG CAT TGG TTG TCC TTG TCG CCC GGG CAG CCT ATG TAC
encodes   Trp His Trp Leu Ser Leu Ser Pro Gly Gln Pro Met Tyr M2        TGG CAT TGG TTG TCC CTG GAC GCT GGC CAG CCT ATG TAC
encodes   Trp His Trp Leu Ser Leu Asp Ala Gly Gln Pro Met Tyr M3        TGG CAT TGG TTG ACC TTG ATG GCC GGG CAG CCT ATG TAC
encodes   Trp His Trp Leu Thr Leu Met Ala Gly Gln Pro Met Tyr M4        TGG CAT TGG TTG CAG CTG TCG GCG GGC CAG CCT ATG TAC
encodes   Trp His Trp Leu Gln Leu Ser Ala Gly Gln Pro Met Tyr M5        TGG CAT TGG TTG AGG TTG CAG TCC GGC CAG CCT ATG TAC
encodes   Trp His Trp Leu Arg Leu Gln Ser Gly Gln Pro Met Tyr M6        TGG CAT TGG TTG CGC TTG TCC GCC GGG CAG CCT ATG TAC
encodes   Trp His Trp Leu Arg Leu Gln Ser Gly Gln Pro Met Tyr M7        TGG CAT TGG TTG TCG CTC GTC CCG GGG CAG CCT ATG TAC
encodes   Trp His Trp Leu Ser Leu Val Pro Gly Gln Pro Met Tyr M8        TGG CAT TGG TTG TCC CTG TAC CCC GGG CAG CCT ATG TAC
encodes   Trp His Trp Leu Ser Leu Tyr Pro Gly Gln Pro Met Tyr M9        TGG CAT TGG TTG CGG CTG CAG CCC GGG CAG CCT ATG TAC
encodes   Trp His Trp Leu Arg Leu Gln Pro Gly Gln Pro Met Tyr
```

The nine peptide agonists of the Ste2 receptor above were derived from one electroporation of CY1455 using 1 µg of the α-Mid-5 library DNA. Approximately 3×10⁵ transformants were obtained, representing approximately 0.03% of the sequences present in that library.

MFα-8 Library

A semi-random α-factor library was obtained through synthesis of mutagenized α-factor oligonucleotides such that 1 in 10,000 peptide products were expected to be genuine α-factor. The mutagenesis was accomplished with doped synthesis of the oligonucleotides: each nucleotide was made approximately 68% accurate by synthesizing the following two oligos:

```
5'-CTGGATGCGAAGACTCAGCT

3'-GACCTACGCTTCTGAGTCGA acc gta acc aac gtc gat ttt gga ccg gtt ggt tac atg ACTAGTAGGC-5'
```

The duplex was repetitively filled-in using Taq DNA polymerase (Promega Corporation, Madison, Wis.). The double-stranded product was restricted with BbsI and BclI and ligated into HindIII- and BglII-digested Cadus 1373. The BglII/BclI joint creates a TGA stop codon for the termination of translation of the randomers. Using this approach, the MFα-5.8 library (a library of apparent low complexity based on PCR analysis of oligonucleotide insert frequency) was constructed.

To identify peptide members of the MFα-5.8 library that could act as agonists on the STE2 receptor, CY1455, a high transforming version of CY588, was electroporated to enhance uptake of MFα-5.8 DNA. Transformants were selected on uracil-deficient (-Ura) synthetic complete medium and were transferred to histidine-deficient (-His) synthetic complete medium supplemented with 1.0 mM or 2.5 mM aminotriazole. Yeast from colonies which were surrounded by satellite growth were transferred as streaks to -Ura medium to obtain single colonies. Yeast from single colonies wree then tested for the His+ phenotype on -His+ aminotriazole plates. Sequence analysis of seven of the plasmids rescued from His+ yeast revealed three unique a-factor variants that acted as agonists on the STE2 receptor.

1.4 Independent Clones had the Following Sequence:

```
         TGG CAT TGG CTA CAG CTA ACG CCT GGG CAA CCA ATG TAC
encoding Trp His Trp Leu Gln Leu Thr Pro Gly Gln Pro Met Tyr
```

2.2 Independent Clones had the Following Sequence:

```
         TGG CAT TGG CTG GAG CTT ATG CCT GGC CAA CCA TTA TAC
encoding Trp His Trp Leu Glu Leu Met Pro Gly Gln Pro Leu Tyr 3.       TGG CAT TGG ATG GAG CTA AGA CCT GGC CAA CCA ATG TAC
encoding Trp His Trp Met Glu Leu Arg Pro Gly Gln Pro Met Tyr
```

Autocrine Mata Strain CY599:

A MATa strain designed for the expression of peptides in the context of MFA1 (i.e., using the MFA1 expression vector, Cadus 1239) has been constructed. The genotype of this strain, designated CY599, is AMTa mfa1 mfa2 far1-1 his3::fus1-HIS3 ste2-STE3 ura3 met1 ade1 leu2. In this strain, Cadus 1147 (see above) was used to replace STE2 with a hybrid gene in which the STE3 coding region is under the control of expression elements which normally drive the expression of STE2. As a result, the a-factor receptor replaces the α-factor receptor. The genes which encode a-factor are deleted from this strain; the far1 mutation abrogates the arrest of growth which normally follows stimulation of the pheromone response pathway; and the FUS1-HIS3 hybrid gene (integrated at the HIS3 locus) provides a selectable signal of activation of the pheromone response pathway. CY599 cells were expected to be capable of the transport of a-factor or a-factor-like peptides encoded by oligonucleotides expressed from Cadus 1239 by virtue of expression of the endogenous yeast transporter, Ste6.

Transport of Peptides by the Yeast α-Factor Pathway:

Experiments were performed to test: 1. the ability of Cadus 1239 to function as a vector for the expression of peptides encoded by synthetic oligonucleotides; 2. the suitability of the oligonucleotides, as designed, to direct the export of farnesylated, carboxymethylated peptides through the pathway normally used by a-factor; 3. the capacity of CY599 to export these peptides; and 4. the ability of CY599 to respond to those peptides that stimulate the pheromone response pathway by growing on selective media. These tests were performed using an oligonucleotide which encodes the 12 amino acid a-factor; specifically, the degenerate sequence $(NNN)_n$ in the oligo-nucleotide cloned into Cadus 1239 (see above) (with n=12) encodes the peptide component of a-factor pheromone. CY599 was transformed with the resulting plasmid (Cadus 1220), and transformants selected on uracil-deficient medium were transferred to histidine-deficient medium supplemented with a range of concentrations of aminotriazole. The results demonstrate that the synthetic oligonucleotide, expressed in the context of MFA1 by Cadus 1220, conferred upon CY599 enhanced aminotriazole-resistant growth on histidine-deficient media. In summation, these data indicate: 1. Cadus 1220 and the designed oligonucleotide are competent to direct the expression and export of a farnesylated, carboxymethylated peptide encoded by the $(NNN)_n$ sequence of the synthetic oligonucleotide; and 2. CY599 can, in an autocrine fashion, respond to a farnesylated, carboxymethylated peptide that stimulates its pheromone response pathway, in this case signaling initiates as a-factor binds to STE3.

Example 5

Proof of Concept

This example will demonstrate the utility of the autocrine system for the discovery of peptides which behave as functional pheromone analogues. By analogy, this system can be used to discover peptides that productively interact with any pheromone receptor surrogates.

CY588 (see strain 5, Example 2 above) will be transformed with CADUS 1215 containing oligonucleotides encoding random tridecapeptides for the isolation of functional α-factor analogues. CYS99 (see strain 6, Example 2 above) will be transformed with CADUS 1239 containing oligos of random sequence for the isolation of functional a-factor analogues. Colonies of either strain which can grow on histidine-deficient media following transformation will be expanded for the preparation of plasmid DNA, and the oligo-nucleotide cloned into the expression plasmid will be sequenced to determine the amino acid sequence of the peptide which presumably activates the pheromone receptor. This plasmid will then be transfected into an isogenic strain to confirm its ability to encode a peptide which activates the pheromone receptor. Successful completion of these experiments will demonstrate the potential of the system for the discovery of peptides which can activate membrane receptors coupled to the pheromone response pathway.

Random oligonucleotides to be expressed by the expression plasmid CADUS 1215 will encode tridecapeptides constructed as 5' CGTGAAG<u>CTTAAG</u>CGTGAGGCAGAAGCT$(NNK)_{13}$ <u>TGATCA</u>TCCG, where N is any nucleotide, K is either T or G at a ratio of 40:60 (see Proc. Natl. Acad. Sci.

87:6378, 1990; ibid 89:5393, 1992), and the AflII and BclI sites are underlined. This oligonucleotide is designed such that: the AflII and BclI sites permit inserting the oligos into the AflII and BglII site of CADUS 1215, the HindIII site just 5' to the AflII site in the 5' end of the oligo allows future flexibility with cloning of the oligos; the virtual repeat of GAGGCT and the GAGA repeats which are present in the wild-type sequence and which can form triple helices are changed without altering the encoded amino acids. The random oligonucleotides described above will actually be constructed from the following two oligos:

```
5' CGTGAAGCTTAAGCGTGAGGCAGAAGCT and

5' CGGATGATCA(MNN)₁₃AGCTTCTG,
``` where M is either A or C at a ratio of 40:60. The oligos will be annealed with one another and repetitively filled in, denatured, and reannealed (Kay et al, *Gene*, 1993). The double-stranded product will be cut with AflII and BclI and ligated into the AflII- and BglII-digested CADUS 1215. The BglII/BclI joint will create a TGA stop codon for termination of translation of the randomers. Because of the TA content of the Afl overhang, the oligos will be ligated to the AflII-and BglII-digested pADC-MFα at 4° C.

Random oligonucleotides to be expressed by the expression plasmid CADUS 1239 will encode monodecapeptides constructed as

```
5' GGTACTCGAGTGAAAAGAAGGACAAC(NNK)₁₁TGTGTTATTGCTTA
AGTACG,
``` where N is any nucleotide, K is either T or G at a ratio of 40:60 (see Proc. Natl. Acad. set 87:6378, 1990; ibid 89:5393, 1992). When cloned into the XhoI and AflII sites of CADUS 1239 the propeptides expressed under the control of the ADH1 promoter will contain the entire leader peptide of MFal, followed by 11 random amino acids, followed by triplets encoding CVIA (the C-terminal tetrapeptide of wild-type a-factor). Processing of the propeptide should result in the secretion of dodecapeptides which contain 11 random amino acids followed by a C-terminal, farnesylated, carboxymethylated cysteine.

Using the procedure described above, the oligonucleotides for expression in CADUS 1239 will actually be constructed from the following two oligos:

```
5' GGTACTCGAGTGAAAAGAAGGACAAC and

5' CGTACTTAAGCAATAACAca(MNN)₁₁GTTGTCC,
``` where M is either A or C at a ratio of 40:60, and the XhoI and AflII sites are underlined.

Discovery of α-Factor Analogues from a Random Peptide Library

An optimized version of strain 6 (Example 2 above) was derived. This yeast strain, CY2012 (MATa ste2-STE3far1Δ1442 mfal::LEU2 mfa2-lacZ fusl-HIS3 tbtl-1 ura3 leu2 his3 trpl suc2), was constructed as follows. From a cross of CY570 (MATa mfal::LEU2 mfa2-lacZ ura3 trpl his3Δ200 can1 leu2,fusl-HIS3 [MFA1 URA3 2 μ] [Fus1Δ8-73 TRP1 CEN6]) by CY1624 (MATα tbtl-1 fus1-HIS3 trpl ura3 leu2 his3 lys2-801 SUC+), a spore was selected (CY1877) of the following genotype: MATa mfa1::LEU2 mfa2-lacZ fus1-HIS3 tbtl-1 ura3 leu2 his3 trp1 suc2. This strain lacks both genes (NFA1 and MFA2) encoding a-factor precursors, contains the appropriate pheromone pathway reporter gene (fusl-HIS3), and transforms by electroporation at high efficiency (tbtl-1). This strain was altered by deletion of the FAR1 gene (with Cadus 1442; see Example 6), and replacement of STE2 coding sequences with that of STE3 (see Example 1) to yield CY2012.

This strain was transformed with plasmid DNA from a random a-factor library by electroporation and plated on 17 synthetic complete plates lacking uracil (-Ura), yielding approximately $10^5$ Ura+ colonies per plate after 2 days at 30° C. These colonies were replica plated to histidine-deficient synthetic complete media (-His) containing 0.2 mM 3-aminotriazole and after three days at 30° C. 35 His+ replicas were streaked to -Ura plates. The resultant colonies, 3 from each isolate, were retested for their His+ phenotype, and streaked to 5-fluoroorotic acid plates to obtain Ura segregants (lacking a library plasmid). Those Ura-segregants were tested for the loss of their His+ phenotype. Ten of the original isolates passed these tests; in two cases only one of the three Ura+ colonies purified from the isolate retained the His+ phenotype, but nevertheless subsequently segregated Ura His– colonies.

A single plasmid (corresponding to a bacterial colony) was obtained from each of the ten isolates, and reintroduced into CY2012. Eight of the ten plasmids passed the test of retaining the ability to confer the His+ phenotype on CY2012 (the two that failed correspond to the two isolates that were mentioned above, suggesting that these isolates contain at least one "irrelevant" plasmid). Sequencing of the randomized insert in the eight plasmids of interest revealed that four contain the sequence:

```
TAT GCT CTG TTT GTT CAT TTT TTT GAT ATT CCG

Tyr Ala Leu Phe Val His Phe Phe Asp Ile Pro
``` two contain the sequence:

```
TTT AAG GGT CAG GTG CGT TTT GTG GTT CTT GCT

Phe Lys Gly Gln Val Arg Phe Val Val Leu Ala,
``` and two contain the sequence:

```
CTT ATG TCT CCG TCT TTT TTT TTT TTG CCT GCG

Leu Met Ser Pro Ser Phe Phe Phe Leu Pro Ala
```

Clearly, these sequences encode novel peptides, as the native a-factor sequence differs considerably:

Tyr Ile Ile Lys Gly Val Phe Trp Asp Pro Ala.

The a-factor variants identified from random peptide libraries have utility as "improved" substrates of ABC transporters expressed in yeast. For example, identification of a preferred substrate of human MDR, one that retains agonist activity on the pheromone receptor, would permit the establishment of robust yeast screens to be used in the discovery of compounds that affect transporter function.

Example 6

Functional Expression of a Mammalian G Protein-coupled Receptor and Ligand in an Autocrine Yeast Strain This example details the following: (1) expression of human C5a receptor in yeast; (2) expression of the native ligand of this receptor, human C5a, in yeast; and (3) activation of the endogenous yeast pheromone pathway upon stimulation of the C5a receptor by C5a when both of these molecules are expressed within the same strain of autocrine yeast. Following the experimental data we outline the utility of autocrine strains of yeast that functionally express the human C5a receptor.

Human C5a is a 74 amino acid polypeptide that derives from the fifth component of complement during activation of the complement cascade; it is the most potent of the complement-derived anaphylatoxins. C5a is a powerful activator of neutrophils and macrophage functions including production of cytotoxic super oxide radicals and induction of chemotaxis and adhesiveness. In addition C5a stimulates smooth muscle contraction, induces degranulation of mast cells, induces serotonin release from platelets and increases vascular permeability. The C5a anaphylatoxin can also amplify the inflammatory response by stimulating the production of cytokines. As C5a is a highly potent inflammatory agent, it is a primary target for the development of antagonists to be used for intervention in a variety of inflammatory processes.

The C5a receptor is present on neutrophils, mast cells, macrophages and smooth muscle cells and couples through G proteins to transmit signals initiated through the binding of C5a.

Expression of the C5a Receptor

The plasmid pCDM8-C5aRc, bearing cDNA sequence encoding the human C5a receptor, was obtained from N. Gerard and C. Gerard (Harvard Medical School, Boston, Mass.) (Gerard and Gerard 1991). Sequence encoding C5a was derived from this plasmid by PCR using VENT polymerase (New England Biolabs Inc., Beverly Mass.), and the following primers:

1-GGTGGGAGGGTGCTCTCTAGAAGGAAGTGTTCACC

2-GCCCAGGAGACCAGACCATGGACTCCTTCAATTATACCACC

Primer #1 contains a single base-pair mismatch (underlined) to C5a receptor cDNA. It introduces an XbaI site (in bold) 201 bp downstream from the TAG termination codon of the C5a receptor coding sequence. Primer #2 contains two mismatched bases and serves to create an NcoI site (in bold) surrounding the ATG initiator codon (double underlined). The second amino acid is changed from an aspartic acid to an asparagine residue. This is the only change in primary amino acid sequence from the wild type human C5a receptor.

The PCR product was restricted with NcoI and XbaI (sites in bold) and cloned into CADUS 1002 (YEp51Nco), a Gal10 promoter expression vector. The sequence of the entire insert was determined by dideoxy sequencing using multiple primers. The sequence between the NcoI and XbaI sites was found to be identical to the human C5a receptor sequence that was deposited in GenBank (accession #JO5327) with the exception of those changes encoded by the PCR primers. The C5a receptor-encoding insert was transferred to CADUS 1289 (pLPXt), a PGK promoter expression vector, using the NcoI and XbaI sites, to generate the C5a receptor yeast expression clone, CADUS 1303.

A version of the C5a receptor which contains a yeast invertase signal sequence and a myc epitope tag at its amino terminus was expressed in Cadus 1270-transferred yeast under control of a GAL10 promoter. Plasmids encoding an untagged version of the C5a receptor and a myc-tagged derivative of FUS1 served as controls. The expression of the tagged receptor in yeast was confirmed by Western blot using the anti-myc monoclonal antibody 9E10. In the lane containing the extract from the Cadus 1270-transformant, the protein that is reactive with the anti-myc monoclonal antibody 9E10 was approximately 40 kD in size, as expected. Note that this receptor construct is not identical to the one used in the autocrine activation experiments. That receptor is not tagged, does not contain a signal sequence and is driven by the PGK promoter.

Expression of the Ligand, C5a

A synthetic construct of the sequence encoding C5a was obtained from C. Gerard (Harvard Medical School, Boston, Mass.). This synthetic gene had been designed as a FLAG-tagged molecule for the secretion from *E. coli* (Gerard and Gerard (1990) *Biochemistry* 29:9274–9281). The C5a coding region, still containing *E. coli* codon bias, was amplified using VENT polymerase (New England Biolabs Inc., Beverly Mass.) through 30 cycles using the following primers:

C5a5' = CCCCTTAAGCGTGAGGCAGAAGCTACTCTGCAAAAGAAGATC

C5a3' = GAAGATCTTCAGCGGCCGAGTTGCATGTC

A PCR product of 257 bp was gel isolated, restricted with AflII and BglII, and cloned into CADUS 1215 (an expression vector designed to express peptide sequences in the context of Mfa) to yield CADUS 1297. The regions of homology to the synthetic C5a gene are underlined. The 5' primer also contains pre-pro α-factor sequence. Upon translation and processing of the pre-pro a-factor sequence, authentic human C5a should be secreted by yeast containing CADUS 1297. The insert sequence in CADUS 1297 was sequenced in both orientations by the dideoxy method and found to be identical to that predicted by the PCR primers and the published sequence of the synthetic C5a gene (Franke et al. (1988) *Methods in Enzymology* 162: 653–668).

Two sets of experiments, aside from the autocrine activation of yeast detailed below, demonstrated that CADUS 1297 can be used to express C5a in yeast.

1). C5a was immunologically detected in both culture supernatant and lysed cells using a commercially available enzyme-linked immunosorbent assay (ELISA)(Table 1). This assay indicated the concentration of C5a in the culture supernatant to be approximately 50 to 100 nM. In comparison, in data derived from mammalian cells, the binding constant of C5a to its receptor is 1 nM (Boulay et al.(1991) Biochemistry 30:2993–2999.

2). C5a expressed in yeast was shown to compete for binding with commercially obtained (Amersham Corporation, Arlington Heights, Ill.), radiolabeled C5a on induced HL60 cells.

Activation of the Pheromone Response Pathway in Autocrine Yeast Expressing the Human C5a Receptor and Human C5a Activation of the yeast pheromone response pathway through the interaction of C5a with the C5a receptor was demonstrated using a growth read-out. The strain used for this analysis, CY455 (MATα tbt1-1 ura3 leu2 trp1 his3 fus1-HIS3 can1 ste14::TRP1 ste3*1156) contains the following significant modifications. A pheromone inducible HIS3 gene, fus1-HIS3, is integrated at the Fus1 locus. A hybrid gene containing sequence encoding the first 41 amino acids of GPA1 (the yeast Gα subunit) fused to sequence encoding human Gαi2a (minus codons for the N-terminal 33 amino acids) replaces GPA1 at its normal chromosomal location. The yeast STE14 gene is disrupted to lower the basal level of signaling through the pheromone response pathway. The yeast a-factor receptor gene, STE3, is deleted. The last two modifications are probably not essential, but appear to improve the signal-to-noise ratio.

CY455 (MATα tbt1-1 ura3 leu2 trp1 his3 fus1-HIS3 can1 ste14::TRP1 ste3*1156) was transformed with the following plasmids:

Cadus 1289+Cadus 1215=Receptor⁻ Ligand⁻=(R–L–)
Cadus 1303+Cadus 1215=Receptor⁺ Ligand⁻=R+L–
Cadus 1289+Cadus 1297=Receptor⁻ Ligand⁺=(R–L+)
Cadus 1303+Cadus 1297=Receptor⁺ Ligand⁺=(R+L+)
Receptor refers to the human C5a receptor.
Ligand refers to human C5a.

Three colonies were picked from each transformation and grown overnight in media lacking leucine and uracil, at pH 6.8 with 25 mM PIPES (LEU URA pH6.8 with 25 mM PIPES). This media was made by adding 0.45 ml of sterile 1M KOH and 2.5 ml of sterile 1M PIPES pH 6.8 to 100 ml of standard SD LEU– URA– media. After overnight growth the pH of this media is usually acidified to approximately pH 5.5. Overnight cultures were washed once with 25 mM PIPES pH 6.8 and resuspended in an equal volume of media lacking leucine, uracil and histidine (LEU URA HIS pH 6.8 with 25 mM PIPES). The optical density at 600 nm of a 1/20 dilution of these cultures was determined and the cultures were diluted into 25 mM PIPES pH 6.8 to a final $OD_{600}$ of 0.2. A volume (5 ul) of this dilution equivalent to 10,000 cells was spotted onto selective (HIS+ TRP– pH6.8) plates. Only those strains expressing both C5a and its receptor (R+L+) show growth on the selective plates which lack histidine. All test strains are capable of growth on plates containing histidine. The R+L+ strain will grow on plates containing up to 5 mM aminotriazole, the highest concentration tested.

Figure 4:
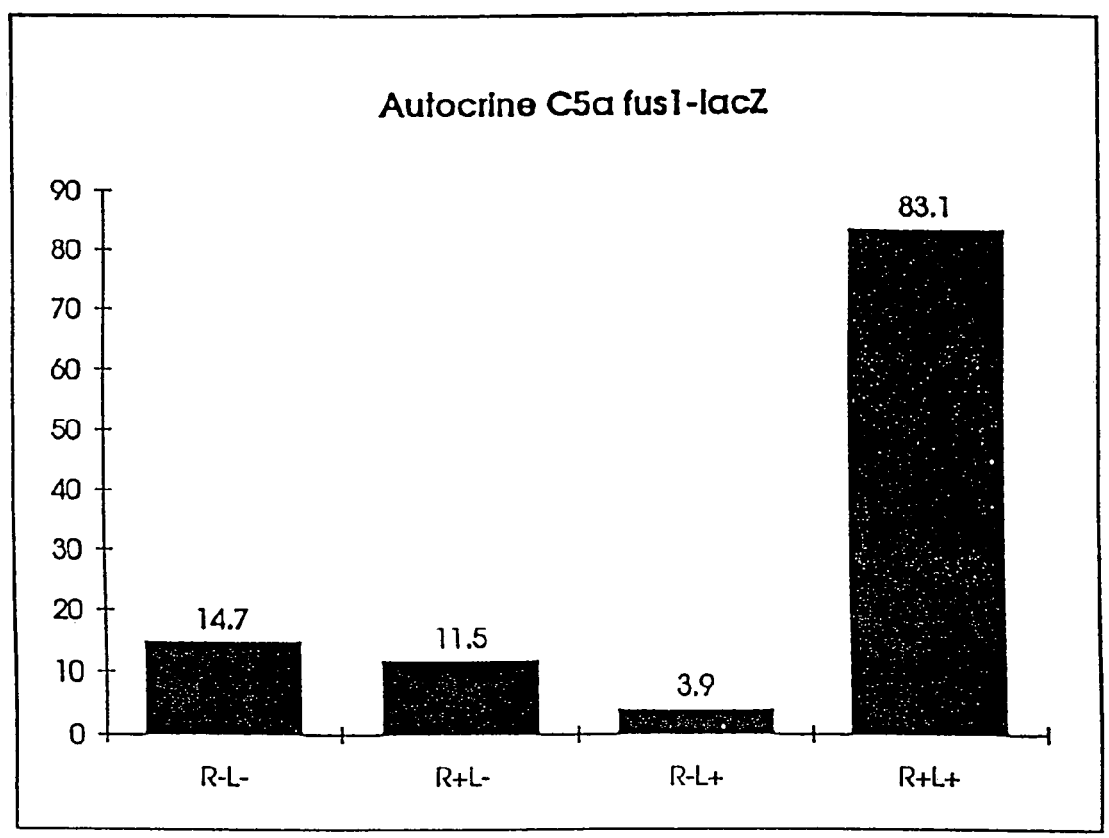
FIG. 4. Activity of a fus1 promoter in response to signaling by human C5a expressed in autocrine strains of yeast.

For verification of pheromone pathway activation and quantification of the stimulation, the activity of the fus1 promoter was determined colorometrically using a fus1-lacZ fusion in a similar set of strains. CY878 (MATα tbt1-1 fus1-HIS3 caN1 ste14::trp1::LYS2 ste3*1156 gpal(41)-Gαi2) was used as the starting strain for these experiments. This strain is a trp1 derivative of CY455. The transformants for this experiment contained CADUS 1584 (pRS424-fus1-lacZ) in addition to the receptor and ligand plasmids. Four strains were grown overnight in SD LEU URA TRP pH6.8 with 50 mM PIPES to an $OD_{600}$ of less than 0.8. Assay of β-galactosidase activity (Guarente 1983) in these strains yields the data shown in FIG. 4. The coupling of the C5a receptor to Gα chimeras is shown in Table 2.

Uses of the Autocrine C5a Strains:

A primary use of the autocrine C5a strains will be in the discovery of C5a antagonists. Inhibitors of the biological function of C5a would be expected to protect against tissue damage resulting from inflammation in a wide variety of inflammatory disease processes including but not limited to: respiratory distress syndrome (Duchateau et al. (1984) Am Rev Respir Dis 130:1058); (Hammerschmidt et al. (1980) Lancet 1:947), septic lung injury (Olson et al. 1985) Ann Surg 202:771), arthritis (Banerjee et al. (1989) J. Immuinol 142:2237), ischemic and post-ischemic myocardial injury (Weisman (1990) Science 146:249); (Crawford et al. (1988) Circulation 78:1449) and burn injury (Gelfand et al. (1982) J. Clin Invest 70:1170).

The autocrine C5a system as described can be used to isolate C5a antagonists as follows:

1. High throughput Screens to Identify Agonists of the C5a Receptor.

Figure 5:
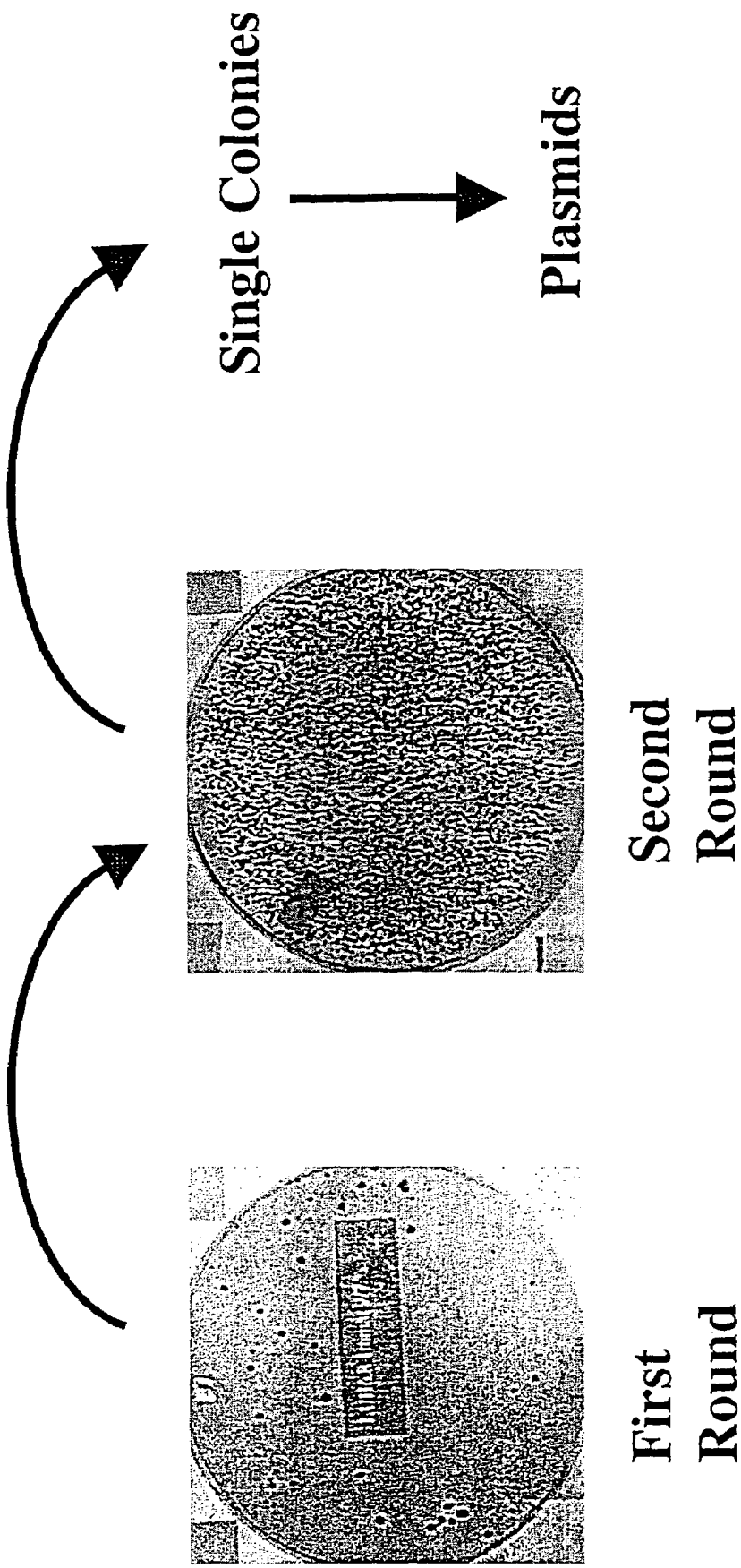
FIG. 5. Exemplary set of steps for isolating surrogate ligands for the C5a receptor.

FIG. 5 illustrates an exemplary set of steps for isolating surrogate ligands for the C5a receptor by the subject autocrine SSCL™ method. As described above, yeast cells were engineered to express human C5a receptor under conditions whereby the receptor is functionally coupled to a fus1:his3 reporter gene construct. The cells are transformed with a library encoding random peptides (supra) and plated on selective (His⁻) media. In the first round of screening (see FIG. 5) yeast colonies are isolated by their ability to grow on the histidine deficient plates. In order to distinguish growth due to real receptor agonists, as opposed to revertants of the histidine auxotroph, DNA was extracted from the colonies isolated in the first round, amplified in E coli, and transformed back into the engineered yeast cells and plated on His⁻ plates. High frequency of transformation or "jackpots" of cell growth in the the second round indicates plasmids encoding genuine receptor agonists; individual colonies were picked, plasmid DNA isolated, amplified in E. coli, and the sequence of the surrogate ligand deduced from the DNA sequence corresponding peptide-encoding region of each isolated plasmid.

Figure 6:
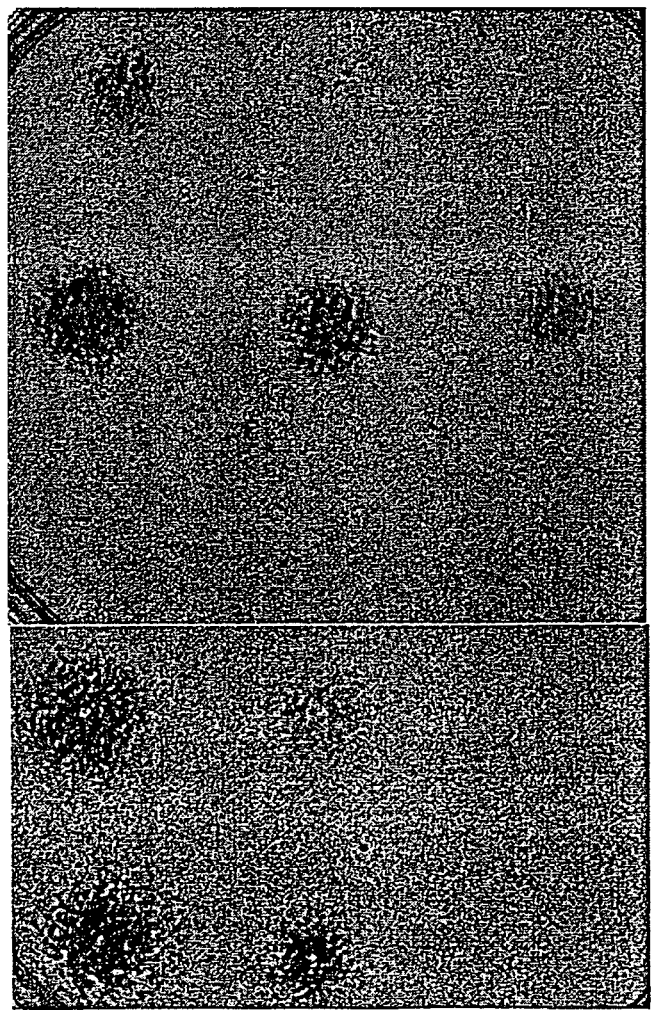
FIG. 6. Spotting a lawn of recombinant yeast cells with various C5a receptor agonists or DMF solvent control.

After sequencing and deducing the amino acid sequence of the encoded surrogate ligands identified in the histidine auxotrophy rescue assay described above, individual peptides were chemically synthesized, dissolved in DMF, and spotted on a lawn of the engineered yeast cells. As illustrated in FIG. 6, C5a receptor agonists result in growth of cells around the areas were a peptide was spotted. FIG. 7 shows the amino acid sequence for C5a surrogate agonist peptides obtained by the above method. Interestingly, the isolates do not show extensive sequence homology to one and other, though several duplicate isolates were found amongst different transfornants.

Figure 8:
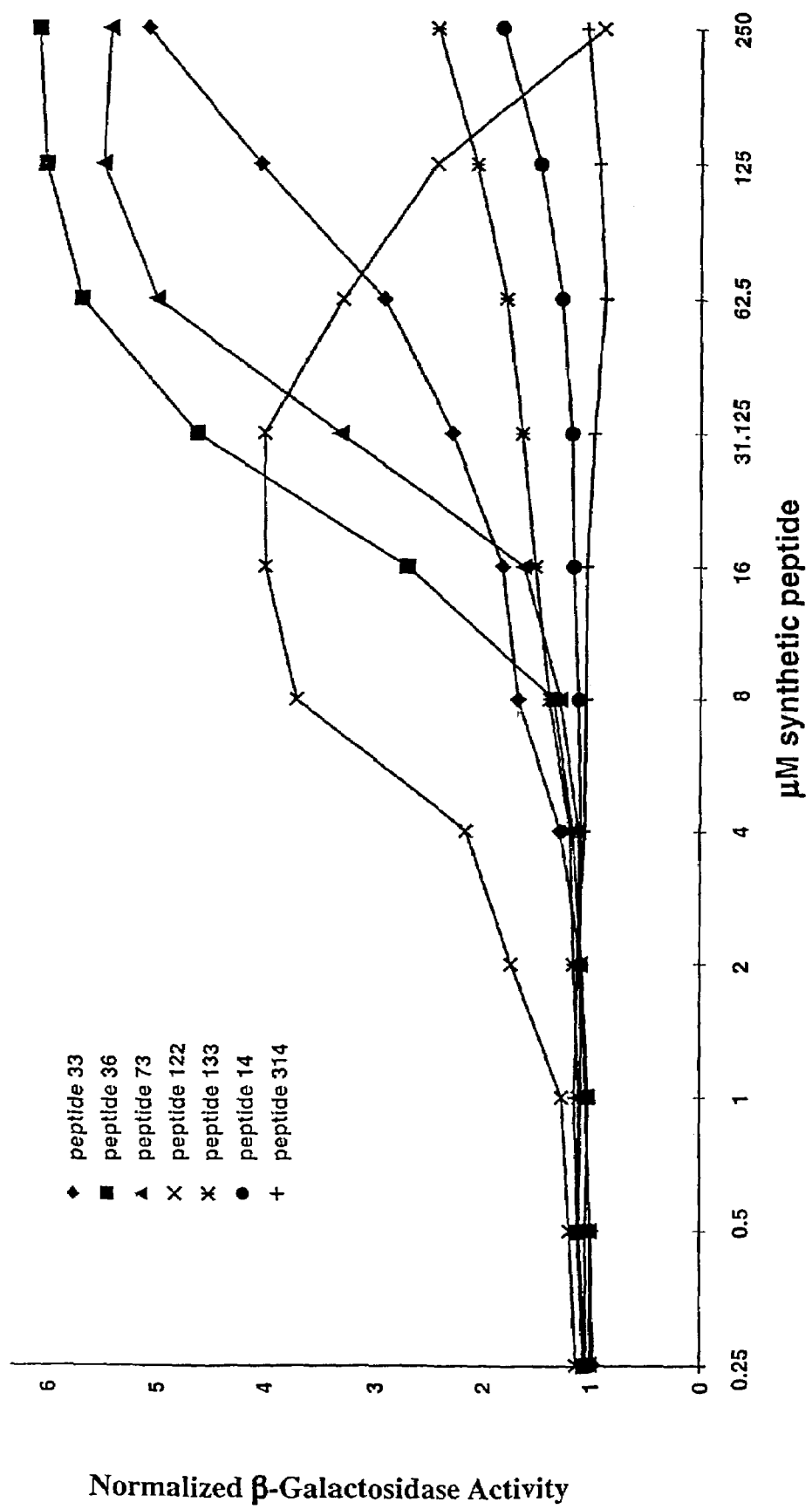
FIG. 8. Dose response curve for various C5a receptor surrogate peptide ligands based on a colorimetric lacZ readout.

Using the fus1:lacZ reporter gene construct described above, yeast cells engineered to express the human C5a receptor were stimulated with synthetic C5a surrogate peptides at varying concentrations. FIG. 8 shows the dose response curve for various of the surrogate peptide ligands using on a colorimetric lacZ readout.

Figure 9:
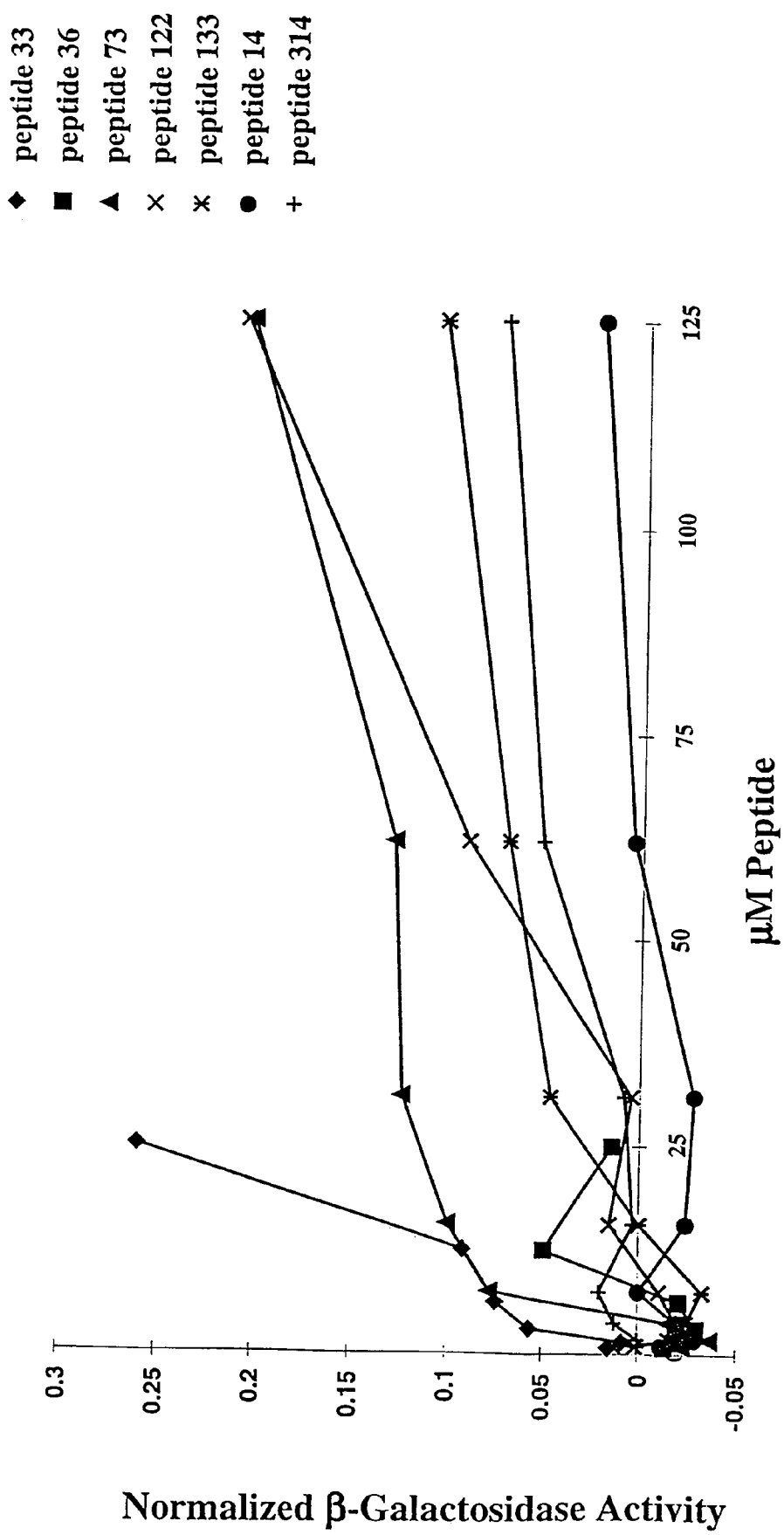
FIG. 9. Expression of a lacZ reporter gene construct, engineered into the mammalian HEK293 cell-line, in response to stimulation of a C5a receptor by a C5a receptor agonist.

The activity of the surrogate ligands were subsequently tested, as shown in FIG. 9, by contacting the mammalian cell-line HEK293, which has been further engineered to provide a C5a receptor coupled with a CRE:lacZ reporter gene construct, with chemically synthesized versions of the peptides identified as C5a ligands by the autocrine method described above.

To further improve the selectivity and/or potency of the agonists identified by the above steps, we selected a surrogate peptide (peptide 122, see FIG. 7), and created degenerate peptide libraries based on the sequence of that peptide as a starting point (e.g., a semi-random library) as follows:

```
C5a pep122
Tyr-Thr-Arg-Gly-Trp-Lys-Ala-Arg-Leu-Leu-
```

```
                    -continued
Trp-Leu-Ile sub-libraries
N-term
Xaa-Xaa-Xaa-Xaa-Trp-Lys-Ala-Arg-Leu-Leu- Trp-Leu-Ile mid4
Tyr-Thr-Arg-Gly-Xaa-Xaa-Xaa-Xaa-Leu-Leu- Trp-Leu-Ile C-term
Tyr-Thr-Arg-Gly-Trp-Lys-Ala-Arg-Xaa-Xaa- Xaa-Xaa-Xaa mod1
Xaa-Thr-Arg-Xaa-Trp-Lys-Xaa-Arg-Leu-Xaa- Trp-Leu-Xaa mod2
Tyr-Xaa-Arg-Gly-Xaa-Lys-Ala-Xaa-Leu-Leu- Xaa-Leu-Ile mod3
Tyr-Thr-Xaa-Gly-Trp-Xaa-Ala-Arg-Xaa-Leu- Trp-Xaa-Ile
```

Following the protocols set out above for the first generation peptide library, the second generation peptide library was screened, and individual clones isolated based on their ability to stimulate C5a receptor dependent transcription.

Figure 10:
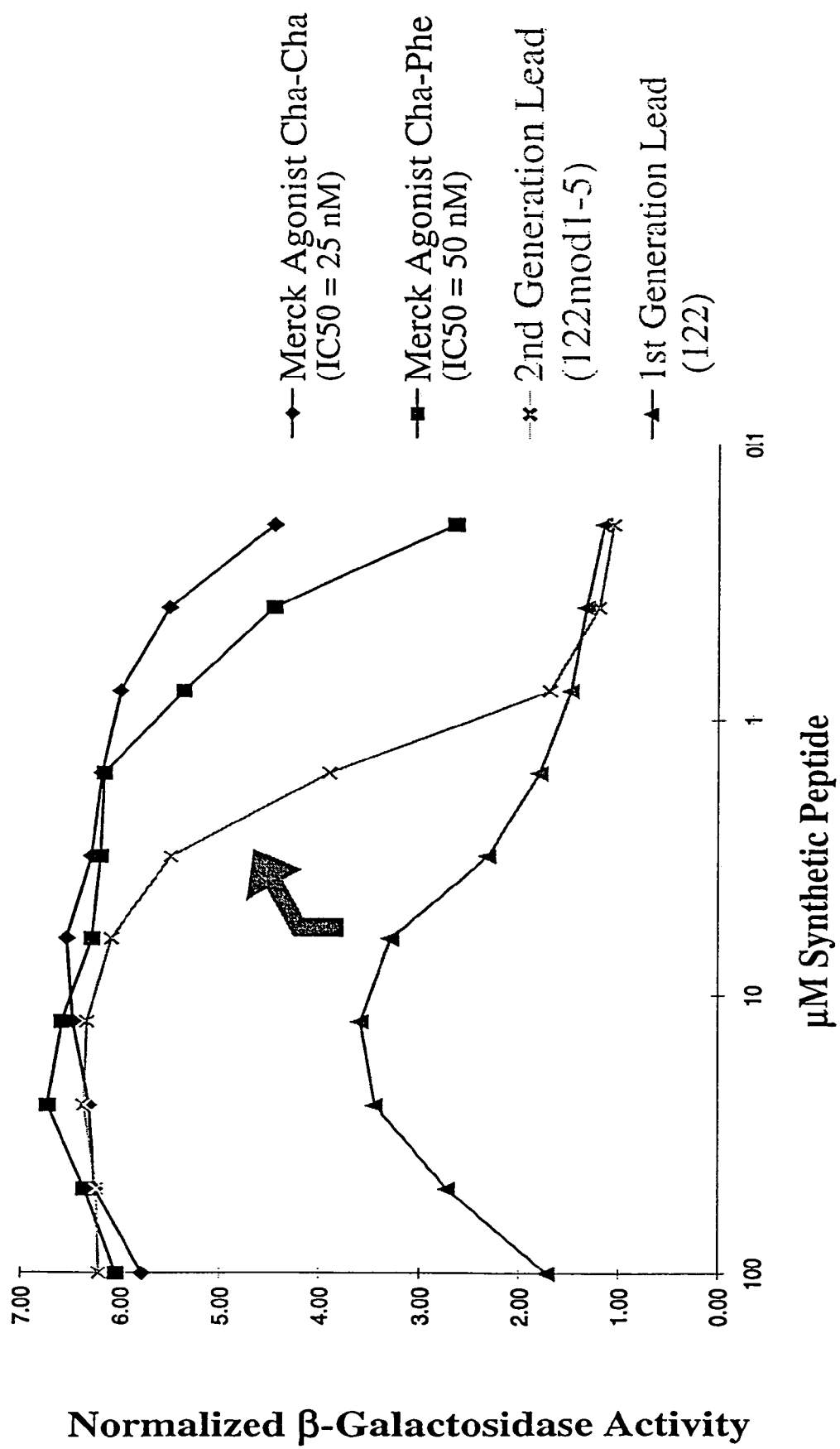
FIG. 10. Dose-response curves comparing a second generation C5a receptor agonist (122mod1-5) with other known C5a receptor agonists.

The amino acid sequence for an isolate from the second generation peptide library, designated herein 122mod1-5, was deduced to be Asp-Thr-Arg-Ser-Trp-Lys-Leu-Arg-Leu-Leu-Trp-Leu-Ala. As illustrated by FIG. 10, the 122mod1-5 peptide was chemically synthesized and contacted with a yeast cell engineered with a human C5a receptor and fus1: lacZ reporter gene construct. The activity of the peptide (122mod1-5), determrined by its ability to stimulate expression of the lacZ gene, was compared with the original peptide (122) used to generate the second generation peptide library and two other C5a receptor agonists. See Koneatis et al. (1994) *J mmunol* 153:4200.

2. Identification of Antagonists of C5a.

In another embodiment, replacement of the fus1-HIS3 read-out with one of several negative selection schemes (fus1-URA3/FOA, fus1-GAL1/galactose or deoxygalactose, Far1 sst2 or other mutations that render yeast supersensitive for growth arrest) would generate a test system in which the presence of an antagonist would result in the growth of the assay strain. Such an approach would be applicable to high-throughput screening of compounds as well as to the selection of antagonists from random peptide libraries expressed in autocrine yeast. Optimization of screens of this type would involve screening the R+L+ strain at a concentration of aminotriazole which ablates growth of the R+L– strain (we are currently using 0.6 to 0.8 mM) and counter-screening the R+L– strain at a concentration of aminotriazole which gives an identical growth rate (we are using 0.14 mM). In addition, the system could employ one of several colorometric, fluorescent or chemiluminescent readouts. Some of the genes which can be fused to the fus1 promoter for these alternate read-outs include lacZ (colorometric and fluorescent substrates), glucutonidase 20 (colorometric and fluorescent substrates), phosphatases (e.g. PHO3, PHO5, alkaline phosphatase; colorometric and chemiuminescent substrates), green protein (endogenous fluorescence), horse radish peroxidase (colorometric), luciferase (chemiluminescence).

The autocrine C5a strains have further utility as follows:

3. In the Identification of Novel C5a Agonists from Random Peptide Libraries Expressed in Autocrinie Yeast.

Novel peptide agonists would contribute to structure/function analyses used to guide the rational design of C5a antagonists.

4. In the Identification of Receptor Mutants.

Constitutively active, that is, ligand independent, receptors may be selected from highly mutagenized populations by growth on selective media. These constitutively active receptors may have utility in permitting the mapping of the sites of interaction between the receptor and the G-protein. Identification of those sites may be important to the rational design of drugs to block that interaction. In addition, receptors could be selected for an ability to be stimulated by some agonists but not others or to be resistant to antagonist. These variant receptors would aid in mapping sites of interaction between receptor and agonist or antagonist and would therefore contribute to rational drug design efforts.

5. In the Identification of Molecules that Interact with Gαi2.

Compounds or peptides which directly inhibit GDP exchange from Gαi2 would have the same effect as C5a antagonists in these assays. Additional information would distinguish inhibitors of GDP exchange from C5a antagonists. This information could be obtained through assays that determine the following:

1. inhibition by test compounds of Gαi2 activation from other receptors, 2. failure of test compounds to compete with radiolabeled C5a for binding to the C5a receptor, 3. failure of test compounds to inhibit the activation of other Gα subunits by C5a, and 4. inhibition by test compounds of signalling from constitutively active versions of C5a, or other, receptors.

Example 7

Construction of Xybrid Gα Genes Construction of Two Sets of Chimeric Yeast/Mammalian Gα Genes, GPA$_{41}$-Gα and GPA1$_{Bam}$-Gα

The Gα subunit of heterotrimeric G proteins must interact with both the βγ complex and the receptor. Since the domains of Gα required for each of these interactions have not been completely defined and since our final goal requires Gα proteins that communicate with a mammalian receptor on one hand and the yeast βγ subunits on the other, we desired to derive human-yeast chimeric Gα proteins with an optimized ability to perform both functions. From the studies reported here we determined that inclusion of only a small portion of the amino terminus of yeast Gα is required to couple a mammalian Gα protein to the yeast βγ subunits. It was anticipated that a further benefit to using these limited chimeras was the preservation of the entire mammalian domain of the Gα protein believed to be involved in receptor contact and interaction. Thus the likelihood that these chimeras would retain their ability to interact functionally with a mammalian receptor expressed in the same yeast cell was expected to be quite high.

Plasmid Constructions.

pRS416-GPA1 (Cadus 1069). An XbaI-SacI fragment encoding the entire GPA1 promotor region, coding region and approximately 250 nucleotides of 3' untranslated region was excised from 10 YCplac111-GPA1 (from S. Reed, Scripps Institute) and cloned into YEp vector pRS416 (Sikorski and Hieter, Genetics 122: 19 (1989)) cut with XbaI and SacI.

Site-directed mutagenesis of GPA1 (Cadus 1075, 1121 and 1122). A 1.9 kb EcoRI fragment containing the entire GPA1 coding region and 200 nucleotides from the 5' untranslated region was cloned into EcoRI cut, phosphatase-treated pALTER-1 (Promega) and transformed by electroporation (Biorad Gene Pulser) into DH5αF' bacteria to yield Cadus 1075. Recombinant phagemids were rescued with M13KO7 helper phage and single stranded recombinant DNA was extracted and purified according to the manufacturer's specifications. A new NcoI site was introduced at the initiator methionine of GPA1 by oligonucleotide directed mutagenesis using the synthetic oligonucleotide:

5' GATATATTAAGGTAGGAAACCATGGGGTGTACAGTGAG 3'.

Positive clones were selected in ampicillin and several independent clones were sequenced in both directions across the new NcoI site at +1. Two clones containing the correct sequences were retained as Cadus 1121 and 1122.

Construction of a GPA1-based expression vector (Cadus 1127). The vector used for expression of full length and hybrid mammalian Gα proteins in yeast, Cadus 1127, was constructed in the following manner. A 350 nucleotide fragment spanning the 3' untranslated region of GPA1 was amplified with Taq polymerase (AmpliTaq; Perkin Elmer) using the oligonucleotide primers A (5' CGAGGCTC-GAGGGAACGTATAATTAAAGTAGTG 3') and B (5' GCGCGGTACCAAGCTTCAATTCGAGATAATACCC 3'). The 350 nucleotide product was purified by gel electrophoresis using GeneClean II (Bio101) and was cloned directly into the pCRII vector by single nucleotide overlap TA cloning (InVitrogen). Recombinant clones were characterized by restriction enzyme mapping and by dideoxynucleotide sequencing. Recombinant clones contained a novel XhoI site 5' to the authentic GPA1 sequence and a novel KpnI site 3' to the authentic GPA1 sequence donated respectively by primer A and primer B.

The NotI and SacI sites in the polylinker of Cadus 1013 (pRS414) were removed by restriction with these enzymes followed by filling in with the Klenow fragment of DNA polymerase I and blunt end ligation to yield Cadus 1092. The 1.4 kb PstI-EcoRI 5' fragment of GPA1 from YCplac111-GPA1 containing the GPA1 promoter and 5' untranslated region of GPA1 was purified by gel electrophoresis using GeneClean (BiolO1) and cloned into PstI-EcoRI restricted Cadus 1013 to yield Cadus 1087. The PCR amplified XhoI-KpnI fragment encoding the 3' untranslated region of GPA1 was excised from Cadus 1089 and cloned into XhoI-KpnI restricted Cadus 1087 to yield Cadus 1092. The NotI and SacI sites in the polylinker of Cadus 1092 were removed by restriction with these enzymes, filling in with the Klenow fragment of DNA polymerase I, and blunt end ligation to yield Cadus 1110. The region of Cadus 1122 encoding the region of GPA1 from the EcoRI site at −200 to +120 was amplified with Vent DNA polymerase (New England Biolabs, Beverly, Mass.) with the primers 5' CCCGAATCCACCAATTTCTTTACG 3' and

5' GCGGCGTCGACGCGGCCGCGTAACAGT 3'.

The amplified product, bearing an EcoRI site at its 5' end and novel SacI, NotI and SalI sites at its 3' end was restricted with EcoRI and SalI, gel purified using GeneClean II (BiolO1), and cloned into EcoRI and SalI restricted Cadus 1110 to yield Cadus 1127. The DNA sequence of the vector between the EcoRI site at −200 and the KpnI site at the 3' end of the 3' untranslated region was verified by restriction enzyme mapping and dideoxynucleotide DNA sequence analysis.

PCR amplification of $GPA_{41}$-Gα proteins and cloning into Cadus 1127. cDNA clones encoding the human G alpha subunits Gαs, Gαi2, Gαi3, and S. cerevisiae GPA1 were amplified with Vent thermostable polymerase (New England Bioloabs, Beverly, Mass.). The primer pairs used in the amplification are as follows:

Gαs
Primer 1:
5'CTGCTGGAGCTCCGCCTGCTGCTGCTGGGTGCTGGAG3'

(SacI 5')

Primer 2 :
5'CTGCTGGTCGACGCGGCCGCGGGGGTTCCTTCTTAGAAGCAGC3'

(SalI 3')

Primer 3:
5'GGGCTCGAGCCTTCTTAGAGCAGCTCGTAC3' (XhoI 3')

Gαi2
Primer 1:
5'CTGCTGGAGCTCAAGTTGCTGCTGTTGGGTGCTGGGG3' (SacI5')

Primer 2:
5'CTGCTGGTCGACGCGGCCGCGCCCCTCAGAAGAGGCCGCGGTCC3'

(SalI 3')

Primer 3:
5'GGGCTCGAGCCTCAGAAGAGGCCGCAGTC3' (XhoI 3')

Gαi3
Primer 1:
5'CTGCTGGAGCTCAAGCTGCTGCTACTCGGTGCTGGAG3' (SacI5')

Primer 2:
5'CTGCTGGTCGACGCGGCCGCCACTAACATCCATGCTTCTCAATAAAGT

C3' (SalI 3')

Primer 3:
5'GGGCTCGAGCATGCTTCTCAATAAAGTCCAC3' (XhoI 3')

After amplification, products were purified by gel electrophoresis using GeneClean II (Bio101) and were cleaved with the appropriate restriction enzymes for cloning into Cadus 1127.

The hybrid $GPA_{41}$-G$_α$ subunits were cloned via a SacI site introduced at the desired position near the 5' end of the amplified genes and a SalI or XhoI site introduced in the 3' untranslated region. Ligation mixtures were electroporated into competent bacteria and plasmid DNA was prepared from 50 cultures of ampicillin resistant bacteria.

Construction of Integrating Vectors Encoding $GPA_{41}$-G$_α$ Subunits. The coding region of each $GPA_{41}$-G$_α$ hybrid was cloned into an integrating vector (pRS406=URA3 AmpR) using the BssHII sites flanking the polylinker cloning sites in this plasmid. Cadus 1011 (pRS406) was restricted with BssHII, treated with shrimp alkaline phosphatase as per the manufacturer's specifications, and the linearized vector was purified by gel electrophoresis. Inserts from each of the $GPA_{41}$-$G_\alpha$ hybrids were excised with BssHII from the parental plasmid, and subcloned into gel purified Cadus 1011.

Construction of $GPA_{BAM}$-$G\alpha$ Constructs. A novel BamHI site was introduced in frame into the GPA1 coding region by PCR amplification using Cadus 1179 (encoding a wildtype GPA1 allele with a novel NcoI site at the initiator methionine) as the template, VENT polymerase, and the following primers: Primer A=5' GCATCCATCAATAATCCAG 3' and Primer B=5' GAAACAATGGATCCACTTCTTAC 3'. The 1.1 kb PCR product was gel purified with GeneClean II (Bio101), restricted with NcoI and BamHI and cloned into NcoI-BamHI cut and phosphatased Cadus 1122 to yield Cadus 1605. The sequence of Cadus 1605 was verified by restriction analysis and dideoxy-sequencing of double-stranded templates. Recombinant $GPA_{Bam}$-$G\alpha$ hybrids of $G\alpha s$, $G\alpha i2$, and $G\alpha 16$ were generated. Construction of Cadus 1855 encoding recombinant $GPA_{Bam}$-$G\alpha$ 16 serves as a master example: construction of the other hybrids followed an analogous cloning strategy. The parental plasmid Cadus 1617, encoding native $G\alpha 16$, was restricted with NcoI and BamHI, treated with shrimp alkaline phosphatase as per the manufacturer's specifications and the linearized vector was purified by gel electrophoresis. Cadus 1605 was restricted with NcoI and BamHI and the 1.1 kb fragment encoding the amino terminal 60% of GPA1 with a novel BamHI site at the 3' end was cloned into the NcoI- and BamHI-restricted Cadus 1617. The resulting plasmid encoding the $GPA_{Bam}$-$G\alpha$ 16 hybrid was verified by restriction analysis and assayed in tester strains ror an ability to couple to yeast $G\beta\gamma$ and thereby suppress the gpa1 null phenotype. Two additional $GPA_{Bam}$-$G\alpha$ hybrids, $GPA_{Bam}$-$G\alpha s$ and $GPA_{Bam}$-$G\alpha i2$, described in this application were prepared in an analogous manner using Cadus1606 as the parental plasmid for the construction of the $GPA_{Bam}$-$G\alpha$ i2 hybrid and Cadus 1181 as the parental plasmid for the construction of the $GPA_{Bam}$-$G\alpha$ s hybrid.

Coupling by chimeric $G\alpha$ proteins. The $G\alpha$ chimeras described above were tested for the ability to couple a mammalian G protein-coupled receptor to the pheromone response pathway in yeast. The results of these experiments are outlined in Table 3. Results obtained using $GPA1_{41}$-$G\alpha i2$ to couple the human C5a receptor to the pheromone response pathway in autocrine strains of yeast are disclosed in above.

Example 8

Screening for Modulators of G-alpha Activity

Screens for modulators of $G\alpha$ activity may also be performed as shown in the following examples for illustration purposes, which are intended to be non-limiting.

Strains CY4874 and CY4877 are isogenic but for the presence of Q205L mutation in the cloned $G\alpha_{i2}$ gene cloned into plasmid 1. Strains CY4901 and CY4904 each have a chromosomally integrated chimeric $G\alpha$ fusion comprising 41 amino acids of gpa1 at the N terminus of the human $G\alpha_{i2}$ gene and are isogenic but for the presence of a constitutively activating mutation in the C5a receptor gene of CY4901. Strain CY5058 is a gpa1 mutant which carries only the yeast $G\beta\gamma$ subunits and no $G\alpha$ subunit. This strain is a control strain to demonstrate specificity of action on the $G\alpha$ subunit.

I. Suppression of Activation by Mutation of $G\alpha$

The Q205L mutation is a constitutively activated GTPase deficient mutant of the huma$\alpha_{i2}$ gene. Antagonist compounds, chemicals or other substances which act on $G\alpha_{i2}$ can be recognized by their action to reduce the level of activation and thus reduce the signal from the fus1-lacZ reporter gene on the second plasmid (Plasmid 2).

A. GTPase $G\alpha i2$ Mutants
    test component=gpa$_{41}$-$G\alpha_{i2}$ ($Q_{205}L$)
    control component=gpa$_{41}$-$G\alpha_{i2}$ As well as the CY4874 and CY4877 constructs detailed above, similar strains with fus1-His3 or fus2-CAN-1 growth readouts may also be used. The fus1-His3 strains are preferred for screening for agonists and the fus2-CAN1 strains are preferred for antagonist screens.

| Readout | test strain | effect of $G\alpha_{i2}$ antagonist | control strain |
|---|---|---|---|
| fus1-HIS3 | CY4868 | inhibit growth of -HIS +AT (Aminotriazole) | CY4871 |
| fus1-lacZ | CY4874 | reduce β-gal activity | CY4877 |
| fus2-CAN1 | CY4892 | induce growth on canavanine | CY4386 |

In each case an antagonist should cause the test strain to behave more like the control strain.

B. GTPase $G\alpha_s$ Mutants ($G\alpha$ Specificity)
    test component=$G\alpha S(Q_{227}L)$
    control component=$G\alpha_s$

| Readout | test strain | effect of $G\alpha_{i2}$ antagonist | control strain |
|---|---|---|---|
| fus1-HIS3 | CY4880 | none | CY4883 |
| fus1-lacZ | CY4886 | none | CY4889 |
| fus2-CAN1 | CY4895 | none | CY4898 |

In each case a non-specific antagonist would cause the test strain to behave more like the control strain.

Additional media requirements: -TRP for $G\alpha$ plasmid maintenance in fus1-HIS3 and fus2-CAN1 screens and -TRP -URA for $G\alpha$ and fus1-lacZ plasmid maintenance in fus1-lacZ screen.

II. Suppression of Activation by Receptors

Constitutively Activated C5a Receptors
    test component=C5aR*($P_{184}L$, activated C5a Receptor)
    control component=C5aR The C5aR* mutation has a Leucine residue in place of the Proline residue of the wild-type at position 184 of the amino acid sequence.

| Readout | test strain | effect of $G\alpha_{i2}$ antagonist | control strain |
|---|---|---|---|
| fus1-HIS3 | CY4029 | inhibit growth of -HIS +AT (Aminotriazole) | CY2246 |
| fus1-lacZ | CY4901 | reduce β-gal activity | CY4904 |
| fus2-CAN1 | CY4365 | induce growth on canavanine | CY4362 |

In each case an antagonist should cause the test strain to behave more like the control strain.

Additional media requirements: -LEU for receptor plasmid maintenance in fus1-HIS3 and fus2-CAN1 screens and -LEU-URA for receptor and fus1-lacZ plasmid maintenance in fus1-lacZ screen, non-buffered yeast media (pH 5.5).

Example 9

Identification of a Surrogate Ligand using Expression of a Random Peptide Library in Yeast Expressing an Orphan Mammalian Receptor FPRL-1 (formyl peptide receptor-like 1) is a structural homolog of the formyl peptide receptor (FPR). FPR is a G protein-coupled receptor, expressed on neutrophils and phagocytic cells, that is stimulated by N-formyl peptides of bacterial origin. Specific binding of the natural ligand, f-Met-Leu-Phe, stimulates transduction of a signal to mobilize calcium, resulting in cellular changes including chemotaxis and the release of granule contents. Low stringency hybridization of HL60 cDNA libraries with an FPR cDNA probe permitted the identification of the related receptor, FPRL-1 (Murphy et al. supra; Ye et al. supra). The FPRL-1 cDNA encodes a 351 amino acid protein with 69% sequence homology to FPR (Murphy et al. supra) FPR and FPRL-1 were found to co-localize to human chromosome 19 and to have a tissue expression pattern identical to that of FPR, i.e., expression is restricted to cells of myeloid origin (Murphy et al. supra). Ye et al. (supra) demonstrated weak binding of f-Met-Leu-Phe (uM concentrations) to fibroblasts transfected with FPRL-1 cDNA. In contrast, Murphy et al. (supra) could not detect binding of N-formyl peptides to Xenopus oocytes transfected with FPRL-1 cDNA. FPRL-1 appears to be an orphan receptor whose specific ligand differs from the formyl peptide ligands to which FPR responds.

In this example experiments detailing the following will be described: (1) establishment of a strain of yeast designed to express the human orphan G protein-coupled receptor FPRL-1; (2) expression of a random peptide library in the aforementioned strain of yeast; and (3) activation of the endogenous yeast pheromone pathway upon stimulation of the FPRL-1 receptor by a peptide encoded by a random library expressed within the same strain of yeast.

Preparation of FPRL-1 Yeast Expression Vector

A plasmid, pFPRL1-L31, containing a 2.6 kb EcoRI-Xho1 fragment encoding the FPRL-1 cDNA in the BluescriptI-ISK+ vector was obtained from Philip Murphy (NIH). The sequence encoding FPRL1 was amplified by the polymerase chain reaction using VENT polymerase (New England Biolabs, Inc., Beverly, Mass.) through 20 cycles and the following oligonucleotide primers:

```
#1   5' GGCGCCCGGTCTCCCATGGAAACCAACTTCTCCACT

#2   5' GGCGCCCGGTCTCCGATCCCATTGCCTGTAACTCAGTCTC
```

The PCR product was purified, restricted with BsaI and cloned into Cadus 1651 (pIPBX-1), a PGK promoter-driven expression vector, using NcoI and BamHI sites, to yield CADUS 2311. The sequence of the entire insert was determined and found to be identical to the FPRL-1 sequence deposited in GenBank (accession number M84562).

Preparation of Random Oligonucleotides

Library-Recycling Protocol to Identify a Surrogate Ligand

The yeast strain CY1141 (MATalpha far1*1441 tbt1-1 fus1-HIS3 can 1 ste14::trp1:;LYS2 ste3*1156 gpal(41)-Gal-phai2 lys2 ura3 leu2 trp1 his3) was used in the experiments that follow. CY1141 contains a pheromone inducible HIS3 gene, fus1-HIS3 integrated at the FUS1 locus and a hybrid gene encoding the first 41 amino acids of GPA1 (yeast G alpha) fused to sequence encoding human G alphai2 (lacking codons encoding the N-terminal 33 amino acids) replacing GPA1 at its chromosomal locus. The yeast STE14 gene is disrupted to lower the basal level of signaling through the pheromone response pathway. The yeast a-factor receptor gene, STE3, is deleted. CY1141 was transformed with Cadus 2311 to yield CY6571, a strain expressing the human orphan receptor, FPRL-1.

CY6571 exhibited LIRMA (ligand independent receptor mediated activation), that is, activation of the yeast pheromone pathway in the absence of ligand. It was determined that the yeast growth on selective media that resulted from LIRMA was eliminated by the additional of 2.5 millimolar concentrations of 3-aminotriazole (AT). AT is an inhibitor of the HIS3 gene product that serves to reduce background growth. Therefore, selection protocols aimed at the identification of surrogate ligands for the FPRL-1 receptor were carried out at this concentration of AT.

CY6571 was inoculated to 10 mls of standard synthetic media (SD) lacking leucine (-Leu) and incubated overnight at 30° C. The 10 ml overnight culture was used to inoculate 50 mls of YEPD; this culture was incubated at 30° C. for 4.5–5 hours at which time the cells were harvested and prepared for transformation with DNA encoding a random peptide library [alpha-NNK (6.24.94)] encoding tridecapeptides of random sequence, by electroporation. Post electroporation (in 0.2 cm cuvettes, 0.25 µF, 200 Ω, 1.5 kV) the cells were immediately diluted in 1 ml ice-cold 1M sorbitol and 100 µL aliquots were placed onto 10 synthetic media plates (pH6.8) lacking leucine and uracil (-Leu-Ura). The plates were incubated at 30° C. for 2–4 days at which time two replicas of each original transformation plate were made to synthetic media (pH6.8) lacking leucine, uracil and histidine and supplemented with 2.5 mM AT(-Leu-Ura-His+ 2.5 mM AT). The replicas were incubated at 30° C. for 3–5 days. Post incubation the colonies present on the replica sets of two were scraped from the plates into a total of 10 mls of $H_2O$ (5 mls each plate). The $OD_{600}$ of each cell suspension was determined and crude plasmid isolations were done on 8–16 OD units of cells for each pool. A total of eight pools resulted, due to lower numbers of yeast colonies present in four sets of plates. The pellets obtained from these crude plasmid isolations (the so called "smash and grab" technique, Methods in Yeast Genetics—A Laboratory Manual, 1990, M. D. Rose, F. Winston and P. Heiler. Cold Spring Harbor Laboratory Press, Cold Spring Harbor, N.Y.), were resuspended in 40 µL of 10 mM Tris, 1 mM EDTA, pH8.0 and 1 µL was used to transform E. coli by electroporation (0.1 cm cuvettes, 0.25 µF, 200 Ω, 1.8 kV). Post electroporation the cells were immediately diluted into 1 ml 2XYT media and incubated, with shaking, at 37° C. for 30 minutes after which time the cells were used to inoculate 50 mls of 2×YT supplemented with 100 ug/ml ampicillin. The 10 resulting cultures were incubated at 37° C. overnight. Plasmid DNA was isolated from each of these bacteria cultures using Qiagen columns (Qiagen, Inc., Chatsworth, Calif.)). Each plasmid DNA pellet was resuspended in 50µL Tris 10 mM, EDTA 1 mM, pH 8.0.

Strain CY6571 was transformed with 1 μL of each plasmid pool by electroporation. Post electroporation the cells were diluted into 400 μL 1 M sorbitol. From each electroporated cell suspension, 1 μL and 400 μL of cells were plated on −Leu−Ura synthetic media, pH6.8 to yield "low density" and "high density" platings. The plates were incubated at 30° C. for 3 days, at which time replicas of both the low and high density plates were made to −Leu−Ura−His+2.5 mM AT. For those cases where enrichment for a plasmid capable of conferring a His+ phenotype had occurred, this would be reflected by an amplified number of His+ colonies on both the low and high density plates visible at days 2–3, although the amplification would be most obvious on the plates that had received a high density of cells. In the FPRL-1 experiment ⅛ pools showed amplification of His+ colonies. The cells were scraped from this plate into 5 mls of $H_2O$, the $OD_{600}$ of the cell suspension was determined and a crude plasmid isolation was done on 15 OD units of yeast cells. The pellet obtained was resuspended in 40 μL 10 mM Tris, 1 mM EDTA, pH8.0 and 1 μL was used to transform *E. coli*. Plasmid DNA was isolated by miniprep from 3 ml 2XYT cultures of single bacterial colonies resulting from this transformation. 10 DNA pellets (A1 through A10) deriving from individual bacterial colonies were resuspended in 20 μL 10 mM Tris 1 mM EDTA, pH8.0 and used to transform CY6571 (containing the FPRL-1 expression vector) and CY6263 (CY1141 containing a control expression vector lacking any receptor sequence) by electroporation. Cadus 1625, a control vector lacking sequences encoding a peptide, was included and used to transform both the receptor+ and receptor− strains of yeast. Transformants were first selected on −Leu−Ura, pH6.8 then three yeast transformants of each type (from 11 CY6571 transformations and 11 CY6263 transformations) were patched to −Leu−Ura, pH6.8 to expand the colonies. Once expanded, streaks of the transformants were made on −Leu−Ura−His+2.5 mM AT to test for growth in the absence of histidine. All plasmids except the one denoted A2 conferred a growth advantage on media lacking histidine to yeast bearing the FPRL-1-encoding plasmid but not to yeast lacking the receptor plasmid. The peptide sequence found to be encoded by plasmids A1 and A3–A10 is: SerLeuLeuTrpLeuThrCysArgProTrpGluAlaMet, and is encoded by the nucleotide sequence 5'-TCT CTG CTT TGG CTG ACT TGT CGG CCT TGG GAG GCG ATG-3'.

Activation of the Pheromone Response Pathway in Yeast Expressing the FPRL-1 Receptor and Peptide Agonist.

For verification of pheromone pathway activation and quantification of the stimulation, the activity of the fus1 promoter was determined colorimetrically using a fus1-lacZ fusion in a parallel set of test strains. CY1141, described above, was used as the recipient strain for these experiments. Transformants contained CADUS 1584 (pRS424-fus1-lacZ) in addition to receptor ($R^{+/-}$) and ligand ($L^{+/-}$) plasmids. Four strains (bearing the identical plasmids) were grown overnight in minimal media lacking leucine, uracil, and tryptophan, pH8.6. The overnight cultures were used to inoculate −Leu −Ura −Trp pH6.8 media and these new cultures were grown for approximately 4.5–5 hours to an $OD_{600}$ of less than 0.4. Assay of β-galactosidase activity (Guarente 1983) in cells from these cultures yielded the following results:

| | | |
|---|---|---|
| CY1141/CADUS 2311/peptide A1/CADUS 1584 | $R^+L^+$ | 28 units |
| CY1141/CADUS 2311/CADUS 1625/CADUS 1584 | $R^+L^-$ | 3 units |
| CY1141/CADUS 1289/peptide A1/CADUS 1584 | $R^-L^+$ | 3.5 units |
| CY1141/CADUS 1289/CADUS 1625/CADUS 1584 | $R^-L^-$ | 3.9 units |

The presence of receptor and peptide-encoding plasmids resulted in an average 8-fold stimulation over background levels of β-galactosidase.

Autocrine Activation of the Pheromone Response Pathway in Yeast Expressing by FPRL-1 Agonists or C5a Receptor Agonists.

Figure 11:
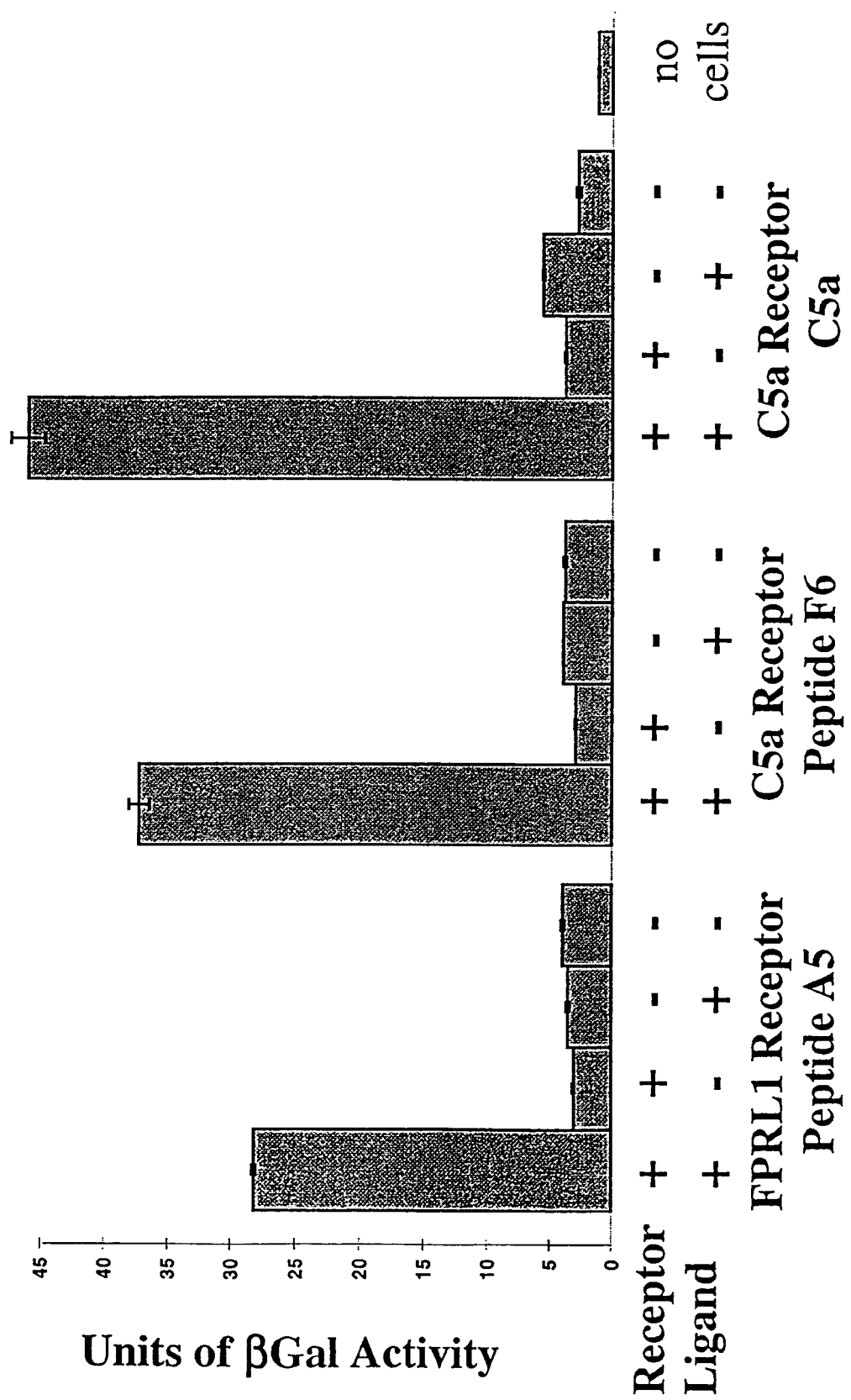
FIG. 11. Autocrine activation of the pheromone response pathway in yeast expressing FPRL-1 agonists or C5a receptor agonists.

The results illustrated in FIG. 11 were obtained using yeast cells engineered to express FPRL-1 or the C5a receptor under conditions wherein the signal transduction from the heterologous receptor was coupled to a fus1 :lacZ reporter gene construct described above. FIG. 11 demonstrates the specificity of the surrogate ligand A5 for FPRL-1, and the surrogate ligand F6, as well as that of the native C5a ligand, for the C5a receptor. In each instance, the presence of both the receptor and surrogate peptide result in an 8–12 fold increase in lacZ expression over the level observed in the absence of either the receptor, ligand, or both.

Activation of Human Neutrophils by a Surrogate FPRL Agonist.

Figure 12:
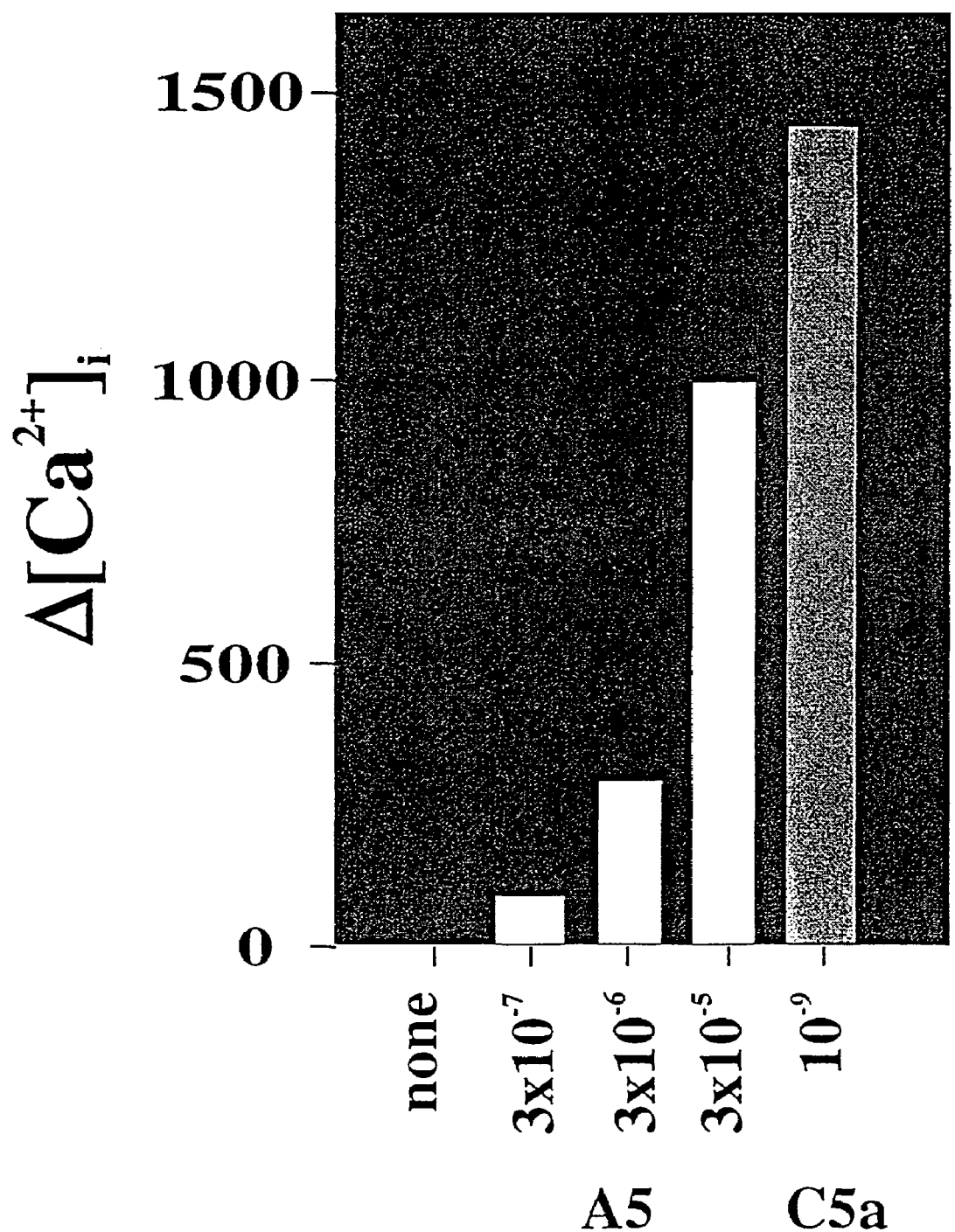
FIG. 12. Intracellular $Ca^{++}$ mobilization in neutrophils as detected by fluorescence activated Cell Sorter analysis using FURA2 dye absorbance ratio. The measurements were performed for the C5a peptide, or no peptide (control), or varying concentrations of the A5 peptide.

Human neutrophils in culture were stimulated with varying concentrations of the FPRL surrogate ligand A5, and intracellular $Ca^{++}$ mobilization was detected by Fluorescence Activated Cell Sorter (FACS) analysis based on FURA2 dye absorbance ratios. The response of the human neutrophils to the C5a peptide was also measured. As shown in FIG. 12, the A5 peptide produced a dose-dependent increase in intracellular calcium mobilization, indicating that it is capable of activating endogenous FPRL-mediated pathways in human neutrophils.

Preparation of Second Generation FPRL Ligand Libraries.

To further improve the selectivity and/or potency of the agonists identified by the above steps, we selected a surrogate peptide (A5), and created degenerate peptide libraries based on the sequence of that peptide as a starting point (e.g., a semi-random library) as follows:

```
FPRL-1 peptide A5
Ser-Leu-Leu-Trp-Leu-Thr-Cys-Arg-Pro-Trp-

Glu-Ala-Met sub-libraries
N-term
Xaa-Xaa-Xaa-Xaa-Xaa-Thr-Cys-Arg-Pro-Trp-

Glu-Ala-Met mid4
Ser-Leu-Leu-Trp-Leu-Xaa-Xaa-Xaa-Xaa-Trp-

Glu-Ala-Met

C-term
Ser-Leu-Leu-Trp-Leu-Thr-Cys-Arg-Pro-Xaa-

Xaa-Xaa-Xaa mod2
Xaa-Leu-Xaa-Trp-Xaa-Thr-Xaa-Arg-Xaa-Trp-
```

-continued

Xaa-Ala-Xaa mod3
Ser-Xaa-Leu-Xaa-Leu-Xaa-Cys-Xaa-Pro-Xaa-
Glu-Xaa-Met

Following the protocols set out above for the first generation peptide library, the second generation peptide library was screened, and individual clones isolated based on their ability to stimulate FPRL receptor dependent transcription.

Example 10

Identification of Surrogate Ligands using Expression of Random Peptide Library in Yeast Expressing the Orphan Mammalian Receptor, MDR-15

In a similar manner a plasmid encoding the monocyte derived receptor monocyte-derived receptor 15 (MDR15; Barella et al. (1995) *Biochem. J.* 309:773–9) was used to construct a yeast strain (CY6573) expressing this receptor. This receptor is an alternative spliced form of the Burkitt's lymphoma receptor 1 (BLR1) encoded by a human Burkitt's lymphoma cDNA (Dobner et al. (1992) *Eur. J. Immunol.* 22, 2795–2799). Strain CY6573 was transformed in a similar manner with the NNK13 library, and, following selection on ten -Leu-Ura (4.4×10⁵ colonies per plate), replica plated to -Leu-Ura-His+ 1 mM AT plates. Upon reisolation of plasmid pools and re-transformation into strain CY6573; eight of ten pools showed signicantly enriched colony formation on -Leu-Ura-His+ 1 mM AT plates. Eight unique plasmids derived from these pools when retransformed into CY6573 conferred growth on -Leu-Ura-His+ 1 mM AT plates. One of these plasmids failed to confer growth in a yeast strain lacking the MDR15 receptor.

Example 11

Identification of a Ligand using Expression of a Random Peptide Library in Yeast Expressing the Human Thrombin Receptor The receptor for thrombin, a G protein-coupled receptor, is present on numerous cell types including platelets, vascular smooth muscle, fibroblasts and on a subset of cells that function in immunity. Thrombin, a serine protease, binds to and cleaves the receptor molecule at residue 41, generating a new receptor N-terminus. The post-cleavage N-terminal residues then act as a "tethered ligand" to activate the receptor molecule (Vu et al. 1994). In platelets, signaling through the thrombin receptor has been shown to result in numerous effects including stimulation of phospholipase C, mobilization of intracellular $Ca^{2+}$ and inhibition of adenylyl cyclase.

In this example experiments that detail the following will be described (1) establishment of a strain of yeast designed to express the human G protein-coupled receptor for thrombin; (2) expression of a random peptide library in the afore-mentioned strain of yeast and (3) activation of the endogenous yeast pheromone pathway upon stimulation of the thrombin receptor by peptides encoded by a random library expressed within the same strain of yeast.

Preparation of a Yeast Expression Vector for a Mammalian Thrombin Receptor

The human thrombin receptor was amplified by PCR from pcDNA3:Hu-Thr9b-5' (Bristol Myers Squibb) using the following oligonucleotides:

5' GGGCCATGGGGCCGCGGCGGTTG 3'

5' CCCGGATCCTAAGTTAACAGCTTTTTGTATAT 3'

The amplified product was purified by gel electrophoresis, restricted with NcoI and BamHI and ligated to NcoI and BamHI-cut CADUS 1871, a PGK promoter-driven expression vector, to yield CADUS 2260. Cloning into CADUS 1871 introduces a novel stop codon preceded by the triplet GlySerVal after the authentic carboxy terminal codon of the human thrombin receptor (threonine). In addition, an invertase signal sequence is fused to the authentic amino terminus of the receptor.

CY7467 exhibited LIRMA (ligand independent receptor mediated activation), that is, activation of the yeast pheromone pathway in the absence of ligand. It was determined that the yeast growth on selective media that resulted from LIRMA was eliminated by the addition of 2.5 millimolar concentrations of 3-aminotriazole (AT). AT is an inhibitor of the HIS3 gene product that serves to reduce background growth. Therefore, selection protocols aimed at the identification of novel peptide ligands for the human thrombin receptor were carried out at this concentration of AT.

Preparation of Random Oligonucleotide Library
As described above.

Recycling Protocol to Identify a Surrogate Ligand

The yeast strain CY1141 (MATalpha far1*1442 tbt1-1 fus1-HIS3 can1 ste14::trp1::LYS2 ste3*1156 gpa1(41)-Galphai2 lys2 ura3 leu2 trp1 his3) was transformed with CADUS 2260 to yield strain CY7467, expressing the human thrombin receptor. CY7467 was inoculated to 10 mls of standard synthetic media (SD) lacking leucine (–Leu) and incubated overnight at 30 C. The 10 ml overnight culture was used to inoculate 50 mls of YEPD media; this culture was incubated at 30 C for 4.5–5 hours at which time the cells were harvested and prepared for transformation with DNA encoding a random peptide library [alpha-NNK (6.24.94)] by electroporation. Post electroporation (in 0.2 cm cuvettes, 0.25 mF, 200 W, 1.5 kV) the cells were immediately diluted in 1 ml ice-cold 1M sorbitol and 100 ML aliquots were plated onto 10 synthetic media plates (pH6.8) lacking leucine and uracil (–Leu–Ura). The plates were incubated at 30 C for 2–4 days at which time two replicas of each original transformation plate were made to synthetic media (pH6.8) lacking leucine, uracil and histidine and supplemented with 2.5 mM AT(–Leu–Ura–His+ 2.5 mM AT). The replicas were incubated at 30 C for 3–5 days. Post incubation the colonies present on the replica sets of two were scraped from the plates into a total of 10 mls of H2O (5 mls each plate). The $OD_{600}$ of each cell suspension was determined and crude plasmid isolations were done on 8–16 OD units of cells for each pool. A total of ten pools resulted. The pellets obtained from these crude plasmid isolations were resuspended in 40 mL of 10 mM Tris, 1 mM EDTA, pH8.0 and 1 mL was used to transform *E. coli* by electroporation (0.1 cm cuvettes, 0.25 mF, 200 W, 1.8 kV). Post electroporation the cells were immediately diluted into 1 ml 2XYT media and incubated, with shaking, at 37 C for 30 minutes after which time the cells were used to inoculate 50 mls of 2×YT supplemented with 100 ug/ml ampicillin. The 10 resulting cultures were incubated at 37 C overnight. Plasmid DNA was isolated from each of these bacterial cultures using Qiagen columns (Qiagen, Inc., Chatsworth, Calif.). Each plasmid DNA pellet was resuspended in 50 mL Tris 100 mM, EDTA 1 mM, pH 8.0.

Strain CY7467 was transformed with 1 mL of each plasmid pool by electroporation. Post electroporation the cells were diluted into 400 mL 1M sorbitol. From each electroporated cell suspension, 1 mL and 400 mL of cells were plated on −Leu−Ura synthetic media, pH6.8 to yield "low density" and "high density" platings. The plates were incubated at 30 C for 3 days, at which time replicas of both the low and high density plates were made to −Leu−Ura−His+ 2.5 mM AT. For those cases where enrichment for a plasmid capable of conferring a His+ phenotype had occurred, this would be reflected by an amplified number of His+ colonies on both the low and high density plates visible at days 2–3, although the amplification would be most obvious on the plates that had received a high density of cells. In this experiment 3/10 pools showed amplification of His+colonies. The cells from each of these plates were scraped into 5 mls of $H_2O$, the $OD_{600}$ of the cell suspensions were determined and crude plasmid isolations were done on 8–16 OD units of yeast cells. The pellets obtained were resuspended in 40 mL 10 mM Tris, 1 mM EDTA, pH8.0 and 1 mL was used to transform E. coli. Plasmid DNA was isolated by miniprep from 3 ml 2XYT cultures of single bacterial colonies resulting from these transformations (three bacterial colonies for each DNA pool were processed in this way). DNAs deriving from three individual bacterial colonies per pool were resuspended in 20 mL 10 mM Tris 1 mM EDTA, pH8.0. The three DNAs derived per pool were sequenced and found to encode identical peptides. Thus three differing DNA sequences were derived, one representing each amplified pool. One plasmid representing each of the three original amplified pools was used to transform CY7467 (containing the thrombin receptor expression vector) and CY6263 (CY1141 containing a control expression vector lacking any receptor sequence) by electroporation. CADUS 1625, a control vector lacking sequences encoding a peptide was included and used to transform both the receptor+ and receptor− strains of yeast. CADUS 1651, a control vector lacking sequences encoding a receptor included and used to transform both the ligand+ and ligand− strains of yeast. Transformants were first selected on −Leu−Ura, pH6.8, then two yeast transformants of each type were patched to −Leu−Ura, pH6.8 to expand the colonies. Once expanded, streaks of the transformants were made on −Leu−Ura−His+ 2.5 mM AT to test for growth in the absence of histidine. One of the three plasmids tested conferred a growth advantage on media lacking histidine to yeast bearing the thrombin-encoding plasmid but not to yeast lacking the receptor plasmid. The peptide sequence encoded by this plasmid is: Val-Cys-Pro-Ala-Arg-Tyr-Val-Leu-Pro-Gly-Pro-Val-Leu and was encoded by the nucleotide sequence GTT TGT CCT GCG CGT TAT GTG CTG CCT GGG CCT GTT TTG.

TABLE 1

Detection of C5a production in yeast by ELISA.

|  | R−L− | R+L− | R−L+ | R+L+ |
|---|---|---|---|---|
| [C5a] in culture | n.d. | n.d. | 0.64 ng/ml = 77 nM | 0.5 ng/ml = 60 nM |
| [C5a] released from lysed cells* | n.d. | n.d. | 0.8 ng/ml = 97 nM | 0.6 ng/ml = 73 nM |

C5a was detected by enzyme-linked immunosorbent assay (ELISA). Molar concentrations were calculated using MW = 8273 as predicted by C5a sequence.
*Determined by pelleting cells, resuspending cells in the original volume, breaking yeast with glass beads and assaying the resulting supernatant.
n.d. = not done

TABLE 2

Coupling of the C5a receptor to Gα chimeras in yeast.

| Chimera | Expression Context | Result |
|---|---|---|
| $GPA1_{41}$-Gαi2 | single copy, integrated, GPA1 promoter | Good signal to noise ratio: efficient coupling to yeast βγ. |
| $GPA1_{41}$-Gαi3 | single copy, integrated, GPA1 promoter | Poor signal to noise ratio: high background due to poor coupling to yeast βγ, high LIRMA*. |
| GPA1βam-Gαi2 | low copy plasmid, GPA 1 promoter | Signal equal to that with $GPA1_{41}$-Gαi2, however, background is greater. |
| GPA1βam-Gα16 | low copy plasmid, GPA1 promoter | Poor signal to noise ratio, high background due to poor coupling to yeast βγ, high LIRMA*. |
| GPA1βam-Gαs | low copy plasmid, GPA1 promoter | Unacceptably high background due to poor coupling to yeast β', high LIRMA*. |

*LIRMA = Ligand Independent Receptor Mediated Activation. With this phenomenon, there is an increase in growth on selective media for strains containing heterologous receptor in the absence of ligand. It is possible that some receptor antagonists would decrease LIRMA. It has been noted (Milano, et al. 1994) that specific antagonists reduce LIRMA of the β2 adrenergic receptor when that receptor is overexpressed in transgenic mice. LIRMA may be exploited in several ways, including the identification of antagonists capable of reducing the phenomenon. A subset of antagonists would be expected to affect the receptor conformation in such a way as to prevent the downstream signalling that occurs in the absence of agonist. LIRMA can be exploited to identify new G protein-coupled receptors by expressing cDNA clones in yeast strains expressing those chimeric G proteins which couple only poorly to yeast βγ. In addition, LIRMA may permit the identification of inhibitors that are specific for G proteins.

TABLE 3

Coupling of Gα switch region hybrids to the pheromone response pathway.

| Protein | GPA1 amino acid sequences | Gαs amino acid sequences | Phenotype |
|---|---|---|---|
| GPA1 | 1–472 | none | Couples with Gβγ |
| GαS | none | 1–394 | Couples with Gβγ weakly |
| $GPA_{41}$-S | 1–41 | 42–394 | Couples with Gβγ weakly |
| SGS | 297–333 | 1–201 + 237–394 | Does not couple with Gβγ |
| $GPA_{41}$-SGS | 1–41 + 297–333 | 42–201 + 237–394 | Couples with Gβγ weakly |

We claim:

1. A mixture of recombinant yeast cells, each cell of which has a cell membrane and each cell of which comprises:
   (a) a heterologous receptor selected from the group consisting of: an FPRL-1 receptor, a C5a receptor and a thrombin receptor, which receptor is expressed in the cell membrane of said cell such that signal transduction activity via said receptor is modulated by interaction of an extracellular region of the receptor with an extracellular signal; and
   (b) a heterologous polypeptide, wherein the heterologous polypeptide is transported to a location allowing interaction with the extracellular region of the heterologous receptor expressed in the cell membrane;
wherein collectively the mixture of cells expresses a library of said heterologous polypeptides, said library being expressible at a sufficient level such that modulation of the signal transduction activity of the heterologous receptor by a heterologous polypeptide within the library provides a detectable signal.

2. The mixture of recombinant yeast cells of claim 1, wherein each yeast cell further comprises a chimeric G protein subunit with which the heterologous receptor interacts.

3. The mixture of recombinant yeast cells of claim 1, which are a mutant strain of yeast cells having a pheromone system pathway that is desensitized at slower rate than a wild type strain under the same conditions of continuous stimulation of the pheromone system pathway.

4. The mixture of recombinant yeast cells of claim 1, wherein the yeast cells have a mutation in a gene selected from the group consisting of: STE50, bar1, pik1, msg5, sig1, and aft1.

5. The mixture of recombinant yeast cells of claim 1, wherein the yeast cells have a ste2 or ste3 mutation.

6. The mixture of recombinant yeast cells of claim 1, wherein an endogenous pheromone gene is not functionally expressed in the yeast cells.

7. The mixture of recombinant yeast cells of claim 1, wherein an endogenous FAR1 gene is not functionally expressed in the yeast cells.

8. The mixture of recombinant yeast cells of claim 1, wherein an endogenous SST2 gene is not functionally expressed in the yeast cells.

9. The mixture of recombinant yeast cells of claim 2, which comprise a chimeric Gαi2 subunit consisting of the first 41 amino acids of GPA1 fused to a region of human Gαi2.

10. The mixture of recombinant yeast cells of claim 1, which further comprise a selectable marker that is activated by a pheromone system pathway of the yeast cells, thereby providing the detectable signal.

11. The mixture of recombinant yeast cells of claim 10, wherein the selectable marker comprises a pheromone-responsive promoter operably linked to a selectable gene.

12. The mixture of recombinant yeast cells of claim 11, wherein the pheromone-responsive promoter is the FUS1 promoter.

13. The mixture of recombinant yeast cells of claim 11, wherein the selectable gene is a HIS 3 gene.

14. The mixture of recombinant yeast cells of claim 1, wherein the heterologous polypeptide includes a signal sequence that facilitates transport of the polypeptide to a location allowing interaction with the extracellular region of the receptor.

15. The mixture of recombinant yeast cells of claim 14, wherein the signal sequence corresponds to a leader peptide of the *Saccharomyces cerevisiae* α factor or a-factor.

16. The mixture of recombinant yeast cells of claim 1, which belong to the species *Saccharomyces cerevisiae*.

17. The mixture of recombinant yeast cells of claim 1, wherein the library of heterologous polypeptides includes more than 1000 different polypeptide sequences.

18. The mixture of recombinant yeast cells of claim 1, wherein said receptor is a C5a receptor.

19. The mixture of recombinant yeast cells of claim 1, wherein said heterologous receptor acts as a surrogate for an endogenous yeast pheromone receptor in a pheromone system pathway of said cell.

20. The mixture of recombinant yeast cells of claim 1, which further comprise a reporter gene construct containing a reporter gene in operative linkage with one or more transcriptional regulatory elements responsive to the signal transduction activity of the receptor protein which thereby provides the detectable signal.

21. The mixture of recombinant yeast cells of claim 20, wherein said reporter gene encodes a gene product which confers a growth signal.

22. The mixture of recombinant yeast cells of claim 1, wherein said detectable signal is selected from the group consisting of: color, fluorescence, luminescence, cell viability, relief of a cell nutritional requirement, cell growth, and drug resistance.

23. A mixture of recombinant yeast cells, each cell of which has a cell membrane and each cell of which comprises:
  (a) a heterologous receptor selected from the group consisting of an FPRL-1 receptor, a C5a receptor, and a thrombin receptor expressed in the cell membrane of said cell such that signal transduction activity via said receptor is modulated by interaction of an extracellular region of the receptor with an extracellular signal, said heterologous receptor acting as a surrogate for an endogenous yeast pheromone receptor in a pheromone system pathway of the yeast cell;
  (b) a heterologous polypeptide, wherein the heterologous polypeptide is transported to a location allowing interaction with the extracellular region of the heterologous receptor expressed in the cell membrane; and
  (c) a selectable marker that is activated by the pheromone system pathway;
  wherein collectively the mixture of cells expresses a library of said heterologous polypeptides, said library being expressible at a sufficient level such that modulation of the signal transduction activity of the heterologous receptor by a heterologous polypeptide within the library provides a detectable signal mediated by the selectable marker; and
  wherein said yeast cells have a mutation in at least one gene selected from the group consisting of FAR1, SST2, BAR1, SVG1, STE2, STE3, MFa1, MFa2, MFα1 and MFα2.

24. The mixture of recombinant yeast cells of claim 23, wherein the selectable marker comprises a pheromone-responsive promoter operably linked to a selectable gene.

25. The mixture of recombinant yeast cells of claim 23, wherein the heterologous polypeptide includes a signal sequence that facilitates transport of the polypeptide to a location allowing interaction with the extracellular region of the receptor.

* * * * *